(12) United States Patent
Slusher et al.

(10) Patent No.: US 6,395,718 B1
(45) Date of Patent: *May 28, 2002

(54) PHARMACEUTICAL COMPOSITIONS AND METHODS OF INHIBITING ANGIOGENESIS USING NAALADASE INHIBITORS

(75) Inventors: Barbara S. Slusher, Kingsville; Rena Lapidus, Pikesville, both of MD (US)

(73) Assignee: Guilford Pharmaceuticals Inc., Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/110,262

(22) Filed: Jul. 6, 1998

(51) Int. Cl.$^7$ .................... A61K 31/66; A61K 31/44; A61K 31/19
(52) U.S. Cl. .................... 514/75; 514/95; 514/121; 514/347; 514/570; 514/574
(58) Field of Search .................... 514/75, 95, 121, 514/347, 570, 574

(56) References Cited

U.S. PATENT DOCUMENTS

| | | | |
|---|---|---|---|
| 4,151,172 A | 4/1979 | Ondetti et al. | 260/326.2 |
| 4,168,267 A | 9/1979 | Petrillo, Jr. | 260/326.2 |
| 4,316,896 A | 2/1982 | Thorsett et al. | 424/200 |
| 4,337,201 A | 6/1982 | Petrillo, Jr. | 548/413 |

(List continued on next page.)

FOREIGN PATENT DOCUMENTS

| | | |
|---|---|---|
| CL | 651-91 | 2/1998 |
| WO | WO 95/23806 | 9/1995 |
| WO | WO 96/26272 | 8/1996 |

OTHER PUBLICATIONS

Stauch, B. et al., "The effects of N–acetylated alpha linked acidic dipeptidase (NAALADase) inhibitors on [$^3$H] NAAG catabolism in vivo," *Neuoscience Letters*, 100, p. 295–300 (1989).

Subasinghe, N. et al., "Synthesis of Acyclic and Dehydroaspartic Acid Analogues of Ac–Asp–Glu–OH and Their Inhibition of Rat Brain N–acetylated α–linked Acidic Dipeptidase (NAALA Dipeptidase)," *J. Med. Chem.*, 33, p. 2734–2744, (1990).

Rothstein, J. et al., "Abnormal excitatory amino acid metabolism in amyotrophic lateral sclerosis," *Anals of Neurology*, vol. 28, p. 18–25 (1990).

Slusher, B. et al., "Rat brain N–acetylated α–linked acidic dipeptidase activity," *The J. of Biological Chemistry*, vol. 265, No. 34, p. 21297–21301, (1990).

Tsai, G. et al., "Reductions in acidic amino acids and N–acetylaspartylglutamate in amyotrophic lateral sclerosis," *Brain Research*, 556, p. 151–161 (1991).

Coyle, J. et al., "N–acetyl–aspartyl glutamate," *Excitatory Amino Acids*, p. 69–77 (1990).

Meyerhoff, J. et al., "Genetically epilepsy–prone rats have increased brain regional activity of an enzyme whhich liberates glutamate from N–acetyl–aspartyl–glutamate," *Brain Research*, 593, p. 140–143 (1992).

Meyerhoff, J. et al., "Activity of a NAAG–hydrolyzing enzyme in brain may affect seizure susceptibility in genetically epilepsy–prone rats," *Molecular Neurobiology of Epilepsy*, p. 163–172 (1992).

Slusher, B. et al., "Immunocytochemical localization of the N–acetyl–aspartyl–glutamate (NAAG) hydrolyzing enzyme N–acetylated α–linked acidic dipeptidase (NAALADase)," *J. of Comp. Neurology*, 315, p. 217–229 (1992).

Tsai, G. et al., "Immunocytochemical distribution of N–acetylaspartylglutamate in the rat forebrain and glutamergic pathways," *J. of Chem. Neuroanatomy*, 6, p. 277–292 (1993).

Tsai, G. et al., "Changes of excitatory neurotransmitter metabolism in schizophrenic brains," *Salmon Lecturer of the New York Academy of Medicine*, (Dec. 2–3, 1993).

Slusher, B. et al., "NAALADase: A Potential Regulator of Synaptic Glutamate," *Biotech Update DuPont NEN*, 9, p. 37–39 (1994).

Koenig, M. et al., "N–acetyl–aspartyl–glutamate (NAAG) elicits rapid increase in intraneuronal $Ca^{2+}$ in vitro," *NeuroReports*, 5, p. 1063–1068 (1994).

Jackson, P. et al., "Design synthesis, and biological activity of a potent inhibitor of the neuropeptidase N–acetylated α–linked acidic dipeptidase," *J. of Medicinal Chemistry*, (1995).

Vornov, J. et al., "Toxic NMDA–receptor activation occurs during recovery in a tissue culture model of ischemia," *J. of Neurochemistry*, 65, p. 1681–1691 (1995).

Woods, D. et al., "Gender–linked injury after focal cerebral ischemia," *Soc. For Neuroscience 1996 Abstract Form*, (1996).

Bhardwaj, A. et al., "Striatal nitric oxide (NO) production is enhanced in focal cerebral ischemia: An in vivo microdialysis study," *Soc. For Neuroscience 1996 Abstract Form*, (1996).

Carter, R. et al., "Prostate–specific membrane antigen is a hydrolase with substrate and pharmacologic characteristics of neuropeptidase," *Proc. Nat. Acad. Sci.*, 93, p. 749–753 (1996).

Barren III, R. et al., "Method for Identifying Prostate Cells in Semen Using Flow Chytometry," *The Prostate*, 36, p. 181–188 (1998).

Primary Examiner—Dwayne C. Jones
Assistant Examiner—Donna Jagoe
(74) *Attorney, Agent, or Firm*—Lyon & Lyon LLP

(57) ABSTRACT

The present disclosure relates to a method of inhibiting angiogenesis comprising administering a N-Acetylated α-Linked Acidic Dipeptidase (NAALADase) inhibitor to a patient in need thereof, and a pharmaceutical composition comprising an anti-angiogenic effective amount of a NAALADase inhibitor and a pharmaceutically acceptable carrier.

46 Claims, 4 Drawing Sheets

U.S. PATENT DOCUMENTS

| | | | |
|---|---|---|---|
| 4,374,131 A | 2/1983 | Petrillo, Jr. | 424/200 |
| 4,444,765 A | 4/1984 | Karanewsky et al. | 424/200 |
| 4,448,772 A | 5/1984 | Karanewsky | 424/200 |
| 4,452,790 A | 6/1984 | Karanewsky et al. | 424/200 |
| 4,452,791 A | 6/1984 | Ryono et al. | 424/200 |
| 4,468,519 A | 8/1984 | Krapcho | 548/409 |
| 4,547,324 A | 10/1985 | Wong et al. | 260/502.4 |
| 4,555,506 A | 11/1985 | Karanewsky et al. | 514/91 |
| 4,560,680 A | 12/1985 | Ryono et al. | 514/82 |
| 4,560,681 A | 12/1985 | Karanewsky | 514/82 |
| 4,567,166 A | 1/1986 | Karanewsky et al. | 514/82 |
| 4,616,005 A | 10/1986 | Karanewsky et al. | 514/80 |
| 4,671,958 A | 6/1987 | Rodwell et al. | 424/85 |
| 4,703,043 A | 10/1987 | Karanewsky et al. | 514/80 |
| 4,715,994 A | 12/1987 | Parsons et al. | 200/502.5 E |
| 4,716,155 A | 12/1987 | Karanewsky et al. | 514/89 |
| 4,741,900 A | 5/1988 | Alvarez et al. | 424/85 |
| 4,849,525 A | 7/1989 | Weller, III et al. | 548/413 |
| 4,853,326 A | 8/1989 | Quash et al. | 435/5 |
| 4,867,973 A | 9/1989 | Goers et al. | 424/85.91 |
| 4,885,283 A | 12/1989 | Broadhurst et al. | 514/78 |
| 4,906,779 A | 3/1990 | Weber et al. | 564/238 |
| 4,918,064 A | 4/1990 | Cordi et al. | 514/114 |
| 4,937,183 A | 6/1990 | Ultee et al. | 435/68.1 |
| 4,950,738 A | 8/1990 | King et al. | 530/322 |
| 4,959,493 A | 9/1990 | Ohfume et al. | 562/506 |
| 4,962,097 A | 10/1990 | Parsons et al. | 514/114 |
| 4,966,999 A | 10/1990 | Coughlin et al. | 564/150 |
| 4,988,681 A | 1/1991 | Ishikawa et al. | 514/93 |
| 4,994,446 A | 2/1991 | Sokolovsky et al. | 514/75 |
| 5,030,732 A | 7/1991 | Morita et al. | 548/344 |
| 5,041,644 A | 8/1991 | Morita et al. | 562/565 |
| 5,047,227 A | 9/1991 | Rodwell et al. | 424/1.1 |
| 5,061,806 A | 10/1991 | Morita et al. | 548/112 |
| 5,093,525 A | 3/1992 | Weber et al. | 564/238 |
| 5,099,063 A | 3/1992 | Parsons et al. | 562/16 |
| 5,136,080 A | 8/1992 | Miller et al. | 558/410 |
| 5,140,104 A | 8/1992 | Coughlin et al. | 530/330 |
| 5,143,908 A | 9/1992 | Parsons et al. | 514/114 |
| 5,145,990 A | 9/1992 | Parsons et al. | 562/16 |
| 5,147,867 A | 9/1992 | Parsons et al. | 514/114 |
| 5,156,840 A | 10/1992 | Goers et al. | 424/85.91 |
| 5,162,504 A | 11/1992 | Horoszewicz | 530/388.2 |
| 5,162,512 A | 11/1992 | King et al. | 536/6.4 |
| 5,190,976 A | 3/1993 | Weber et al. | 514/634 |
| 5,196,510 A | 3/1993 | Rodwell et al. | 530/324 |
| 5,242,915 A | 9/1993 | Ueda et al. | 514/210 |
| 5,262,568 A | 11/1993 | Weber et al. | 564/238 |
| H1312 H | 5/1994 | Coughlin et al. | 530/331 |
| 5,326,856 A | 7/1994 | Coughlin et al. | 534/14 |
| 5,336,689 A | 8/1994 | Weber et al. | 514/634 |
| 5,449,761 A | 9/1995 | Belinka, Jr. et al. | 534/10 |
| 5,464,819 A | 11/1995 | Suzuki | 514/16 |
| 5,474,547 A | 12/1995 | Aebischer et al. | 604/891.1 |
| 5,489,525 A | 2/1996 | Pastan | 435/7.23 |
| 5,495,042 A | 2/1996 | Belinka, Jr. et al. | 562/14 |
| 5,500,420 A | 3/1996 | Maiese | 514/131 |
| 5,508,273 A | 4/1996 | Beers et al. | 514/141 |
| 5,527,885 A | 6/1996 | Coughlin et al. | 534/14 |
| 5,538,866 A | 7/1996 | Israeli et al. | 435/69.3 |
| 5,538,957 A | 7/1996 | Tsaklakidis et al. | 514/114 |
| 5,672,592 A | 9/1997 | Jackson et al. | 514/75 |
| 5,698,402 A | 12/1997 | Luderer et al. | 435/7.4 |
| 5,795,877 A | 8/1998 | Jackson et al. | 514/75 |
| 5,804,602 A * | 9/1998 | Slusher et al. | 514/574 |
| 5,824,662 A | 10/1998 | Slusher et al. | 514/75 |
| 5,863,536 A | 1/1999 | Jackson et al. | 424/130.1 |
| 5,880,112 A | 3/1999 | Jackson et al. | 514/121 |
| 5,902,817 A | 5/1999 | Jackson et al. | 514/347 |
| 5,962,521 A | 10/1999 | Jackson et al. | 514/530 |
| 5,968,915 A | 10/1999 | Jackson et al. | 514/89 |
| 5,977,090 A | 11/1999 | Slusher et al. | 514/143 |
| 5,981,209 A | 11/1999 | Slusher et al. | 514/23 |
| 5,985,855 A | 11/1999 | Slusher et al. | 514/75 |
| 6,004,946 A | 12/1999 | Slusher et al. | 514/75 |
| 6,011,021 A | 1/2000 | Slusher et al. | 514/75 |
| 6,017,903 A | 1/2000 | Slusher et al. | 514/75 |
| 6,025,344 A | 2/2000 | Jackson et al. | 514/75 |
| 6,025,345 A | 2/2000 | Jackson et al. | 514/75 |
| 6,028,216 A | 2/2000 | Morales et al. | 562/24 |
| 6,046,180 A | 4/2000 | Jackson et al. | 514/75 |
| 6,054,444 A | 4/2000 | Jackson et al. | 514/89 |
| 6,071,965 A | 6/2000 | Jackson et al. | 514/574 |
| 6,121,252 A | 9/2000 | Jackson et al. | 514/89 |
| 6,228,888 B1 | 5/2001 | Slusher et al. | 514/574 |

* cited by examiner

VEHICLE 1 ug/day 10 ug/day 100 ug/day

PHARMACEUTICAL COMPOSITIONS AND METHODS OF INHIBITING ANGIOGENESIS USING NAALADASE INHIBITORS

BACKGROUND OF THE INVENTION

1. Field of the Invention

The present invention relates to a pharmaceutical composition and a method for inhibiting angiogenesis comprising administering a N-Acetylated Alpha-Linked Acidic Dipeptidase (NAALADase) inhibitor to a patient in need thereof.

2. Description of Prior Art

Angiogenesis

The term "angiogenesis" describes the process whereby new capillaries are formed.

Angiogenesis is essential for normal physiological processes, such as growth, fertility and soft tissue wound healing. However, a significant percentage of all diseases are also dependent upon angiogenesis.

Cancer, for example, is an angiogenesis-dependent disease. Cancer tumor cells secrete or release angiogenic substances that activate nearby endothelial cells. These endothelial cells respond by expressing a cell autonomous pattern of behavior that culminates in the formation of new blood vessels. Research during the last three decades has demonstrated that angiogenesis is necessary to sustain the growth, invasion and metastasis of cancer tumors.

In addition to cancer, ailments such as rheumatoid arthritis, cardiovascular disease, neovascular diseases of the eye, peripheral vascular disorders, and dermatologic ulcers are dependent upon angiogenesis.

Research has shown that inhibiting angiogenesis offers a treatment that is complementary to, or an alternative to, traditional anti-angiogenic treatment options, such as surgical, chemo- and radiation therapies.

NAALADase Inhibitors

NAAG and NAALADase have been implicated in several human and animal pathological conditions relating to glutamate abnormalities and neurotoxicity. For example, it has been demonstrated that intra-hippocampal injections of NAAG elicit prolonged seizure activity. More recently, it was reported that rats genetically prone to epileptic seizures have a persistent increase in their basal level of NAALADase activity. These observations lend support to the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs. Additionally, NAALADase activity is significantly increased (two- to three-fold) in post-mortem spinal cord tissue from ALS patients and HCSMA dogs. As such, NAALADase inhibitors might be clinically useful in curbing the progression of ALS if an increased metabolism of NAAG is responsible for the alterations of CSF levels of these acidic amino acids and peptides.

Abnormalities in NAAG levels and NAALADase activity have also been documented in post-mortem schizophrenic brain, specifically in the prefrontal and limbic brain regions.

Applicant inventors have made the surprising and unexpected discovery that NAALADase inhibitors can affect angiogenesis in tissues containing NAALADase. Previous research has shown that NAALADase is enriched in synaptic plasma membranes and is primarily localized to neural and kidney tissue. NAALADase has also been found in the tissues of the prostate and testes. Additionally, previous findings have shown NAALADase to be present in neovasculature. Furthermore, as NAALADase continues to be discovered in other tissues of the body, NAALADase inhibitors most likely will also show efficacy in the inhibition of angiogenesis in those tissues.

While a few NAALADase inhibitors have been identified, they have only been used in non-clinical research. Examples of such inhibitors include general metallopeptidase inhibitors such as o-phenanthroline, metal chelators such as EGTA and EDTA, and peptide analogs such as quisqualic acid and β-NAAG. Accordingly, a need exists for new NAALADase inhibitors, as well as pharmaceutical compositions and methods using such new and known NAALADase inhibitors, to inhibit angiogenesis.

SUMMARY OF THE INVENTION

The present invention relates to pharmaceutical compositions comprising:

(i) an anti-angiogenic effective amount of a NAALADase inhibitor; and (ii) a pharmaceutically acceptable carrier.

The present invention further relates to methods of inhibiting angiogenesis, comprising administering an effective amount of a NAALADase inhibitor to a patient in need thereof.

BRIEF DESCRIPTION OF THE DRAWINGS

FIG. 1/Row 1 shows that a good angiogenic response was observed in the vehicle dose group.

FIG. 1/Row 2 is a set of microphotographs of Matrigel™ plugs subcutaneously injected into mice and treated with daily 3 mg/kg dosages of 2-(phosphono)pentanedioic acid following injection of an angiogenic factor. FIG. 1/Row 2 shows that the Matrigel™ plugs from the 3 mg/kg daily dose group had decreased neovasculature or angiogenesis.

FIG. 1/Row 3 is a set of microphotographs of Matrigel™ plugs subcutaneously injected into mice and treated with daily 30 mg/kg dosages of 2-(phosphono)pentanedioic acid following injection of an angiogenic factor. FIG. 1/Row 3 shows that the Matrigel™ plugs from the 30 mg/kg daily dose group had decreased neovasculature or angiogenesis.

FIG. 2 shows that a strong angiogenic response was observed in the vehicle.

FIG. 3 shows that a strong angiogenic response was observed in the 1 μg/day dose group.

FIG. 4 shows that delivery of 10 μg/day of 2-(phosphono) pentanedioic acid significantly decreased angiogenesis in the Matrigel™ /bFGF gels.

FIG. 5 shows that delivery of 100 μg/day of 2-(phosphono) pentanedioic acid significantly decreased angiogenesis in the Matrigel™ /bFGF gels.

DETAILED DESCRIPTION OF THE INVENTION

Definitions

Figure 1:
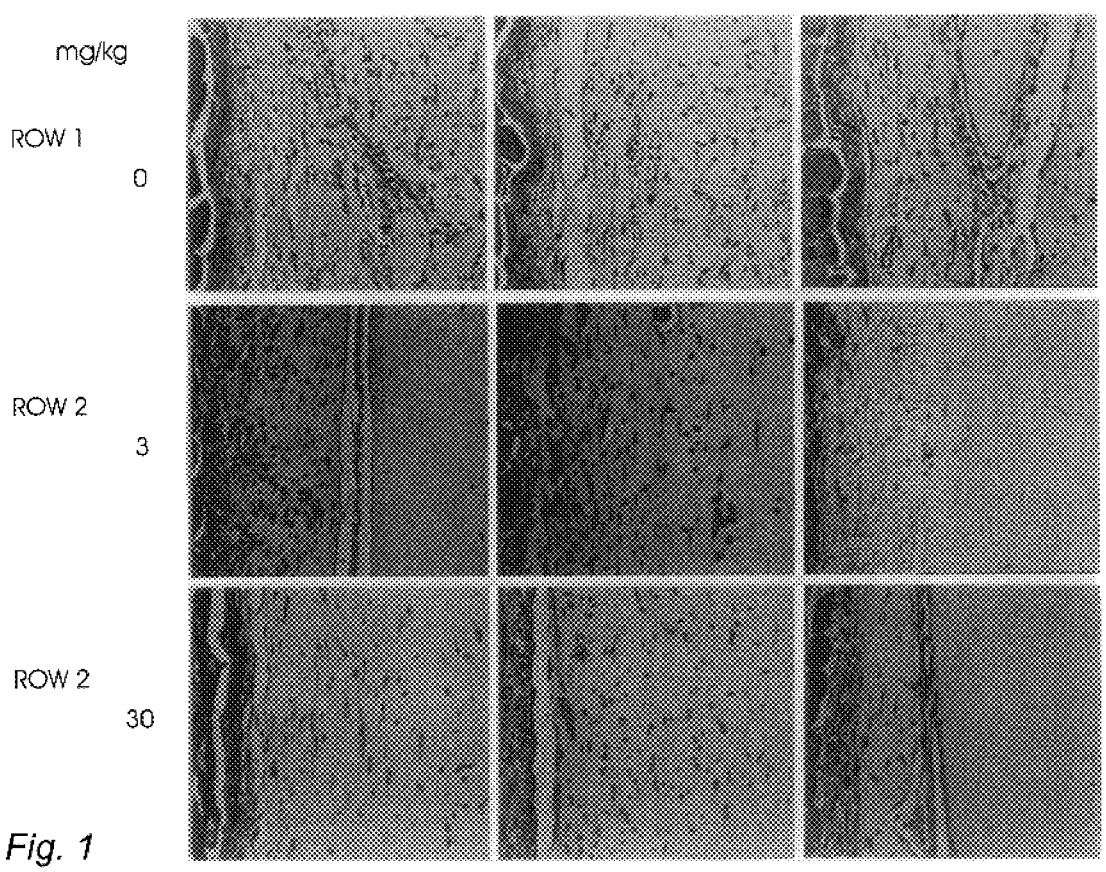
FIG. 1/Row 1 is a set of microphotographs of Matrigel™ plugs subcutaneously injected into mice and treated with a vehicle alone following injection of an angiogenic factor.

"Alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, isopropyl, butyl, iso-butyl, tert-butyl, n-pentyl, n-hexyl, and the like, unless otherwise indicated.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy" means the group —OR wherein R is alkyl as herein defined. Preferably, R is a branched or unbranched saturated hydrocarbon chain containing 1 to 6 carbon atoms.

"Ar" means an aryl, heteroaryl, carbocycle, or heterocycle that is a cyclic or fused cyclic ring and includes a mono-, bi- or tricyclic, carbo- or heterocyclic ring, wherein the ring is either unsubstituted or substituted in one or more position(s) with hydrogen, hydroxy, carbonyl, amino, amido, cyano, isocyano, nitro, nitroso, nitrilo, isonitrilo, imino, azo, diazo, sulfonyl, sulfhydryl, sulfoxy, thio, thiocarbonyl, thiocyano, formanilido, thioformamido, alkoxy, alkenoxy, alkylaryloxy, aryloxy, arylalkyloxy, alkylamino, aminoalkyl, thioalkyl, alkylthio, $C_1$–$C_6$ straight or branched chain alkyl and carbocyclic and heterocyclic moieties; wherein the individual ring sizes are 5–8 members; wherein the heterocyclic ring contains 1–4 heteroatom(s) selected from the group consisting of O, N, or S; wherein aromatic or tertiary alkyl amines are optionally oxidized to a corresponding N-oxide.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, and adamanyl.

Particularly preferred aryl or heteroaryl moieties include but are not limited to phenyl, benzyl, naphthyl, pyrrolyl, pyrrolidinyl, pyridinyl, pyrimidinyl, purinyl, quinolinyl, isoquinolinyl, furyl, thiophenyl, imidazolyl, oxazolyl, thiazolyl, pyrazolyl, and thienyl.

"Cancer", as used herein, includes, but is not limited to, types of cancer selected from the following group: ACTH-producing tumors, acute lymphocytic leukemia, acute non-lymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

"Diastereoisomers" are stereoisomers which are not mirror images of each other.

"Electromagnetic radiation" as used in this specification includes, but is not limited to, radiation having the wavelength of $10^{-20}$ to $10^0$ meters. Preferred embodiments of the present invention employ the electromagnetic radiation of: gamma-radiation ($10^{-20}$ to $10^{-13}$ m) x-ray radiation. ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

"Enantiomers" are a pair of stereoisomers that are non-superimposable mirror images of each other.

"Halo" means at least one fluoro, chloro, bromo, or iodo moiety, unless otherwise indicated.

"Inhibiting" or "inhibition", in the context of angiogenesis, may be assessed by delayed appearance of neovascular structures, slowed development of neovascular structures, decreased occurrence of neovascular structures, slowed or decreased severity of angiogenesis-dependent disease effects, arrested angiogenic growth and regression of previous angiogenic growth, among others. In the extreme, complete inhibition is referred to herein as prevention.

"Inhibition" of angiogenesis may be measured by many parameters in accordance with the present invention and, for instance, may be assessed by delayed appearance of neovascular structures, slowed development of neovascular structures, decreased occurrence of neovascular structures, slowed or decreased severity of angiogenesis-dependent disease effects, arrested angiogenic growth, or regression of previous angiogenic growth. In the extreme, complete inhibition is referred to herein as prevention.

The term "inhibition", in the context of enzyme inhibition, relates to reversible enzyme inhibition such as competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex:

$$E+I=EI \qquad 5$$

Following the Michaelis-Menten formalism, we can define the inhibitor constant, $K_i$, as the dissociation constant of the enzyme-inhibitor complex:

$$K_i = \frac{[E][I]}{[EI]}$$

Thus, in accordance with the above and as used herein, $K_i$ is essentially a measurement of affinity between a molecule, and its receptor, or in relation to the present invention, between the present inventive compounds and the enzyme to be inhibited. It should be noted that "$IC_{50}$" is a related term used when defining the concentration or amount of a compound that is required to cause a 50% inhibition of the target enzyme.

"Isomers" are different compounds that have the same molecular formula and includes cyclic isomers such as (iso)indole and other isomeric forms of cyclic moieties.

"Metastasis"—as set out in Hill, R. P, Chapter 11, Metastasis, pp. 178–195 in The Basic Science of Oncology, Tannock et al., Eds., McGraw-Hill, New York (1992), which is incorporated by reference herein in its entirety—is "The ability of cells of a cancer to disseminate and form new foci of growth at noncontiguous sites (i.e., to form metastases)."

Similarly, metastasis is described in Aznavoorian et al., Cancer 71: 1368–1383 (1993), which is incorporated by reference herein in its entirety, as "The transition from in situ tumor growth to metastatic disease is defined by the ability of tumor cells of the primary site to invade local tissues and to cross tissue barriers. . . . To initiate the metastatic process, carcinoma cells must first penetrate the epithelial basement membrane and then invade the interstitial stroma. . . . For distant metastases, intravasation requires tumor cell invasion of the subendothelial basement membrane that must also be negotiated during tumor cell extravasation. . . . The development of malignancy is also associated with tumor-induced angiogenesis [which] not only allows for expansion of the primary tumors, but also permits easy access to the vascular compartment due to defects in the basement membranes of newly formed vessels."

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-Acetylated Alpha-linked Acidic Dipeptidase, a membrane-bound metallopeptidase which catabolizes NAAG to N-acetylaspartate (NAA) and glutamate:

Catabolism of NAAG by NAALADase

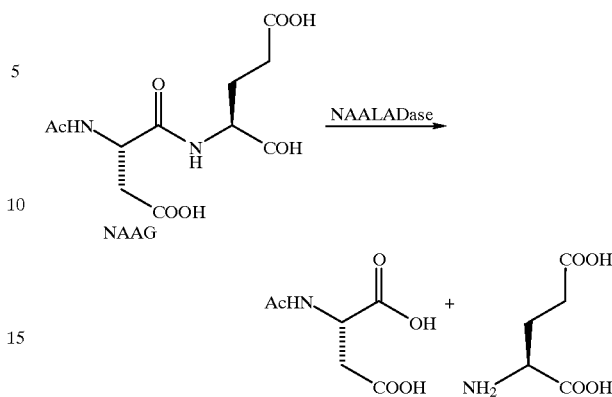

NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability. The enzyme was originally named for its substrate specificity for hydrolyzing N-acetylated alpha-linked acidic dipeptides. Currently, it is know that the enzyme has a broader range of substrate specificity than originally discovered, particularly that the enzyme does not require N-acetylation or alpha-linkage. Thus, as used herein "NAALADase" encompasses other names used in the literature such as NAAG hydrolyzing enzyme and NAALA dipeptidase.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burger's Medicinal Chemistry and Drug Chemistry, Fifth Ed., Vol. 1, pp. 172–178, 949–982 (1995). For example, the inventive compounds can be transformed into prodrugs by converting one or more of the hydroxy or carboxy groups into esters.

The term "pharmaceutically acceptable salt, ester, or solvate" refers to salt, ester, or solvates of the subject compounds which possess the desired pharmacological activity and which are neither biologically nor otherwise undesirable. The salt, ester, or solvates can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Base salt, ester, or solvates include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention may possess at least one asymmetric center and thus can be produced as mixtures of stereoisomers or as individual enantiomers or diastereomers. The individual stereoisomers may be obtained by using an optically active starting material, by resolving a racemic or non-racemic mixture of an intermediate at some appropriate stage of the synthesis, or by resolution of the compounds of the present invention. It is understood that the individual stereoisomers as well as mixtures (racemic and non-racemic) of stereoisomers are encompassed by the scope of the present invention. The S-stereoisomer at atom 1 of Formula I is most preferred due to its greater activity.

"Phenyl" includes all possible isomeric phenyl radicals, optionally monosubstituted or multi-substituted with substituents selected from the group consisting of amino, halo, haloalkyl, hydroxy, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, sulfonyl, $NR_2$ wherein $R_2$ is selected from the group consisting of hydrogen, ($C_1$–$C_6$)-straight or branched chain alkyl, ($C_3$–$C_6$)-straight or branched chain alkenyl or alkynyl, and ($C_1$–$C_4$) bridging alkyl wherein said bridging alkyl forms a heterocyclic ring starting with the nitrogen of $NR_1$ and ending with one of the carbon atoms of said alkyl or alkenyl chain, and wherein said heterocyclic ring is optionally fused to an Ar group.

"Prevention", in relation to angiogenesis or angiogenic growth, means no angiogenesis or angiogenic growth if none had previously occurred, or no further angiogenesis or angiogenic growth if there had already been growth.

"Racemic mixture" means a mixture containing equal parts of individual enantiomers. "Non-racemic mixture" is a mixture containing unequal parts of individual enantiomers or stereoisomers.

"Radiosensitizer", as used in this specification, is defined as a low molecular weight molecule administered to animals in therapeutically effective amounts to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention.

"Stereoisomers" are isomers that differ only in the way the atoms are arranged in space.

The term "treatment" as used herein covers any treatment of a disease and/or condition in an animal, particularly a human, and includes:
  (i) preventing a disease, disorder and/or condition from occurring in a person which may be predisposed to the disease, disorder and/or condition but has not yet been diagnosed as having it;
  (ii) inhibiting the disease, disorder and/or condition, i.e., arresting its development; and
  (iii) relieving the disease, disorder and/or condition, i.e., causing regression of the disease, disorder and/or condition.

Pharmaceutical Compositions of the Present Invention

The present invention relates to pharmaceutical compositions comprising:
  (i) an anti-angiogenic effective amount of a NAALADase inhibitor; and
  (ii) a pharmaceutically acceptable carrier.

The pharmaceutical composition may further comprise at least one additional therapeutic agent.

Since NAALADase is a metallopeptidase, useful NAALADase inhibitors for the pharmaceutical composition of the present invention include small molecule compounds with functional groups known to inhibit metallo-peptidases, such as hydroxyphosphinyl derivatives.

According to scientific literature, the glutamate moiety plays a more critical role than the aspartate moiety in the recognition of NAAG by NAALADase. As such, a preferred NAALADase inhibitor is a glutamate-derived hydroxyphosphinyl derivative, an acidic peptide analog, a conformationally restricted glutamate mimic or a mixture thereof.

A preferred acidic peptide analog is selected from the group consisting of Asp-Glu, Glu-Glu, Gly-Glu, gamma-Glu-Glu and Glu-Glu-Glu.

A preferred NAALADase inhibitor is a glutamate-derived hydroxyphosphinyl derivative of Formula I:

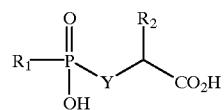

I or a pharmaceutically acceptable salt or hydrate thereof, wherein:
  Y is $CR_3R_4$, $NR_5$ or O;
  $R_1$ and $R_5$ are independently selected from the group consisting of hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, heteroaryl, carbocycle, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar or a mixture thereof;
  $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, Ar or a mixture thereof;
  $R_3$ and $R_4$ are independently selected from the group consisting of hydrogen, $C_1$–$C_6$ straight or branched chain alkyl, $C_2$–$C_6$ straight or branched chain alkenyl, $C_3$–$C_8$ cycloalkyl, $C_5$–$C_7$ cycloalkenyl, Ar, halo and mixtures thereof;
  Ar is a carbocyclic or heterocyclic moiety, which is unsubstituted or substituted with one or more substituent(s).

Examples of useful alkyl groups include, without limitation, methyl, ethyl, propyl, isopropyl, butyl, tert-butyl, n-pentyl, 2-methyl pentyl and the like.

Possible substituents of $R_1$, $R_2$, $R_3$, $R_4$, $R_5$, $R_6$, $R_7$, $R_8$ and $Ar_1$ include, without limitation, $C_1$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl and adamantyl.

Preferably, Y is $CH_2$.

More preferably, $R_2$ is substituted with carboxy.

Even more preferably, $R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof; and $R_2$ is $C_1$–$C_2$ alkyl.

Most preferably, the glutamate-derived hydroxyphosphinyl derivative is selected from the group consisting of:

2-[[(2-carboxyethyl)hydroxyphosphinyl]methyl] pentanedioic acid;
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[(cyclohexyl)methylhydroxyphosphinyl]methyl] pentanedioic acid;
2-[[phenylhydroxyphosphinyl]methyl]pentanedioic acid;
2-[(benzylhydroxyphosphinyl)methyl]pentanedioic acid;
2-[[(phenylmethyl)hydroxyphosphinyl]methyl]pentanedioic acid;
2-[[(phenylethyl)hydroxyphosphinyl]methyl]pentanedioic acid;
2-[[(phenylpropyl)hydroxyphosphinyl]methyl]pentanedioic acid;
2-[[(phenylbutyl)hydroxyphosphinyl]methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-[[(methoxybenzyl)hydroxyphosphinyl]methyl] pentanedioic acid;
2[[(2,3,4-trimethoxyphenyl)hydroxyphosphinyl]methyl] pentanedioic acid;
2-[[(phenylprop-2-enyl)hydroxyphosphinyl]methyl] pentanedioic acid;
2-[[(2-fluorobenzyl)hydroxyphosphinyl]methyl] pentanedioic acid;
2-[[((hydroxy)phenylmethyl)hydroxyphosphinyl]methyl] pentanedioic acid;
2-[[(3-methylbenzyl)hydroxyphosphinyl]methyl] pentanedioic acid;
2-[[(4-fluorophenyl)hydroxyphosphinyl]methyl] pentanedioic acid;
2-[[(3-trifluoromethylbenzyl)hydroxyphosphinyl]methyl] pentanedioic acid; and
pharmaceutically acceptable salts and hydrates thereof.

In other embodiments, $R_2$ is $C_3$–$C_9$ alkyl; $R_1$ is 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl or $C_1$–$C_4$ straight or branched chain alkyl substituted with 2-indolyl, 3-indolyl, 4-indolyl, 2-furyl, 3-furyl, tetrahydrofuranyl, 2-thienyl, 3-thienyl, 2-pyridyl, 3-pyridyl or 4-pyridyl; or $R_1$ is 1-naphthyl, 2-naphthyl, or $C_1$–$C_4$ straight or branched chain alkyl substituted with 1-naphthyl or 2-naphthyl.

Preferred compounds of these embodiments include:
2-[(methylhydroxyphosphinyl)methyl]hexanedoic acid;
2-[(benzylhydroxyphosphinyl)methyl]hexanedioic acid;
2-[(methylhydroxyphosphinyl)methyl]heptanedioic acid;
2-[(benzylhydroxyphosphinyl)methyl]heptanedioic acid;
2-[(methylhydroxyphosphinyl)methyl]octanedioic acid;
2-[(benzylhydroxyphosphinyl)methyl]octanedioic acid;
2-[(methylhydroxyphosphinyl)methyl]nonanedioic acid;
2-[(benzylhydroxyphosphinyl)methyl]nonanedioic acid;
2-[(methylhydroxyphosphinyl)methyl]decanedioic acid;
2-[(benzylhydroxyphosphinyl)methyl]decanedioic acid;
2-[[(2-pyridyl)methylhydroxyphosphinyl]methyl] pentanedioic acid;
2-[[(3-pyridyl)methylhydroxyphosphinyl]methyl] pentanedioic acid;
2-[[(4-pyridyl)methylhydroxyphosphinyl]methyl] pentanedioic acid;
2-[[(3-pyridyl)ethylhydroxyphosphinyl]methyl] pentanedioic acid;
2-[[(3-pyridyl)propylhydroxyphosphinyl]methyl] pentanedioic acid;
2-[[(tetrahydrofuranyl)methylhydroxyphosphinyl]methyl] pentanedioic acid;
2-[[(tetrahydrofuranyl)ethylhydroxyphosphinyl]methyl] pentanedioic acid;
2-[[(tetrahydrofuranyl)propylhydroxyphosphinyl]methyl] pentanedioic acid;
2-[[(2-tetrahydropyranyl)hydroxyphosphinyl]methyl] pentanedioic acid;
2-[[(3-tetrahydropyranyl)hydroxyphosphinyl]methyl] pentanedioic acid;
2-[[(4-tetrahydropyranyl)hydroxyphosphinyl]methyl] pentanedioic acid;
2-[[(2-indolyl)methylhydroxyphosphinyl]methyl] pentanedioic acid;
2-[[(3-indolyl)methylhydroxyphosphinyl]methyl] pentanedioic acid;

2-[[(4-indolyl)methylhydroxyphosphinyl]methyl] pentanedioic acid;
2-[[(3-indolyl)ethylhydroxyphosphinyl]methyl] pentanedioic acid;
2-[[(3-indolyl)propylhydroxyphosphinyl]methyl] pentanedioic acid;
2-[[(2-thienyl)methylhydroxyphosphinyl]methyl] pentanedioic acid;
2-[[(3-thienyl)methylhydroxyphosphinyl]methyl] pentanedioic acid;
2-[[(4-thienyl)methylhydroxyphosphinyl]methyl] pentanedioic acid;
2-[[(3-thienyl)ethylhydroxyphosphinyl]methyl] pentanedioic acid;
2-[[(3-thienyl)propylhydroxyphosphinyl]methyl] pentanedioic acid;
2-[[(2-pyridyl)hydroxyphosphinyl]methyl]pentanedioic acid;
2-[[(3-pyridyl)hydroxyphosphinyl]methyl]pentanedioic acid;
2-[[(4-pyridyl)hydroxyphosphinyl]methyl]pentanedioic acid;
2-[[(tetrahydrofuranyl)hydroxyphosphinyl]methyl] pentanedioic acid;
2-[[(2-indolyl)hydroxyphosphinyl]methyl]pentanedioic acid;
2-[[(3-indolyl)hydroxyphosphinyl]methyl]pentanedioic acid;
2-[[(4-indolyl)hydroxyphosphinyl]methyl]pentanedioic acid;
2-[[(2-thienyl)hydroxyphosphinyl]methyl]pentanedioic acid;
2-[[(3-thienyl)hydroxyphosphinyl]methyl]pentanedioic acid;
2-[[(4-thienyl)hydroxyphosphinyl]methyl]pentanedioic acid;
2-[[(1 -naphthyl)hydroxyphosphinyl]methyl]pentanedioic acid;
2-[[(2-naphthyl)hydroxyphosphinyl]methyl]pentanedioic acid;
2-[[(1-naphthyl)methylhydroxyphosphinyl]methyl] pentanedioic acid;
2-[[(2-naphthyl)methylhydroxyphosphinyl]methyl] pentanedioic acid;
2-[[(1-naphthyl)ethylhydroxyphosphinyl]methyl] pentanedioic acid;
2-[[(2-naphthyl)ethylhydroxyphosphinyl]methyl] pentanedioic acid;
2-[[(1-naphthyl)propylhydroxyphosphinyl]methyl] pentanedioic acid;
2-[[(2-naphthyl)propylhydroxyphosphinyl]methyl] pentanedioic acid;
2-[[(1-naphthyl)butylhydroxyphosphinyl]methyl] pentanedioic acid;
2-[[(2-naphthyl)butylhydroxyphosphinyl]methyl] pentanedioic acid; and
pharmaceutically acceptable salts and hydrates thereof.

In another preferred embodiment, Y is $CH_2$ and $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_{1-6}$ straight or branched chain alkyl, $C_2$–$C_6$ straight or branched chain alkenyl, $C_1$–$C_4$ alkoxy, phenyl or mixtures thereof.

More preferably, $R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof.

Most preferably, the glutamate-derived hydroxyphosphinyl derivative is selected from the group consisting of:
3-(methylhydroxyphosphinyl)-2-phenylpropanoic acid;
3-(ethylhydroxyphosphinyl)-2-phenylpropanoic acid;
3-(propylhydroxyphosphinyl)-2-phenylpropanoic acid;
3-(butylhydroxyphosphinyl)-2-phenylpropanoic acid;
3-(cyclohexylhydroxyphosphinyl)-2-phenylpropanoic acid;
3-((cyclohexyl)methylhydroxyphosphinyl)-2-phenylpropanoic acid;
3-(phenylhydroxyphosphinyl)-2-phenylpropanoic acid;
3-(benzylhydroxyphosphinyl)-2-phenylpropanoic acid;
3-(phenylethylhydroxyphosphinyl)-2-phenylpropanoic acid;
3-(phenylpropylhydroxyphosphinyl)-2-phenylpropanoic acid;
3-(phenylbutylhydroxyphosphinyl)-2-phenylpropanoic acid;
3-((2,3,4-trimethoxyphenyl)-3-hydroxyphosphinyl)-2-phenylpropanoic acid;
3-(phenylprop-2-enylhydroxyphosphinyl)-2-phenylpropanoic acid;
3-(benzylhydroxyphosphinyl)-2-ethylpropanoic acid;
3-(benzylhydroxyphosphinyl)-2-propylpropanoic acid;
3-(benzylhydroxyphosphinyl)-2-butylpropanoic acid;
3-(benzylhydroxyphosphinyl)-2-cyclohexylpropanoic acid;
3-(benzylhydroxyphosphinyl)-2-(cyclohexyl)methylpropanoic acid;
3-(benzylhydroxyphosphinyl)-2-phenypropanoic acid;
3-(benzylhydroxyphosphinyl)-2-benzylpropanoic acid;
3-(benzylhydroxyphosphinyl)-2-phenylethylpropanoic acid;
3-(benzylhydroxyphosphinyl)-2-phenylpropylpropanoic acid;
3-(benzylhydroxyphosphinyl)-2-phenylbutylpropanoic acid;
3-(benzylhydroxyphosphinyl)-2-(2,3,4-trimethoxyphenyl)-propanoic acid;
3-(benzylhydroxyphosphinyl)-2-phenylprop-2-enylpropanoic acid; and
pharmaceutically acceptable salts and hydrates thereof.

In other embodiments, at least one of $R_1$ and $R_2$ is 2-indolyl, 3-indolyl, 4-indolyl, 2-furyl, 3 -furyl, tetrahydrofuranyl, tetrahydropyranyl, 2-thienyl, 3-thienyl, 2-pyridyl, 3-pyridyl, 4-pyridyl, or $C_1$–$C_4$ straight or branched chain alkyl substituted with 2-indolyl 3-indolyl, 4-indolyl, 2-furyl, 3-furyl, tetrahydrofuranyl, 2-thienyl, 3-thienyl, 2-pyridyl, 3-pyridyl or 4-pyridyl; or $R_1$ is 1-naphthyl, 2-naphthyl, or $C_1$–$C_4$ straight or branched chain alkyl substituted with 1-naphthyl or 2-naphthyl.

Preferred compounds of these embodiments include:
3-[(2-pyridyl)methylhydroxyphosphinyl]-2-phenylpropanoic acid;
3-[(3-pyridyl)methylhydroxyphosphinyl]-2-phenylpropanoic acid;
3-[(4-pyridyl)methylhydroxyphosphinyl]-2-phenylpropanoic acid;
3-[(3-pyridyl)ethylhydroxyphosphinyl]-2-phenylpropanoic acid;
3-[(3-pyridyl)propylhydroxyphosphinyl]-2-phenylpropanoic acid;
3-[(tetrahydrofuranyl)methylhydroxyphosphinyl]-2-phenylpropanoic acid;

3-[(tetrahydrofuranyl)ethylhydroxyphosphinyl]-2-phenylpropanoic acid;
3-[(tetrahydrofuranyl)propylhydroxyphosphinyl]-2-phenylpropanoic acid;
3-[(2-indolyl)methylhydroxyphosphinyl]-2-phenylpropanoic acid;
3-[(3-indolyl)methylhydroxyphosphinyl]-2-phenylpropanoic acid;
3-[(4-indolyl)methylhydroxyphosphinyl]-2-phenylpropanoic acid;
3-[(3-indolyl)ethylhydroxyphosphinyl]-2-phenylpropanoic acid;
3-[(3-indolyl)propylhydroxyphosphinyl]-2-phenylpropanoic acid;
3-[(2-thienyl)methylhydroxyphosphinyl]-2-phenylpropanoic acid;
3-[(3-thienyl)methylhydroxyphosphinyl]-2-phenylpropanoic acid;
3-[(4-thienyl)methylhydroxyphosphinyl]-2-phenylpropanoic acid;
3-[(3-thienyl)ethylhydroxyphosphinyl]-2-phenylpropanoic acid;
3-[(3-thienyl)propylhydroxyphosphinyl]-2-phenylpropanoic acid;
3-(benzylhydroxyphosphinyl)-2-(2-pyridyl)methylpropanoic acid;
3-(benzylhydroxyphosphinyl)-2-(3-pyridyl)methylpropanoic acid;
3-(benzylhydroxyphosphinyl)-2-(4-pyridyl)methylpropanoic acid;
3-(benzylhydroxyphosphinyl)-2-(3-pyridyl)ethylpropanoic acid;
3-(benzylhydroxyphosphinyl)-2-(3-pyridyl)propylpropanoic acid;
3-(benzylhydroxyphosphinyl)-2 -(tetrahydrofuranyl)methylpropanoic acid;
3-(benzylhydroxyphosphinyl)-2-(tetrahydrofuranyl)ethylpropanoic acid;
3-(benzylhydroxyphosphinyl)-2-(tetrahydrofuranyl)propylpropanoic acid;
3-(benzylhydroxyphosphinyl)-2-(2-indolyl)methylpropanoic acid;
3-(benzylhydroxyphosphinyl)-2-(3-indolyl)methylpropanoic acid;
3-(benzylhydroxyphosphinyl)-2-(4-indolyl)methylpropanoic acid;
3-(benzylhydroxyphosphinyl)-2-(3-indolyl)ethylpropanoic acid;
3-(benzylhydroxyphosphinyl)-2-(3-indolyl)propylpropanoic acid;
3-(benzylhydroxyphosphinyl)-2-(2-thienyl)methylpropanoic acid;
3-(benzylhydroxyphosphinyl)-2-(3-thienyl)methylpropanoic acid;
3-(benzylhydroxyphosphinyl)-2-(4-thienyl)methylpropanoic acid;
3-(benzylhydroxyphosphinyl)-2-(3-thienyl)ethylpropanoic acid;
3-(benzylhydroxyphosphinyl)-2-(3-thienyl)propylpropanoic acid;
3-((1-naphthyl)hydroxyphosphinyl)-2-phenylpropanoic acid;
3-((2-naphthyl)hydroxyphosphinyl)-2-phenylpropanoic acid;
3-((1-naphthyl)methylhydroxyphosphinyl)-2-phenylpropanoic acid;
3-((2-naphthyl)methylhydroxyphosphinyl)-2-phenylpropanoic acid;
3-((1-naphthyl)ethylhydroxyphosphinyl)-2-phenylpropanoic acid;
3-((2-naphthyl)ethylhydroxyphosphinyl)-2-phenylpropanoic acid;
3-((1-naphthyl)propylhydroxyphosphinyl)-2-phenylpropanoic acid;
3-((2-naphthyl)propylhydroxyphosphinyl)-2-phenylpropanoic acid; 3-((1-naphthyl)butylhydroxyphosphinyl)-2-phenylpropanoic acid;
3-((2-naphthyl)butylhydroxyphosphinyl)-2-phenylpropanoic acid; and
pharmaceutically acceptable salts and hydrates thereof.

When Y is O, $R_2$ is preferably substituted with carboxy. Exemplary compounds of this embodiment include:

2-[[methylhydroxyphosphinyl]oxy]pentanedioic acid;
2-[[ethylhydroxyphosphinyl]oxy]pentanedioic acid;
2-[[propylhydroxyphosphinyl]oxy]pentanedioic acid;
2-[[butylhydroxyphosphinyl]oxy]pentanedioic acid;
2-[[cyclohexylhydroxyphosphinyl]oxy]pentanedioic acid;
2-[[(cyclohexyl)methylhydroxyphosphinyl]oxy]pentanedioic acid;
2-[[phenylhydroxyphosphinyl]oxy]pentanedioic acid;
2-[[benzylhydroxyphosphinyl]oxy]pentanedioic acid;
2-[[phenylethylhydroxyphosphinyl]oxy]pentanedioic acid;
2-[[phenylpropylhydroxyphosphinyl]oxy]pentanedioic acid;
2-[[phenylbutylhydroxyphosphinyl]oxy]pentanedioic acid;
2-[[(4-methylbenzyl)hydroxyphosphinyl]oxy]pentanedioic acid;
2-[[(4-fluorobenzyl)hydroxyphosphinyl]oxy]pentanedioic acid;
2-[[(2-fluorobenzyl)hydroxyphosphinyl]oxy]pentanedioic acid;
2-[[(pentafluorobenzyl)hydroxyphosphinyl]oxy]pentanedioic acid;
2-[[(methoxybenzyl)hydroxyphosphinyl]oxy]pentanedioic acid;
2-[[(2,3,4-trimethoxyphenyl)hydroxyphosphinyl]oxy]pentanedioic acid;
2-[[(1-naphthyl)hydroxyphosphinyl]oxy]pentanedioic acid;
2-[[(2-naphthyl)hydroxyphosphinyl]oxy]pentanedioic acid;
2-[[(1-naphthyl)methylhydroxyphosphinyl]oxy]pentanedioic acid;
2-[[(2-naphthyl)methylhydroxyphosphinyl]oxy]pentanedioic acid;
2-[[(1-naphthyl)ethylhydroxyphosphinyl]oxy]pentanedioic acid;
2-[[(2-naphthyl)ethylhydroxyphosphinyl]oxy]pentanedioic acid;
2-[[(1-naphthyl)propylhydroxyphosphinyl]oxy]pentanedioic acid;
2-[[(2-naphthyl)propylhydroxyphosphinyl]oxy]pentanedioic acid;
2-[[(1-naphthyl)butylhydroxyphosphinyl]oxy]pentanedioic acid;
2-[[(2-naphthyl)butylhydroxyphosphinyl]oxy]pentanedioic acid;
2-[[(phenylprop-2-enyl)hydroxyphosphinyl]oxy]pentanedioic acid;
2-[[benzylhydroxyphosphinyl]oxy]pentanedioic acid;
2-[[((hydroxy)phenylmethyl)hydroxyphosphinyl]oxy]pentanedioic acid;
2-[[(3-methylbenzyl)hydroxyphosphinyl]oxy]pentanedioic acid;
2-[[(4-fluorophenyl)hydroxyphosphinyl]oxy]pentanedioic acid;
2-[[(2-fluorobenzyl)hydroxyphosphinyl]oxy]pentanedioic acid;

2-(phosphono)oxy]pentanedioic acid;
2-[[(3-trifluoromethylbenzyl)hydroxyphosphinyl]oxy] pentanedioic acid;
2-[[methylhydroxyphosphinyl]oxy]-2-phenylethanoic acid;
2-[[ethylhydroxyphosphinyl]oxy]-2-phenylethanoic acid;
2-[[propylhydroxyphosphinyl]oxy]-2-phenylethanoic acid;
2-[[butylhydroxyphosphinyl]oxy]-2-phenylethanoic acid;
2-[[cyclohexylhydroxyphosphinyl]oxy]-2-phenylethanoic acid;
2-[[(cyclohexyl)methylhydroxyphosphinyl]oxy]-2-phenylethanoic acid;
2-[[phenylhydroxyphosphinyl]oxy]-2-phenylethanoic acid;
2-[[benzylhydroxyphosphinyl]oxy]-2-phenylethanoic acid;
2-[[phenylethylhydroxyphosphinyl]oxy]-2-phenylethanoic acid;
2-[[phenylpropylhydroxyphosphinyl]oxy]-2-phenylethanoic acid;
2-[[phenylbutylhydroxyphosphinyl]oxy]-2-phenylethanoic acid;
2-[[(2,3,4-trimethoxyphenyl)-3-hydroxyphosphinyl]oxy]-2-phenylethanoic acid;
2-[[(1-naphthyl)hydroxyphosphinyl]oxy]-2-phenylethanoic acid;
2-[[(2-naphthyl)hydroxyphosphinyl]oxy]-2-phenylethanoic acid;
2-[[(1-naphthyl)methylhydroxyphosphinyl]oxy]-2-phenylethanoic acid;
2-[[(2-naphthyl)methylhydroxyphosphinyl]oxy]-2-phenylethanoic acid;
2-[[(1-naphthyl)ethylhydroxyphosphinyl]oxy]-2-phenylethanoic acid;
2-[[(2-naphthyl)ethylhydroxyphosphinyl]oxy]-2-phenylethanoic acid;
2-[[(1-naphthyl)propylhydroxyphosphinyl]oxy]-2-phenylethanoic acid;
2-[[(2-naphthyl)propylhydroxyphosphinyl]oxy]-2-phenylethanoic acid;
2-[[(1-naphthyl)butylhydroxyphosphinyl]oxy]-2-phenylethanoic acid;
2-[[(2-naphthyl)butylhydroxyphosphinyl]oxy]-2-phenylethanoic acid;
2-[[phenylprop-2-enylhydroxyphosphinyl]oxy]-2-phenylethanoic acid;
2-[(methylhydroxyphosphinyl)oxy]hexanedioic acid;
2-[(benzylhydroxyphosphinyl)oxy]hexanedioic acid;
2-[(methylhydroxyphosphinyl)oxy]heptanedioic acid;
2-[(benzylhydroxyphosphinyl)oxy]heptanedioic acid;
2-[(methylhydroxyphosphinyl)oxy]octanedioic acid;
2-[(benzylhydroxyphosphinyl)oxy]octanedioic acid;
2-[(methylhydroxyphosphinyl)oxy]nonanedioic acid;
2-[(benzylhydroxyphosphinyl)oxy]nonanedioic acid;
2-[(methylhydroxyphosphinyl)oxy]decanedioic acid;
2-[(benzylhydroxyphosphinyl)oxy]decanedioic acid;
2-[[(benzylhydroxyphosphinyl]oxy]-2-methylethanoic acid;
2-[[benzylhydroxyphosphinyl]oxy]-2-ethylethanoic acid;
2-[[benzylhydroxyphosphinyl]oxy]-2-propylethanoic acid;
2-[[benzylhydroxyphosphinyl]oxy]-2-butylethanoic acid;
2-[[benzylhydroxyphosphinyl]oxy]-2-cyclohexylethanoic acid;
2-[[benzylhydroxyphosphinyl]oxy]-2-(cyclohexyl)methylethanoic acid;
2-[[benzylhydroxyphosphinyl]oxy]-2-phenylethanoic acid;
2-[[benzylhydroxyphosphinyl]oxy]-2-benzylethanoic acid;
2-[[benzylhydroxyphosphinyl]oxy]-2-phenylethylethanoic acid;
2-[[benzylhydroxyphosphinyl]oxy]-2-phenylpropylethanoic acid;
2-[[benzylhydroxyphosphinyl]oxy]-2-phenylbutylethanoic acid;
2-[[benzylhydroxyphosphinyl]oxy]-2-(2,3,4-trimethoxyphenyl)ethanoic acid;
2-[[benzylhydroxyphosphinyl]oxy]-2-(1-naphthyl)ethanoic acid;
2-[[benzylhydroxyphosphinyl]oxy]-2-(2-naphthyl)ethanoic acid;
2-[[benzylhydroxyphosphinyl]oxy]-2-(1-naphthyl)methylethanoic acid;
2-[[benzylhydroxyphosphinyl]oxy]-2-(2-naphthyl)methylethanoic acid;
2-[[benzylhydroxyphosphinyl]oxy]-2-(1-naphthyl)ethylethanoic acid;
2-[[benzylhydroxyphosphinyl]oxy]-2-(2-naphthyl)ethylethanoic acid;
2-[[benzylhydroxyphosphinyl]oxy]-2-(1-naphthyl)propylethanoic acid;
2-[[benzylhydroxyphosphinyl]oxy]-2-(2-naphthyl)propylethanoic acid;
2-[[benzylhydroxyphosphinyl]oxy]-2-(1-naphthyl)butylethanoic acid;
2-[[benzylhydroxyphosphinyl]oxy]-2-(2-naphthyl)butylethanoic acid;
2-[[benzylhydroxyphosphinyl]oxy]-2-phenylprop-2-enylethanoic acid;
2-[[(2-pyridyl)methylhydroxyphosphinyl]oxy]-pentanedioic acid;
2-[[(3-pyridyl)methylhydroxyphosphinyl]oxy]-pentanedioic acid;
2-[[(4-pyridyl)methylhydroxyphosphinyl]oxy]pentanedioic acid;
2-[[(3-pyridyl)ethylhydroxyphosphinyl]oxy]pentanedioic acid;
2-[[(3-pyridyl)propylhydroxyphosphinyl]oxy]pentanedioic acid;
2-[[(tetrahydrofuranyl)methylhydroxyphosphinyl]oxy] pentanedioic acid;
2-[[(tetrahydrofuranyl)ethylhydroxyphosphinyl]oxy] pentanedioic acid;
2-[[(tetrahydrofuranyl)propylhydroxyphosphinyl]oxy] pentanedioic acid;
2-[[(2-indolyl)methylhydroxyphosphinyl]oxy]pentanedioic acid;
2-[[(3-indolyl)methylhydroxyphosphinyl]oxy]pentanedioic acid;
2-[[(4-indolyl)methylhydroxyphosphinyl]oxy]pentanedioic acid;
2-[[(3-indolyl)ethylhydroxyphosphinyl]oxy]pentanedioic acid;
2-[[(3-indolyl)propylhydroxyphosphinyl]oxy]pentanedioic acid;
2-[[(2-thienyl)methylhydroxyphosphinyl]oxy]pentanedioic acid;
2-[[(3-thienyl)methylhydroxyphosphinyl]oxy]pentanedioic acid;
2-[[(4-thienyl)methylhydroxyphosphinyl]oxy]pentanedioic acid;
2-[[(3-thienyl)ethylhydroxyphosphinyl]oxy]pentanedioic acid;
2-[[(3-thienyl)propylhydroxyphosphinyl]oxy]pentanedioic acid; and
pharmaceutically acceptable salts and hydrates thereof.

In another preferred embodiment, $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl or mixtures thereof.

Exemplary compounds of this embodiment include:
2-[[(2-pyridyl)methylhydroxyphosphinyl]oxy]-2-phenylethanoic acid;
2-[[(3-pyridyl)methylhydroxyphosphinyl]oxy]-2-phenylethanoic acid;
2-[[(4-pyridyl)methylhydroxyphosphinyl]oxy]-2-phenylethanoic acid;
2-[[(3-pyridyl)ethylhydroxyphosphinyl]oxy]-2-phenylethanoic acid;
2-[[(3-pyridyl)propylhydroxyphosphinyl]oxy]-2-phenylethanoic acid;
2-[[((tetrahydrofuranyl)methylhydroxyphosphinyl]oxy]-2-phenylethanoic acid;
2-[[(tetrahydrofuranyl)ethylhydroxyphosphinyl]oxy]-2-phenylethanoic acid;
2-[[(tetrahydrofuranyl)propylhydroxyphosphinyl]oxy]-2-phenylethanoic acid;
2-[[(2-indolyl)methylhydroxyphosphinyl]oxy]-2-phenylethanoic acid;
2-[[(3-indolyl)methylhydroxyphosphinyl]oxy]-2-phenylethanoic acid;
2-[[(4-indolyl)methylhydroxyphosphinyl]oxy]-2-phenylethanoic acid;
2-[[(3-indolyl)ethylhydroxyphosphinyl]oxy]-2-phenylethanoic acid;
2-[[(3-indolyl)propylhydroxyphosphinyl]oxy]-2-phenylethanoic acid;
2-[[(2-thienyl)methylhydroxyphosphinyl]oxy]-2-phenylethanoic acid;
2-[[(3-thienyl)methylhydroxyphosphinyl]oxy]-2-phenylethanoic acid;
2-[[(4-thienyl)methylhydroxyphosphinyl]oxy]-2-phenylethanoic acid;
2-[[(3-thienyl)ethylhydroxyphosphinyl]oxy]-2-phenylethanoic acid;
2-[[(3-thienyl)propylhydroxyphosphinyl]oxy]-2-phenylethanoic acid;
2-[[benzylhydroxyphosphinyl]oxy]-2-(2-pyridyl)methylethanoic acid;
2-[[benzylhydroxyphosphinyl]oxy]-2-(3-pyridyl)methylethanoic acid;
2-[[benzylhydroxyphosphinyl]oxy]-2-(4-pyridyl)methylethanoic acid;
2-[[benzylhydroxyphosphinyl]oxy]-2-(3-pyridyl)ethylethanoic acid;
2-[[benzylhydroxyphosphinyl]oxy]-2-(3-pyridyl)propylethanoic acid;
2-[[benzylhydroxyphosphinyl]oxy]-2-(tetrahydrofuranyl)methylethanoic acid;
2-[[benzylhydroxyphosphinyl]oxy]-2-(tetrahydrofuranyl)-ethylethanoic acid;
2-[[benzylhydroxyphosphinyl]oxy]-2-(tetrahydrofuranyl)-propylethanoic acid;
2-[[benzylhydroxyphosphinyl]oxy]-2-(2-indolyl)methylethanoic acid;
2-[[benzylhydroxyphosphinyl]oxy]-2-(3-indolyl)methylethanoic acid;
2-[[benzylhydroxyphosphinyl]oxy]-2-(4-indolyl)methylethanoic acid;
2-[[benzylhydroxyphosphinyl]oxy]-2-(3-indolyl)ethylethanoic acid;
2-[[benzylhydroxyphosphinyl]oxy]-2-(3-indolyl)propylethanoic acid;
2-[[benzylhydroxyphosphinyl]oxy]-2-(2-thienyl)methylethanoic acid;
2-[[benzylhydroxyphosphinyl]oxy]-2-(3-thienyl)methylethanoic acid;
2-[[benzylhydroxyphosphinyl]oxy]-2-(4-thienyl)methylethanoic acid;
2-[[benzylhydroxyphosphinyl]oxy]-2-(3-thienyl)ethylethanoic acid;
2-[[(benzylhydroxyphosphinyl]oxy]-2-(3-thienyl)propylethanoic acid; and
pharmaceutically acceptable salts and hydrates thereof.

When Y is $NR_5$, $R_2$ is preferably substituted with carboxy. Exemplary compounds of this embodiment include:
2-[[methylhydroxyphosphinyl]amino]pentanedioic acid;
2-[[ethylhydroxyphosphinyl]amino]pentanedioic acid;
2-[[propylhydroxyphosphinyl]amino]pentanedioic acid;
2-[[butylhydroxyphosphinyl]amino]pentanedioic acid;
2-[[cyclohexylhydroxyphosphinyl]amino]pentanedioic acid;
2-[[(cyclohexyl)methylhydroxyphosphinyl]amino]pentanedioic acid;
2-[[phenylhydroxyphosphinyl]amino]pentanedioic acid;
2-[[benzylhydroxyphosphinyl]amino]pentanedioic acid;
2-[[phenylethylhydroxyphosphinyl]amino]pentanedioic acid;
2-[[phenylpropylhydroxyphosphinyl]amino]pentanedioic acid;
2-[[phenylbutylhydroxyphosphinyl]amino]pentanedioic acid;
2-[[(4-methylbenzyl)hydroxyphosphinyl]amino]pentanedioic acid;
2-[[(4-fluorobenzyl)hydroxyphosphinyl]amino]pentanedioic acid;
2-[[(2-fluorobenzyl)hydroxyphosphinyl]amino]pentanedioic acid;
2-[[(pentafluorobenzyl)hydroxyphosphinyl]amino]pentanedioic acid;
2-[[(methoxybenzyl)hydroxyphosphinyl]amino]pentanedioic acid;
2-[[(2,3,4-trimethoxyphenyl)hydroxyphosphinyl]amino]pentanedioic acid;
2-[[(1-naphthyl)hydroxyphosphinyl]amino]pentanedioic acid;
2-[[(2-naphthyl)hydroxyphosphinyl]amino]pentanedioic acid;
2-[[(1-naphthyl)methylhydroxyphosphinyl]amino]pentanedioic acid;
2-[[(2-naphthyl)methylhydroxyphosphinyl]amino]pentanedioic acid;
2-[[(1-naphthyl)ethylhydroxyphosphinyl]amino]pentanedioic acid;
2-[[(2-naphthyl)ethylhydroxyphosphinyl]amino]pentanedioic acid;
2-[[(1-naphthyl)propylhydroxyphosphinyl]amino]pentanedioic acid;
2-[[(2-naphthyl)propylhydroxyphosphinyl]amino]pentanedioic acid;
2-[[(1-naphthyl)butylhydroxyphosphinyl]amino]pentanedioic acid;
2-[[(2-naphthyl)butylhydroxyphosphinyl]amino]pentanedioic acid;
2-[[(phenylprop-2-enyl)hydroxyphosphinyl]amino]pentanedioic acid;
2-[[benzylhydroxyphosphinyl]amino]pentanedioic acid;
2-[[(2-fluorobenzyl)hydroxyphosphinyl]amino]-2-pentanedioic acid;
2-[[((hydroxy)phenylmethyl)hydroxyphosphinyl]amino]pentanedioic acid;

2-[[(3-methylbenzyl)hydroxyphosphinyl]amino]
pentanedioic acid;
2-[[(4-fluorophenyl)hydroxyphosphinyl]amino]
pentanedioic acid;
2-[(phosphono)amino]pentanedioic acid;
2-[[(3-trifluoromethylbenzyl)hydroxyphosphinyl]amino]
pentanedioic acid;
2-[(methylhydroxyphosphinyl)amino]hexanedioic acid;
2-[(benzylhydroxyphosphinyl)amino]hexanedioic acid;
2-[(methylhydroxyphosphinyl)amino]heptanedioic acid;
2-[(benzylhydroxyphosphinyl)amino]heptanedioic acid;
2-[(methylhydroxyphosphinyl)amino]octanedioic acid;
2-[(benzylhydroxyphosphinyl)amino]octanedioic acid;
2-[(methylhydroxyphosphinyl)amino]nonanedioic acid;
2-[(benzylhydroxyphosphinyl)amino]nonanedioic acid;
2-[(methylhydroxyphosphinyl)amino]decanedioic acid;
2-[(benzylhydroxyphosphinyl)amino]decanedioic acid;
3-[[(2-pyridyl)methylhydroxyphosphinyl]amino]
pentanedioic acid;
3-[[(3-pyridyl)methylhydroxyphosphinyl]amino]
pentanedioic acid;
3-[[(4-pyridyl)methylhydroxyphosphinyl]amino]
pentanedioic acid;
3-[[(3-pyridyl)ethylhydroxyphosphinyl]amino]pentanedioic
acid;
3-[[(3-pyridyl)propylhydroxyphosphinyl]amino]
pentanedioic acid;
3-[[(tetrahydrofuranyl)methylhydroxyphosphinyl]amino]
pentanedioic acid;
3-[[(tetrahydrofuranyl)ethylhydroxyphosphinyl]amino]
pentanedioic acid;
3-[[(tetrahydrofuranyl)propylhydroxyphosphinyl]amino]
pentanedioic acid;
3-[[(2-indolyl)methylhydroxyphosphinyl]amino]
pentanedioic acid;
3-[[(3-indolyl)methylhydroxyphosphinyl]amino]
pentanedioic acid;
3-[[(4-indolyl)methylhydroxyphosphinyl]amino]
pentanedioic acid;
3-[[(3-indolyl)ethylhydroxyphosphinyl]amino]pentanedioic
acid;
3-[[(3-indolyl)propylhydroxyphosphinyl]amino]
pentanedioic acid;
3-[[(2-thienyl)methylhydroxyphosphinyl]amino]
pentanedioic acid;
3-[[(3-thienyl)methylhydroxyphosphinyl]amino]
pentanedioic acid;
3-[[(4-thienyl)methylhydroxyphosphinyl]amino]
pentanedioic acid;
3-[[(3-thienyl)ethylhydroxyphosphinyl]amino]pentanedioic
acid;
3-[[(3-thienyl)propylhydroxyphosphinyl]amino]
pentanedioic acid; and
pharmaceutically acceptable salts and hydrates thereof.

In another preferred embodiment, $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl or mixtures thereof.

Exemplary compounds of this embodiment include:
2-[[methylhydroxyphosphinyl]amino]-2-phenylethanoic acid;
2-[[ethylhydroxyphosphinyl]amino]-2-phenylethanoic acid;
2-[[propylhydroxyphosphinyl]amino]-2-phenylethanoic acid;
2-[[butylhydroxyphosphinyl]amino]-2-phenylethanoic acid;
2-[[cyclohexylhydroxyphosphinyl]amino]-2-phenylethanoic acid;
2-[[(cyclohexyl)methylhydroxyphosphinyl]amino]-2-phenylethanoic acid;
2-[[phenylhydroxyphosphinyl]amino]-2-phenylethanoic acid;
2-[[benzylhydroxyphosphinyl]amino]-2-phenylethanoic acid;
2-[[phenylethylhydroxyphosphinyl]amino]-2-phenylethanoic acid;
2-[[phenylpropylhydroxyphosphinyl]amino]-2-phenylethanoic acid;
2-[[phenylbutylhydroxyphosphinyl]amino]-2-phenylethanoic acid;
2-[[(2,3,4-trimethoxyphenyl)-3-hydroxyphosphinyl]amino]-2-phenylethanoic acid;
2-[[(1-naphthyl)hydroxyphosphinyl]amino]-2-phenylethanoic acid;
2-[[(2-naphthyl)hydroxyphosphinyl]amino]-2-phenylethanoic acid;
2-[[(1-naphthyl)methylhydroxyphosphinyl]amino]-2-phenylethanoic acid;
2-[[(2-naphthyl)methylhydroxyphosphinyl]amino]-2-phenylethanoic acid;
2-[[(1-naphthyl)ethylhydroxyphosphinyl]amino]-2-phenylethanoic acid;
2-[[(2-naphthyl)ethylhydroxyphosphinyl]amino]-2-phenylethanoic acid;
2-[[(1-naphthyl)propylhydroxyphosphinyl]amino]-2-phenylethanoic acid;
2-[[(2-naphthyl)propylhydroxyphosphinyl]amino]-2-phenylethanoic acid;
2-[[(1-naphthyl)butylhydroxyphosphinyl]amino]-2-phenylethanoic acid;
2-[[(2-naphthyl)butylhydroxyphosphinyl]amino]-2-phenylethanoic acid;
2-[[phenylprop-2-enylhydroxyphosphinyl]amino]-2-phenylethanoic acid;
2-[[benzylhydroxyphosphinyl]amino]-2-methylethanoic acid;
2-[[benzylhydroxyphosphinyl]amino]-2-ethylethanoic acid;
2-[[benzylhydroxyphosphinyl]amino]-2-propylethanoic acid;
2-[[benzylhydroxyphosphinyl]amino]-2-butylethanoic acid;
2-[[benzylhydroxyphosphinyl]amino]-2-cyclohexylethanoic acid;
2-[[benzylhydroxyphosphinyl]amino]-2-(cyclohexyl)methylethanoic acid;
2-[[benzylhydroxyphosphinyl]amino]-2-phenylethanoic acid;
2-[[benzylhydroxyphosphinyl]amino]-2-benzylethanoic acid;
2-[[benzylhydroxyphosphinyl]amino]-2-phenylethylethanoic acid;
2-[[benzylhydroxyphosphinyl]amino]-2-phenylpropylethanoic acid;
2-[[benzylhydroxyphosphinyl]amino]-2-phenylbutylethanoic acid;
2-[[benzylhydroxyphosphinyl]amino]-2-(2,3,4-trimethoxyphenyl)ethanoic acid;
2-[[benzylhydroxyphosphinyl]amino]-2-(1-naphthyl)ethanoic acid;
2-[[benzylhydroxyphosphinyl]amino]-2-(2-naphthyl)ethanoic acid;
2-[[benzylhydroxyphosphinyl]amino]-2-(1-naphthyl)methylethanoic acid;

2-[[benzylhydroxyphosphinyl]amino]-2-(2-naphthyl)
methylethanoic acid;
2-[[benzylhydroxyphosphinyl]amino]-2-(1-naphthyl)
ethylethanoic acid;
2-[[benzylhydroxyphosphinyl]amino]-2-(2-naphthyl)
ethylethanoic acid;
2-[[benzylhydroxyphosphinyl]amino]-2-(1-naphthyl)
propylethanoic acid;
2-[[benzylhydroxyphosphinyl]amino]-2-(2-naphthyl)
propylethanoic acid;
2-[[benzylhydroxyphosphinyl]amino]-2-(1-naphthyl)
butylethanoic acid;
2-[[benzylhydroxyphosphinyl]amino]-2-(2-naphthyl)
butylethanoic acid;
2-[[benzylhydroxyphosphinyl]amino]-2-phenolprop-2-
enylethanoic acid;
2-[[(2-pyridyl)methylhydroxyphosphinyl]amino]-2-
phenylethanoic acid;
2-[[(3-pyridyl)methylhydroxyphosphinyl]amino]-2-
phenylethanoic acid;
2-[[(4-pyridyl)methylhydroxyphosphinyl]amino]-2-
phenylethanoic acid;
2-[[(3-pyridyl)ethylhydroxyphosphinyl]amino]-2-
phenylethanoic acid;
2-[[(3-pyridyl)propylhydroxyphosphinyl]amino]-2-
phenylethanoic acid;
2-[[(tetrahydrofuranyl)methylhydroxyphosphinyl]amino]-
2-phenylethanoic acid;
2-[[(tetrahydrofuranyl)ethylhydroxyphosphinyl]amino]-2-
phenylethanoic acid;
2-[[(tetrahydrofuranyl)propylhydroxyphosphinyl]amino]-2-
phenylethanoic acid;
2-[[(2-indolyl)methylhydroxyphosphinyl]amino]-2-
phenylethanoic acid;
2-[[(3-indolyl)methylhydroxyphosphinyl]amino]-2-
phenylethanoic acid;
2-[[(4-indolyl)methylhydroxyphosphinyl]amino]-2-
phenylethanoic acid;
2-[[(3-indolyl)ethylhydroxyphosphinyl]amino]-2-
phenylethanoic acid;
2-[[(3-indolyl)propylhydroxyphosphinyl]amino]-2-
phenylethanoic acid;
2-[[(2-thienyl)methylhydroxyphosphinyl]amino]-2-
phenylethanoic acid;
2-[[(3-thienyl)methylhydroxyphosphinyl]amino]-2
-phenylethanoic acid;
2-[[(4-thienyl)methylhydroxyphosphinyl]amino]-2-
phenylethanoic acid;
2-[[(3-thienyl)ethylhydroxyphosphinyl]amino]-2-
phenylethanoic acid;
2-[[(3-thienyl)propylhydroxyphosphinyl]amino]-2-
phenylethanoic acid;
2-[[benzylhydroxyphosphinyl]amino]-2-(2-pyridyl)
methylethanoic acid;
2-[[benzylhydroxyphosphinyl]amino]-2-(3-pyridyl)
methylethanoic acid;
2-[[benzylhydroxyphosphinyl]amino]-2-(4-pyridyl)
methylethanoic acid;
2-[[benzylhydroxyphosphinyl]amino]-2-(3-pyridyl)
ethylethanoic acid;
2-[[benzylhydroxyphosphinyl]amino]-2-(3-pyridyl)
propylethanoic acid;
2-[[benzylhydroxyphosphinyl]amino]-2-(tetrahydrofuranyl)
methylethanoic acid;
2-[[benzylhydroxyphosphinyl]amino]-2-(tetrahydrofuranyl)
ethylethanoic acid;
2-[[benzylhydroxyphosphinyl]amino]-2-(tetrahydrofuranyl)
propylethanoic acid;
2-[[benzylhydroxyphosphinyl]amino]-2-(2-indolyl)
methylethanoic acid;
2-[[benzylhydroxyphosphinyl]amino]-2-(3-indolyl)
methylethanoic acid;
2-[[benzylhydroxyphosphinyl]amino]-2-(4-indolyl)
methylethanoic acid;
2-[[benzylhydroxyphosphinyl]amino]-2-(3-indolyl)
ethylethanoic acid;
2-[[benzylhydroxyphosphinyl]amino]-2-(3-indolyl)
propylethanoic acid;
2-[[benzylhydroxyphosphinyl]amino]-2-(2-thienyl)
methylethanoic acid;
2-[[benzylhydroxyphosphinyl]amino]-2-(3-thienyl)
methylethanoic acid;
2-[[benzylhydroxyphosphinyl]amino]-2-(4-thienyl)
methylethanoic acid;
2-[[benzylhydroxyphosphinyl]amino]-2-(3-thienyl)
ethylethanoic acid;
2-[[benzylhydroxyphosphinyl]amino]-2-(3-thienyl)
propylethanoic acid; and
pharmaceutically acceptable salts and hydrates thereof.

Another preferred NAALADase inhibitor is a compound of Formula II:

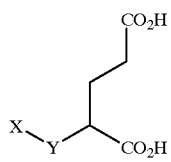

II or a pharmaceutically acceptable salt or hydrate thereof, wherein:

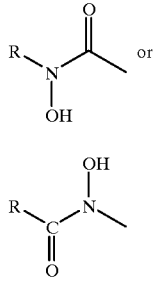

III

IV

Y is $CR_1R_2$, $NR_3$ or O;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, Ar and mixtures thereof, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar or a mixture thereof; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino or a mixture thereof.

In a preferred embodiment, Y is $CH_2$.

In a more preferred embodiment, R is selected from the group consisting of hydrogen, $C_1$–$C_4$ straight or branched chain alkyl, 4-pyridyl, benzyl and phenyl, said R having one to three substituent(s) independently selected from the group consisting of hydrogen, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar and mixtures thereof.

In the most preferred embodiment, the compound is selected from the group consisting of:
2-[[(N-hydroxy)carbamoyl]methyl]pentanedioic acid;
2-[[(N-hydroxy-N-methyl)carbamoyl]methyl]pentanedioic acid;
2-[[(N-butyl-N-hydroxy)carbamoyl]methyl]pentanedioic acid;
2-[[(N-benzyl-N-hydroxy)carbamoyl]methyl]pentanedioic acid;
2-[[(N-hydroxy-N-phenyl)carbamoyl]methyl]pentanedioic acid;
2-[[(N-hydroxy-N-2-phenylethyl)carbamoyl]methyl] pentanedioic acid;
2-[[(N-ethyl-N-hydroxy)carbamoyl]methyl]pentanedioic acid;
2-[[(N-hydroxy-N-propyl)carbamoyl]methyl]pentanedioic acid;
2-[[(N-hydroxy-N-3-phenylpropyl)carbamoyl]methyl] pentanedioic acid;
2-[[(N-hydroxy-N-4-pyridyl)carbamoyl]methyl] pentanedioic acid;
2-[[(N-hydroxy)carboxamido]methyl]pentanedioic acid;
2-[[N-hydroxy(methyl)carboxamido]methyl]pentanedioic acid;
2-[[N-hydroxy(benzyl)carboxamido]methyl]pentanedioic acid;
2-[[N-hydroxy(phenyl)carboxamido]methyl]pentanedioic acid;
2-[[N-hydroxy(2-phenylethyl)carboxamido]methyl] pentanedioic acid;
2-[[N-hydroxy(ethyl)carboxamido]methyl]pentanedioic acid;
2-[[N-hydroxy(propyl)carboxamido]methyl]pentanedioic acid;
2-[[N-hydroxy(3-phenylpropyl)carboxamido]methyl] pentanedioic acid; and
2-[[N-hydroxy(4-pyridyl)carboxamido]methyl] pentanedioic acid.

Another preferred NAALADase inhibitor is a compound of Formula V:

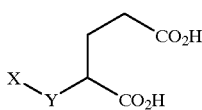

V or a pharmaceutically acceptable salt or hydrate thereof, wherein:

X is selected from the group consisting of

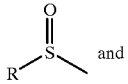

VI

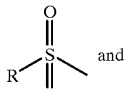

VII

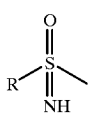

VIII

Y is $CR_1R_2$, $NR_3$ or O;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar or a mixture thereof; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, said Ar having one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino and mixtures thereof.

In a preferred embodiment, at least one of said R, $R_1$, $R_2$ and $R_3$ is/are independently substituted with $C_3$–$C_8$ cycloalkyl, $C_5$–$C_7$ cycloalkenyl, hydroxy, halo, nitro, trifluoromethyl, $C_2$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or a mixture thereof.

In a more preferred embodiment, Y is $CH_2$.

In an even more preferred embodiment, R is selected from the group consisting of hydrogen, $C_1$–$C_4$ straight or branched chain alkyl, 4-pyridyl, benzyl and phenyl, said R having one to three substituent(s) independently selected from the group consisting of hydrogen, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar and mixtures thereof.

In the most preferred embodiment, the compound is selected from the group consisting of:
2-[(sulfinyl)methyl]pentanedioic acid;
2-[(methylsulfinyl)methyl]pentanedioic acid;
2-[(ethylsulfinyl)methyl]pentanedioic acid;
2-[(propylsulfinyl)methyl]pentanedioic acid;
2-[(butylsulfinyl)methyl]pentanedioic acid;
2-[(phenylsulfinyl)methyl]pentanedioic acid;
2-[[(2-phenylethyl)sulfinyl]methyl]pentanedioic acid;
2-[[(3-phenylpropyl)sulfinyl]methyl]pentanedioic acid;

2-[[(4-pyridyl)sulfinyl]methyl]pentanedioic acid;
2-[(benzylsulfinyl)methyl]pentanedioic acid;
2-[(sulfonyl)methyl]pentanedioic acid;
2-[(methylsulfonyl)methyl]pentanedioic acid;
2-[(ethylsulfonyl)methyl]pentanedioic acid;
2-[(propylsulfonyl)methyl]pentanedioic acid;
2-[(butylsulfonyl)methyl]pentanedioic acid;
2-[(phenylsulfonyl)methyl]pentanedioic acid;
2-[[(2-phenylethyl)sulfonyl]methyl]pentanedioic acid;
2-[[(3-phenylpropyl)sulfonyl]methyl]pentanedioic acid;
2-[[(4-pyridyl)sulfonyl]methyl]pentanedioic acid; and
2-[(benzylsulfonyl)methyl]pentanedioic acid;
2-[(sulfoximinyl)methyl]pentanedioic acid;
2-[(methylsulfoximinyl)methyl]pentanedioic acid;
2-[(ethylsulfoximinyl)methyl]pentanedioic acid;
2-[(propylsulfoximinyl)methyl]pentanedioic acid;
2-[(butylsulfoximinyl)methyl]pentanedioic acid;
2-[(phenylsulfoximinyl)methyl]pentanedioic acid;
2-[[(2-phenylethyl)sulfoximinyl]methyl]pentanedioic acid;
2-[[(3-phenylpropyl)sulfoximinyl]methyl]pentanedioic acid;
2-[[(4-pyridyl)sulfoximinyl]methyl]pentanedioic acid; and
2-[(benzylsulfoximinyl)methyl]pentanedioic acid.

Another preferred NAALADase inhibitor is a compound of Formula IX:

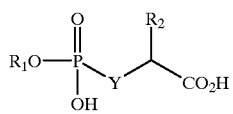

or a pharmaceutically acceptable salt or hydrate thereof, wherein:

Y is $CR_3R_4$, $NR_5$ or O;

$R_2$ is selected from the group consisting of hydrogen, $C_1-C_9$ straight or branched chain alkyl, $C_2-C_9$ straight or branched chain alkenyl, $C_3-C_8$ cycloalkyl, $C_5-C_7$ cycloalkenyl and Ar, wherein said $R_2$ is unsubstituted or substituted with carboxy, $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_9$ alkoxy, $C_2-C_9$ alkenyloxy, phenoxy, benzyloxy, amino, Ar or a mixture thereof;

$R_1$, $R_3$, $R_4$ and $R_5$ are independently selected from the group consisting of hydrogen, $C_1-C_9$ straight or branched chain alkyl, $C_2-C_9$ straight or branched chain alkenyl, $C_3-C_8$ cycloalkyl, $C_5-C_7$ cycloalkenyl and Ar, wherein said R, $R_1$, $R_2$ and $R_3$ are independently unsubstituted or substituted with $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_9$ alkoxy, $C_2-C_9$ alkenyloxy, phenoxy, benzyloxy, amino, Ar or a mixture thereof; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1-C_6$ straight or branched chain alkyl, $C_2-C_6$ straight or branched chain alkenyl, $C_1-C_6$ alkoxy, $C_2-C_6$ alkenyloxy, phenoxy, benzyloxy, amino and mixtures thereof.

In a preferred embodiment, Y is $CH_2$.

When R is hydrogen, the compound is preferably selected from the group consisting of:

phosphonopropanoic acid;
2-methyl-3-phosphonopropanoic acid;
2-ethyl-3-phosphonopropanoic acid;
2-propyl-3-phosphonopropanoic acid;
2-butyl-3-phosphonopropanoic acid;
2-phenyl-3-phosphonopropanoic acid;
2-(2-phenylethyl)-3-phosphonopropanoic acid;
2-(3-phenylpropyl)-3-phosphonopropanoic acid;
2-(4-pyridyl)-3-phosphonopropanoic acid; and
2-benzyl-3- phosphonopropanoic acid.

When $R_2$ is substituted with carboxy, the compound is selected from the group consisting of:
2-(hydrohydroxyphosphonomethyl)pentanedioic acid;
2-(hydromethoxyphosphonomethyl)pentanedioic acid;
2-(hydroethoxyphosphonomethyl)pentanedioic acid;
2-(hydropropoxyphosphonomethyl)pentanedioic acid;
2-(hydrobutoxyphosphonomethyl)pentanedioic acid;
2-(hydrophenoxyphosphonomethyl)pentanedioic acid;
2-[hydro(2-phenylethoxy)phosphonomethyl]pentanedioic acid;
2-[hydro(3-phenylpropoxy)phosphonomethyl]pentanedioic acid;
2-[hydro(4-pyridyloxy)phosphonomethyl]pentanedioic acid; and
2-(hydrobenzyloxyphosphonomethyl)pentanedioic acid.

Another preferred NAALADase inhibitor is a compound of Formula X:

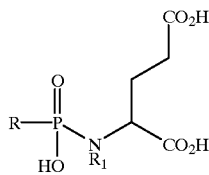

or a pharmaceutically acceptable salt or hydrate thereof, wherein:

R and $R_1$ are independently selected from the group consisting of hydrogen, $C_1-C_9$ straight or branched chain alkyl or alkenyl group, $C_3-C_8$ cycloalkyl, $C_3$ or $C_5$ cycloalkyl, $C_5-C_7$ cycloalkenyl and Ar, wherein said R and $R_1$ are independently unsubstituted or substituted with $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_9$ alkoxy, $C_2-C_9$ alkenyloxy, phenoxy, benzyloxy, amino, Ar or a mixture thereof; and Ar is selected from the group consisting of 1-napthyl, 2-napthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1-C_6$ straight or branched alkyl, $C_2-C_6$ straight or branched chain alkenyl, $C_1-C_6$ alkoxy, $C_2-C_6$ alkenyloxy, phenoxy, benzyloxy, amino or a mixture thereof.

In a preferred embodiment, the compound is selected from the group consisting of:
N-[methylhydroxyphosphinyl]glutamic acid;
N-[ethylhydroxyphosphinyl]glutamic acid;
N-[propylhydroxyphosphinyl]glutamic acid;
N-[butylhydroxyphosphinyl]glutamic acid;
N-[phenylhydroxyphosphinyl]glutamic acid;

N-[(phenylmethyl)hydroxyphosphinyl]glutamic acid;
N-[((2-phenylethyl)methyl)hydroxyphosphinyl]glutamic acid; and
N-methyl-N-[phenylhydroxyphosphinyl]glutamic acid.

Another preferred NAALADase inhibitor is a compound of Formula XI:

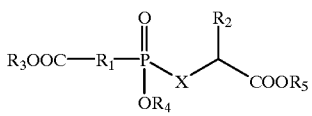

XI or a pharmaceutically acceptable salt, hydrate or prodrug thereof, wherein:

X is $CR_6R_7$, O or $NR_8$;

$R_1$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$ is unsubstituted or substituted with one or more substituent(s) independently selected from the group consisting of carboxy, carbonyl, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar;

$R_2$, $R_3$, $R_4$, $R_5$, $R_6$, $R_7$, and $R_8$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$, $R_3$, $R_4$, $R_5$, $R_6$, $R_7$, and $R_8$ are independently unsubstituted or substituted with one or more substituent(s) independently selected from the group consisting of carboxy, carbonyl, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with one or more substituent(s) independently selected from the group consisting of carboxy, carbonyl, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, and amino.

In a preferred embodiment, X is $CH_2$.

In a more preferred embodiment, $R_2$ is —$(CH_2)_2COOR_9$; and $R_9$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_9$ is unsubstituted or substituted with one or more substituent(s) independently selected from the group consisting of carboxy, carbonyl, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar.

In the most preferred embodiment, $R_3$, $R_4$, $R_5$, and $R_9$ are hydrogen.

Preferred compounds of Formula XI are selected from the group consisting of:
2-[[(2-carboxypropyl)hydroxyphosphinyl]methyl]pentanedioic acid;
2-[[(2-carboxybutyl)hydroxyphosphinyl]methyl]pentanedioic acid;
2-[[(2-carboxypentyl)hydroxyphosphinyl]methyl]pentanedioic acid;
2-[[(2-carboxy-3-phenylpropyl)hydroxyphosphinyl]methyl]-pentanedioic acid;
2-[[(2-carboxy-3-naphthylpropyl)hydroxyphosphinyl]methyl]pentanedioic acid;
2-[[(2-carboxy-3-pyridylpropyl)hydroxyphosphinyl]methyl]-pentanedioic acid;
2-[[(2-benzyloxycarbonyl)-3-phenylpropyl)hydroxyphosphinyl]methyl]pentanedioic acid;
2-[[(2-methoxycarbonyl)-3-phenylpropyl)hydroxyphosphinyl]methyl]pentanedioic acid;
2-[[(3-carboxy-2-methoxycarbonyl)propyl)hydroxyphosphinyl]methyl]pentanedioic acid;
2-[[(4-carboxy-2-methoxycarbonyl)butyl)hydroxyphosphinyl]methyl]pentanedioic acid; and
pharmaceutically acceptable salts, hydrates and prodrugs thereof.

The most preferred compound of Formula XI is 2-[[(2-carboxypropyl)hydroxyphosphinyl]methyl]pentanedioic acid, or a pharmaceutically acceptable salt, hydrate or prodrug thereof.

The compounds of Formula XI possess one or more asymmetric center(s) and thus can be produced as mixtures (racemic and non-racemic) of stereoisomers, or as individual R- and S-stereoisomers. The individual stereoisomers may be obtained by using an optically active starting material, by resolving a racemic or non-racemic mixture of an intermediate at some appropriate stage of synthesis, or by resolving a compound of Formula XI.

Another preferred NAALADase inhibitor is a compound of Formula XII:

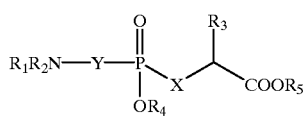

XII or a pharmaceutically acceptable salt, hydrate, or prodrug thereof, wherein:

X is $CR_6R_7$, O, or $NR_8$;

Y is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_1$, wherein Y is unsubstituted or substituted with one or more substituent(s);

$R_1$ and $R_2$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_2$, carboxy, carbonyl, sulfonyl, formanilido, and thioformamido, wherein $R_1$ and $R_2$ are independently unsubstituted or substituted with one or more substituent(s); or $R_1$ and $R_2$ are taken together, with the nitrogen atom to which they are attached, to form a 5–7 membered azaheterocyclic ring, wherein said azaheterocyclic ring contains one or more heteroatom(s) independently selected from the group consisting of N, O, and S, and said azaheterocyclic ring is unsubstituted or substituted with one or more substituent(s);

$R_3$, $R_4$, $R_5$, $R_6$, $R_7$, and $R_8$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, and $Ar_3$, wherein $R_3$, $R_4$, $R_5$, $R_6$, $R_7$, and $R_8$ are independently unsubstituted or substituted with one or more substituent(s); and $Ar_1$, $Ar_2$, and $Ar_3$ are independently a carbocyclic or heterocyclic moiety, which is unsubstituted or substituted with one or more substituent(s).

Possible substituents of Y, $R_1$, $R_2$, $R_3$, $R_4$, $R_5$, $R_6$, $R_7$, $R_8$, $Ar_1$, $Ar_2$, and $Ar_3$ include, without limitation, $C_1$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment of the compound of Formula XII, X is $CH_2$. When X is $CH_2$ and Y is an unsubstituted or a monosubstituted $CH_2$, $R_1$ is preferably $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_2$, wherein $R_1$ is unsubstituted or substituted with one or more substituent(s).

In another preferred embodiment, $R_3$ is —$(CH_2)_2COOR_9$; $R_9$ is hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_4$, wherein $R_9$ is unsubstituted or substituted with one or more substituent(s); and $Ar_4$ is a carbocyclic or heterocyclic moiety which is unsubstituted or substituted with one or more substituent(s) More preferably, $R_3$ is $(CH_2)_2COOH$.

In other preferred embodiments, $R_4$ is hydrogen and $R_5$ is hydrogen.

More preferably, X is $CH_2$, $R_3$ is $(CH_2)_2COOH$, $R_4$ is hydrogen, and $R_5$ is hydrogen.

In the most preferred embodiment, X is $CH_2$, $R_3$ is $(CH_2)_2COOH$, $R_4$ is hydrogen, $R_5$ is hydrogen, and $R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_2$, carboxy, carbonyl, sulfonyl, formanilido, or thioformamido, wherein $R_1$ is unsubstituted or substituted with one or more substituent(s).

Exemplary compounds of Formula XII include without limitation:

2-[({[Benzylamino]benzyl}(hydroxyphosphinyl))methyl]pentanedioic acid;

2-[({[Carboxyamino]benzyl}(hydroxyphosphinyl))methyl]pentanedioic acid;

2-[({[Acetylamino]benzyl}(hydroxyphosphinyl))methyl]pentanedioic acid;

2-[({[Dibenzylamino]benzyl}(hydroxyphosphinyl))methyl]pentanedioic acid;

2-[({[Phenylamino]benzyl}(hydroxyphosphinyl))methyl]pentanedioic acid;

2-({[(Phenylcarbonylamino)benzyl](hydroxyphosphinyl)}methyl)pentanedioic acid;

2-({[(Phenylsulfonylamino)benzyl](hydroxyphosphinyl)}methyl)pentanedioic acid;

2-[({[(2-Fluorophenyl)amino]benzyl}(hydroxyphosphinyl))methyl]pentanedioic acid;

2-[({[(3-Fluorophenyl)amino]benzyl}(hydroxyphosphinyl))methyl]pentanedioic acid;

2-[({[(4-Fluorophenyl)amino]benzyl}(hydroxyphosphinyl))methyl]pentanedioic acid;

2-[({[(2-Chlorophenyl)amino]benzyl}(hydroxyphosphinyl))methyl]pentanedioic acid;

2-[({[(3-Chlorophenyl)amino]benzyl}(hydroxyphosphinyl))methyl]pentanedioic acid;

2-[({[(4-Chlorophenyl)amino]benzyl}(hydroxyphosphinyl))methyl]pentanedioic acid;

2-[({[(2-Methoxyphenyl)amino]benzyl}(hydroxyphosphinyl))methyl]pentanedioic acid;

2-[({[(3-Methoxyphenyl)amino]benzyl}(hydroxyphosphinyl))methyl]pentanedioic acid;

2-[({[(4-Methoxyphenyl)amino]benzyl}(hydroxyphosphinyl))methyl]pentanedioic acid;

2-[({[(2-Hydroxyphenyl)amino]benzyl}(hydroxyphosphinyl))methyl]pentanedioic acid;

2-[({[(3-Hydroxyphenyl)amino]benzyl}(hydroxyphosphinyl))methyl]pentanedioic acid;

2-[({[(4-Hydroxyphenyl)amino]benzyl}(hydroxyphosphinyl))methyl]pentanedioic acid;

2-[({[(2-Carboxyphenyl)amino]benzyl}(hydroxyphosphinyl))methyl]pentanedioic acid;

2-[({[(3-Carboxyphenyl)amino]benzyl}(hydroxyphosphinyl))methyl]pentanedioic acid;

2-[({[(4-Carboxyphenyl)amino]benzyl}(hydroxyphosphinyl))methyl]pentanedioic acid;

2-[({[(2-Nitrophenyl)amino]benzyl}(hydroxyphosphinyl))methyl]pentanedioic acid;

2-[({[(3-Nitrophenyl)amino]benzyl}(hydroxyphosphinyl))methyl]pentanedioic acid;

2-[({[(4-Nitrophenyl)amino]benzyl}(hydroxyphosphinyl))methyl]pentanedioic acid;

2-[({[(2-Sulfonylphenyl)amino]benzyl}(hydroxyphosphinyl))methyl]pentanedioic acid;

2-[({[(3-Sulfonylphenyl)amino]benzyl}(hydroxyphosphinyl))methyl]pentanedioic acid;

2-[({[(4-Sulfonylphenyl)amino]benzyl}(hydroxyphosphinyl))methyl]pentanedioic acid;

2-[({[(2-Methylphenyl)amino]benzyl}(hydroxyphosphinyl))methyl]pentanedioic acid;

2-[({[(3-Methylphenyl)amino]benzyl}(hydroxyphosphinyl))methyl]pentanedioic acid;

2-[({[(4-Methylphenyl)amino]benzyl}(hydroxyphosphinyl))methyl]pentanedioic acid;

2-[({[(2-Tert-butylphenyl)amino]benzyl}(hydroxyphosphinyl))methyl]pentanedioic acid;

2-[({[(3-Tert-butylphenyl)amino]benzyl}(hydroxyphosphinyl))methyl]pentanedioic acid;

2-[({[(4-Tert-butylphenyl)amino]benzyl}(hydroxyphosphinyl))methyl]pentanedioic acid;

2-[({[(2-Trifluoromethylphenyl)amino]benzyl}(hydroxyphosphinyl))methyl]pentanedioic acid;

2-[({[(3-Trifluoromethylphenyl)amino]benzyl}(hydroxyphosphinyl))methyl]pentanedioic acid;

2-[({[(4-Trifluoromethylphenyl)amino]benzyl}(hydroxyphosphinyl))methyl]pentanedioic acid;
2-[({[(Thioformanilido)amino]benzyl}(hydroxyphosphinyl))methyl]pentanedioic acid;
2-[({[1,3-Dioxo-2,3-dihydro-1H-2-isoindolyl]benzyl}-hydroxyphosphinyl)methyl]pentanedioic acid;
2-[({[Benzylamino]methyl}(hydroxyphosphinyl))methyl]pentanedioic acid;
2-[({[Carboxyamino]methyl}(hydroxyphosphinyl))methyl]pentanedioic acid;
2-[({[Acetylamino]methyl}(hydroxyphosphinyl))methyl]pentanedioic acid;
2-[({[Diphenylamino]methyl}(hydroxyphosphinyl))methyl]pentanedioic acid;
2-[({[Phenylamino]methyl}(hydroxyphosphinyl))methyl]pentanedioic acid;
2-({[(Phenylcarbonylamino)methyl](hydroxyphosphinyl)}methyl)pentanedioic acid;
2-({[(Phenylsulfonylamino)methyl](hydroxyphosphinyl)}methyl)pentanedioic acid;
2-[({[(2-Fluorophenyl)amino]methyl}(hydroxyphosphinyl))methyl]pentanedioic acid;
2-[({[(3-Fluorophenyl)amino]methyl}(hydroxyphosphinyl))methyl]pentanedioic acid;
2-[({[(4-Fluorophenyl)amino]methyl}(hydroxyphosphinyl))methyl]pentanedioic acid;
2-[({[(2-Chlorophenyl)amino]methyl}(hydroxyphosphinyl))methyl]pentanedioic acid;
2-[({[(3-Chlorophenyl)amino]methyl}(hydroxyphosphinyl))methyl]pentanedioic acid;
2-[({[(4-Chlorophenyl)amino]methyl}(hydroxyphosphinyl))methyl]pentanedioic acid;
2-[({[(2-Methoxyphenyl)amino]methyl}(hydroxyphosphinyl))methyl]pentanedioic acid;
2-[({[(3-Methoxyphenyl)amino]methyl}(hydroxyphosphinyl))methyl]pentanedioic acid;
2-[({[(4-Methoxyphenyl)amino]methyl}(hydroxyphosphinyl))methyl]pentanedioic acid;
2-[({[(2-Hydroxyphenyl)amino]methyl}(hydroxyphosphinyl))methyl]pentanedioic acid;
2-[({[(3-Hydroxyphenyl)amino]methyl}(hydroxyphosphinyl))methyl]pentanedioic acid;
2-[({[(4-Hydroxyphenyl)amino]methyl}(hydroxyphosphinyl))methyl]pentanedioic acid;
2-[({[(2-Carboxyphenyl)amino]methyl}(hydroxyphosphinyl))methyl]pentanedioic acid;
2-[({[(3-Carboxyphenyl)amino]methyl}(hydroxyphosphinyl))methyl]pentanedioic acid;
2-[({[(4-Carboxyphenyl)amino]methyl}(hydroxyphosphinyl))methyl]pentanedioic acid;
2-[({[(2-Nitrophenyl)amino]methyl}(hydroxyphosphinyl))methyl]pentanedioic acid;
2-[({[(3-Nitrophenyl)amino]methyl}(hydroxyphosphinyl))methyl]pentanedioic acid;
2-[({[(4-Nitrophenyl)amino]methyl}(hydroxyphosphinyl))methyl]pentanedioic acid;
2-[({[(2-Sulfonylphenyl)amino]methyl}(hydroxyphosphinyl))methyl]pentanedioic acid;
2-[({[(3-Sulfonylphenyl)amino]methyl}(hydroxyphosphinyl))methyl]pentanedioic acid;
2-[({[(4-Sulfonylphenyl)amino]methyl}(hydroxyphosphinyl))methyl]pentanedioic acid;
2-[({[(2-Methylphenyl)amino]methyl}(hydroxyphosphinyl))methyl]pentanedioic acid;
2-[({[(3-Methylphenyl)amino]methyl}(hydroxyphosphinyl))methyl]pentanedioic acid;
2-[({[(4-Methylphenyl)amino]methyl}(hydroxyphosphinyl))methyl]pentanedioic acid;
2-[({[(2-Tert-butylphenyl)amino]methyl}(hydroxyphosphinyl))methyl]pentanedioic acid;
2-[({[(3-Tert-butylphenyl)amino]methyl}(hydroxyphosphinyl))methyl]pentanedioic acid;
2-[({[(4-Tert-butylphenyl)amino]methyl}(hydroxyphosphinyl))methyl]pentanedioic acid;
2-[({[(2-Trifluoromethylphenyl)amino]methyl}(hydroxyphosphinyl))methyl]pentanedioic acid;
2-[({[(3-Trifluoromethylphenyl)amino]methyl}(hydroxyphosphinyl))methyl]pentanedioic acid;
2-[({[(4-Trifluoromethylphenyl)amino]methyl}(hydroxyphosphinyl))methyl]pentanedioic acid;
2-[({[(Thioformanilido)amino]benzyl}(hydroxyphosphinyl))methyl]pentanedioic acid;
2-[({[1,3-Dioxo-2,3-dihydro-1H-2-isoindolyl]methyl}hydroxyphosphinyl)methyl]pentanedioic acid; and pharmaceutically acceptable salts, hydrates and prodrugs thereof.

The most preferred compounds of Formula XII are selected from the group consisting of:

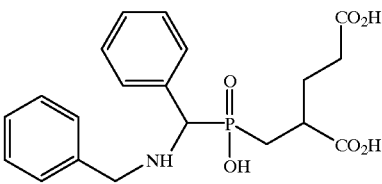

2-[({[Benzylamino]benzyl}(hydroxyphosphinyl))methyl]pentanedioic acid (1);

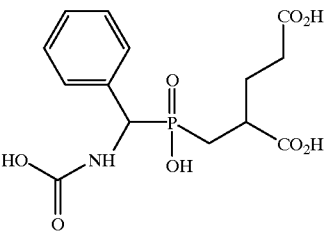

2-[({[Carboxyamino]benzyl}(hydroxyphosphinyl))methyl]pentanedioic acid (2);

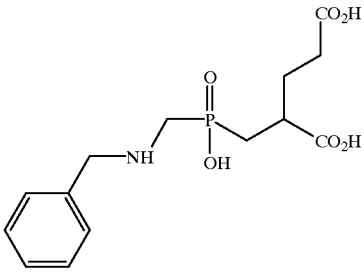

2-[({[Benzylamino]methyl}(hydroxyphosphinyl))methyl]
pentanedioic acid (15);

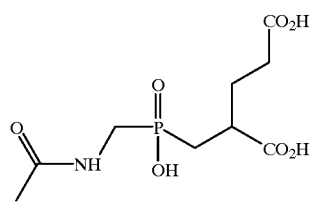

2-[({[Acetylamino]methyl}(hydroxyphosphinyl))methyl]
pentanedioic acid (4);

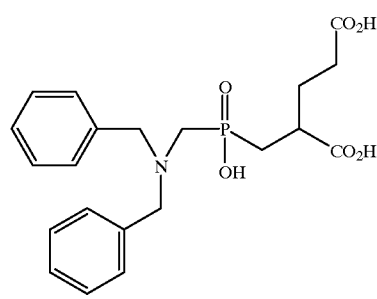

2-[({[Diphenylamino]methyl}(hydroxyphosphinyl))
methyl]pentanedioic acid (5);

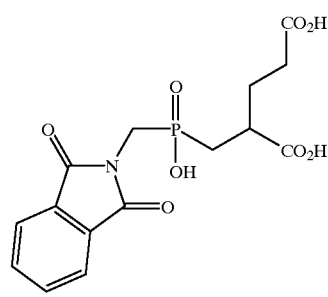

2-[({[1,3-Dioxo-2,3-dihydro-1H-2-isoindolyl]
methyl}hydroxyphosphinyl)methyl]pentanedioic acid
(6);

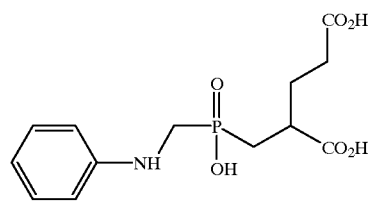

2-[({[Phenylamino]methyl}(hydroxyphosphinyl))methyl]
pentanedioic acid (7);

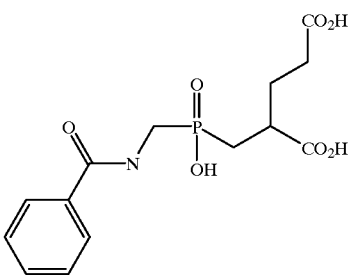

2-({[(Phenylcarbonylamino)methyl](hydroxyphosphinyl)
}methyl)pentanedioic acid (8);

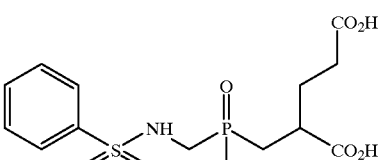

2-({[(Phenylsulfonylamino)methyl](hydroxyphosphinyl)
}methyl)pentanedioic acid (9);

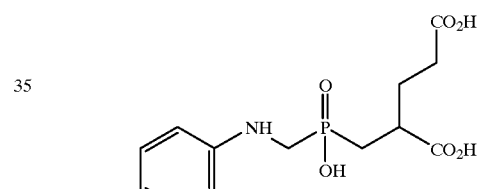

2-[({[(4-Fluorophenyl)amino]methyl}
(hydroxyphosphinyl))methyl]pentanedioic acid (10);

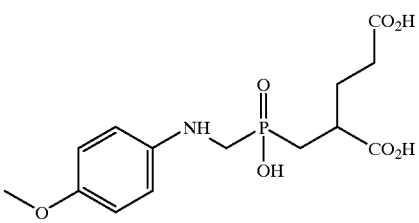

2-[({[(4-Methoxyphenyl)amino]methyl}
(hydroxyphosphinyl))methyl]pentanedioic acid (11);

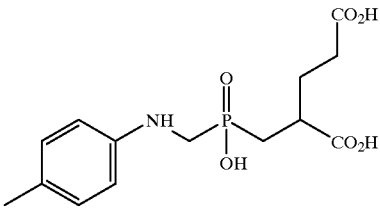

2-[({[(4-Methylphenyl)amino]methyl}
(hydroxyphosphinyl))-methyl]pentanedioic acid (12);

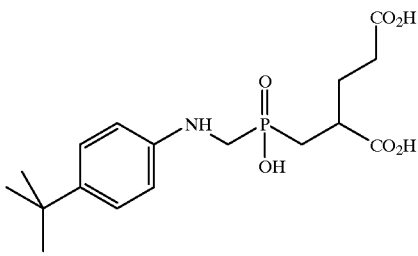

2-[({[(4-Tert-butylphenyl)amino]methyl}
(hydroxyphosphinyl))methyl]pentanedioic acid (13); and

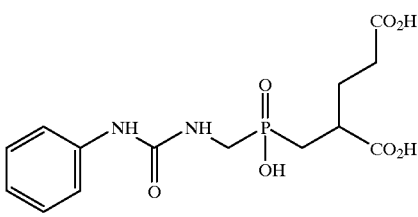

2-[({[(Thioformanilido)amino]benzyl}
(hydroxyphosphinyl))-methyl]pentanedioic acid (14).

Another preferred NAALADase inhibitor is a compound of Formula XIII:

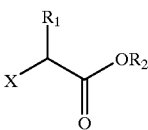

XIII or a pharmaceutically acceptable salt, hydrate, metabolite, or prodrug thereof, wherein:

X is a moiety of formula II, III, IV, V or VI

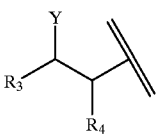

XIV

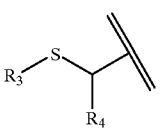

XV

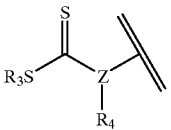

XVI

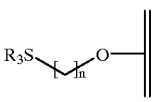

XVII

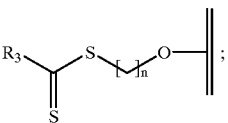

XVIII n is 1, 2, 3 or 4;

Y is $SR_5$, $SO_3R_5$, $SO_2R_5$, $SOR_5$, $SO(NR_5)R_6$ or $S(N_2R_5R_6)R_7$;

Z is N or $CR_8$;

R, $R_1$, $R_2$, $R_3$, $R_4$, $R_5$, $R_6$, $R_7$ and $R_8$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said alkyl, alkenyl, cycloalkyl, cycloalkenyl and $Ar_1$ are independently unsubstituted or substituted with one or more substituent(s); and $Ar_1$ is a carbocyclic or heterocyclic moiety, which is unsubstituted or substituted with one or more substituent(s);

provided that when X is a moiety of Formula XV, $R_1$ is $(CH_2)_2COOR$ or $(CH_2)_2CONHR$, and $R_4$ is hydrogen, then $R_3$ is not hydrogen or COR; and when X is a moiety of Formula XVI, Z is N and $R_1$ is $(CH_2)_2COOH$, then $R_4$ is not hydrogen.

Examples of useful alkyl groups include, without limitation, methyl, ethyl, propyl, isopropyl, butyl, tert-butyl, n-pentyl, 2-methyl pentyl and the like.

Possible substituents of said alkenyl, cycloalkyl, cycloalkenyl, and $Ar_1$ include, without limitation, $C_1$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

In a preferred embodiment, $R_1$ is —$(CH_2)_2COOR_9$; $R_9$ is hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_2$, wherein $R_9$ is unsubstituted or substituted with one or more substituent(s); and $Ar_2$ is a carbocyclic or heterocyclic moiety which is unsubstituted or substituted with one or more substituent(s).

In a more preferred embodiment, $R_1$ is $(CH_2)_2COOH$; and $R_2$ is hydrogen.

Preferred compounds of Formula XIII wherein X is a moiety of Formula XIV, $R_1$ is $(CH_2)_2COOH$, and $R_2$ is hydrogen, include:
2-(2-sulfanylethyl)pentanedioic acid;
2-(2-sulfanylpropyl)pentanedioic acid;
2-(2-sulfanylbutyl)pentanedioic acid;
2-(2-phenyl-2-sulfanylethyl)pentanedioic acid;
2-(2-(4-pyridyl)-2-sulfanylethyl)pentanedioic acid;
2-(1-methyl-2-sulfanylethyl)pentanedioic acid;
2-(1-benzyl-2-sulfanylethyl)pentanedioic acid;
2-(1-methyl-2-sulfanylpropyl)pentanedioic acid;
2-(1-ethyl-2-sulfanylpropyl)pentanedioic acid;
2-(1-propyl-2-sulfanylpropyl)pentanedioic acid;
2-(1-butyl-2-sulfanylpropyl)pentanedioic acid;
2-(2-sulfoethyl)pentanedioic acid;
2-[2-(methylsulfonyl)ethyl]pentanedioic acid;
2-[2-(ethylsulfonyl)ethyl]pentanedioic acid;
2-[2-(propylsulfonyl)ethyl]pentanedioic acid;
2-[2-(butylsulfonyl)ethyl]pentanedioic acid;
2-[2-(methylsulfanyl)-3-phenylpropyl]pentanedioic acid;
2-[2-(ethylsulfanyl)-3-phenylpropyl]pentanedioic acid;
2-[2-(propylsulfanyl)-3-phenylpropyl]pentanedioic acid;
2-[2-(butylsulfanyl)-3-phenylpropyl]pentanedioic acid;
2-[2-(methylsulfanyl)-3-(4-pyridyl)propyl]pentanedioic acid;
2-[2-(ethylsulfanyl)-3-(4-pyridyl)propyl]pentanedioic acid;
2-[2-(propylsulfanyl)-3-(4-pyridyl)propyl]pentanedioic acid;
2-[2-(butylsulfanyl)-3-(4-pyridyl)propyl]pentanedioic acid;
2-[1-benzyl-2-(methylsulfonyl)ethyl]pentanedioic acid;
2-[1-phenyl-2-(methylsulfonyl)ethyl]pentanedioic acid;
2-[1-(4-pyridyl)-2-(methylsulfonyl)ethyl]pentanedioic acid;
2-[1-benzyl-2-(ethylsulfonyl)ethyl]pentanedioic acid;
2-[1-phenyl-2-(ethylsulfonyl)ethyl]pentanedioic acid;
2-[1-(4-pyridyl)-2-(ethylsulfonyl)ethyl]pentanedioic acid;
2-(1-benzyl-2-sulfoethyl)pentanedioic acid;
2-(1-phenyl-2-sulfoethyl)pentanedioic acid;
2-(1-(4-pyridyl)-2-sulfoethyl)pentanedioic acid;
2-(1-methyl-2-sulfopropyl)pentanedioic acid;
2-(1-ethyl-2-sulfopropyl)pentanedioic acid;
2-(1-propyl-2-sulfopropyl)pentanedioic acid;
2-(1-butyl-2-sulfopropyl)pentanedioic acid;
2-(1-benzyl-2-sulfobutyl)pentanedioic acid;
2-(1-phenyl-2-sulfobutyl)pentanedioic acid;
2-(1-(4-pyridyl)-2-sulfobutyl)pentanedioic acid;
2-[2-(methylsulfonyl)-1-phenylethyl]pentanedioic acid;
2-[2-(ethylsulfonyl)-1-phenylethyl]pentanedioic acid;
2-[2-(propylsulfonyl)-1-phenylethyl]pentanedioic acid;
2-[2-(butylsulfonyl)-1-phenylethyl]pentanedioic acid;
2-[2-(methylsulfonyl)-1-(4-pyridyl)ethyl]pentanedioic acid;
2-[2-(ethylsulfonyl)-1-(4-pyridyl)ethyl]pentanedioic acid;
2-[2-(propylsulfonyl)-1-(4-pyridyl)ethyl]pentanedioic acid;
2-[2-(butylsulfonyl)-1-(4-pyridyl)ethyl]pentanedioic acid;
2-[1-(sulfomethyl)propyl]pentanedioic acid;
2-[1-(sulfomethyl)butyl]pentanedioic acid;
2-(1-phenyl-2-sulfopropyl)pentanedioic acid;
2-(1-(4-pyridyl)-2-sulfopropyl)pentanedioic acid;
2-(1-phenyl-2-sulfobutyl)pentanedioic acid;
2-(1-(4-pyridyl)-2-sulfobutyl)pentanedioic acid; and
pharmaceutically acceptable salts, hydrates, metabolites, and prodrugs thereof.

The most preferred compounds of this embodiment are:
2-(2-sulfanylethyl)pentanedioic acid;
2-(2-sulfanylpropyl)pentanedioic acid;
2-(2-sulfanylbutyl)pentanedioic acid;
2-(2-phenyl-2-sulfanylethyl)pentanedioic acid;
2-(2-(4-pyridyl)-2-sulfanylethyl)pentanedioic acid;
2-(1-methyl-2-sulfanylpropyl)pentanedioic acid;
2-(1-ethyl-2-sulfanylpropyl)pentanedioic acid;
2-(1-propyl-2-sulfanylpropyl)pentanedioic acid;
2-(1-butyl-2-sulfanylpropyl)pentanedioic acid;
2-(2-sulfoethyl)pentanedioic acid;
2-[2-(ethylsulfonyl)ethyl]pentanedioic acid; and
pharmaceutically acceptable salts, hydrates, metabolites, and prodrugs thereof.

Preferred compounds of Formula XIII, wherein X is a moiety of Formula XV, $R_1$ is $(CH_2)_2COOH$, and $R_2$ is hydrogen, include:
2-(1-sulfanylethyl)pentanedioic acid;
2-(2-phenyl-1-sulfanylethyl)pentanedioic acid;
2-(2-phenyl-1-sulfanylpropyl)pentanedioic acid;
2-(2-phenyl-1-sulfanylbutyl)pentanedioic acid;
2-(2-(4-pyridyl)-1-sulfanylethyl)pentanedioic acid;
2-(2-(4-pyridyl)-1-sulfanylpropyl)pentanedioic acid;
2-[2-(4-pyridyl)-1-sulfanylbutyl]pentanedioic acid;
2-(2-methyl-1-sulfanylpropyl)pentanedioic acid;
2-(2-methyl-1-sulfanylbutyl)pentanedioic acid; and
pharmaceutically acceptable salts, hydrates, metabolites, and prodrugs thereof.

The most preferred compounds of this embodiment are:
2-(1-sulfanylethyl)pentanedioic acid;
2-(2-phenyl-1-sulfanylethyl)pentanedioic acid;
2-(2-phenyl-1-sulfanylpropyl)pentanedioic acid;
2-(2-phenyl-1-sulfanylbutyl)pentanedioic acid;
2-[2-(4-pyridyl)-1-sulfanylbutyl]pentanedioic acid;
2-(2-methyl-1-sulfanylbutyl)pentanedioic acid; and
pharmaceutically acceptable salts, hydrates, metabolites, and prodrugs thereof.

Preferred compounds of Formula XIII, wherein X is a moiety of Formula XVI, $R_1$ is $(CH_2)_2COOH$, $R_2$ is hydrogen, and Z is $CR_8$, include:
2-(dithiocarboxymethyl)pentanedioic acid;
2-(1-dithiocarboxyethyl)pentanedioic acid;
2-{[methylthio(thiocarbonyl)]methyl}pentanedioic acid;
2-{[ethylthio(thiocarbonyl)]methyl}pentanedioic acid;
2-{[propylthio(thiocarbonyl)]methyl}pentanedioic acid;
2-{[butylthio(thiocarbonyl)]methyl}pentanedioic acid;
2-(2-dithiocarboxy-1-phenylethyl)pentanedioic acid;
2-(2-dithiocarboxy-1-(4-pyridyl)ethyl)pentanedioic acid;
2-[dithiocarboxy(phenyl)methyl]pentanedioic acid;
2-[dithiocarboxy(4-pyridyl)methyl]pentanedioic acid; and
pharmaceutically acceptable salts, hydrates, metabolites, and prodrugs thereof.

The most preferred compounds of this embodiment are:
2-(dithiocarboxymethyl)pentanedioic acid;
2-(1-dithiocarboxyethyl)pentanedioic acid; and
pharmaceutically acceptable salts, hydrates, metabolites, and prodrugs thereof.

Preferred compounds of Formula XIII, wherein X is a moiety of Formula XVI, $R_1$ is $(CH_2)_2COOH$, $R_2$ is hydrogen, and Z is N, include:
2-[(methylsulfanylthiocarbonyl)amino]pentanedioic acid;
2-[(ethylsulfanylthiocarbonyl)amino]pentanedioic acid;
2-[(propylsulfanylthiocarbonyl)amino]pentanedioic acid;
2-[(butylsulfanylthiocarbonyl)amino]pentanedioic acid;
2-[(dithiocarboxy)amino]pentanedioic acid;
2-[(N-methyldithiocarboxy)amino]pentanedioic acid; and
pharmaceutically acceptable salts, hydrates, metabolites, and prodrugs thereof.

The most preferred compounds of this embodiment are:
2-dithiocarboxyaminopentanedioic acid;
2-[(N-methyldithiocarboxy)amino]pentanedioic acid; and
pharmaceutically acceptable salts, hydrates, metabolites, and prodrugs thereof.

Preferred compounds of Formula XIII, wherein X is a moiety of Formula XVII, $R_1$ is $(CH_2)_2COOH$, and $R_2$ is hydrogen include:
2-(2-sulfanylethoxy)pentanedioic acid;
2-(2-sulfanylpropoxy)pentanedioic acid;
2-(2-sulfanylbutoxy)pentanedioic acid;
2-(2-sulfanyl-2-phenyl-1-ethoxy)pentanedioic acid;
2-(2-sulfanyl-2-phenyl-1-propoxy)pentanedioic acid;
2-(2-sulfanyl-2-phenyl-1-butoxy)pentanedioic acid;
2-(2-sulfanyl-2-(4-pyridyl)-1-ethoxy)pentanedioic acid;
2-(2-sulfanyl-2-(4-pyridyl)-1-propoxy)pentanedioic acid;
2-(2-sulfanyl-2-(4-pyridyl)-1-butoxy)pentanedioic acid;
2-(1-sulfanylethoxy)pentanedioic acid;
2-(1-sulfanyl pypropoxy)pentanedioic acid;
2-(1-sulfanylbutoxy)pentanedioic acid;
2-(1-sulfanyl-2-phenyl-1-ethoxy)pentanedioic acid;
2-(1-sulfanyl-2-phenyl-1-propoxy)pentanedioic acid;
2-(1-sulfanyl-2-phenyl-1-butoxy)pentanedioic acid;
2-(1-sulfanyl-2-(4-pyridyl)-1-ethoxy)pentanedioic acid;
2-(1-sulfanyl-2-(4-pyridyl)-1-propoxy)pentanedioic acid;
2-(1-sulfanyl-2-(4-pyridyl)-1-butoxy)pentanedioic acid; and
pharmaceutically acceptable salts, hydrates, metabolites, and prodrugs thereof.

The most preferred compounds of this embodiment are:
2-(2-sulfanylethoxy)pentanedioic acid;
2-(2-sulfanylpropoxy)pentanedioic acid;
2-(2-sulfanylbutoxy)pentanedioic acid;
2-(2-sulfanyl-2-phenyl-1-propoxy)pentanedioic acid;
2-(1-sulfanylethoxy)pentanedioic acid;
2-(1-sulfanylpropoxy)pentanedioic acid;
2-(1-sulfanylbutoxy)pentanedioic acid;
2-(1-sulfanyl-2-phenyl-1-propoxy)pentanedioic acid; and
pharmaceutically acceptable salts, hydrates, metabolites, and prodrugs thereof.

In another preferred embodiment, $R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein $R_1$ is unsubstituted or substituted with one or more substituent(s).

Preferred compounds of this embodiment include:
2-benzyl-4-sulfanylbutanoic acid;
2-benzyl-4-sulfanylpentanoic acid;
2-phenyl-4-sulfanylbutanoic acid;
2-phenyl-4-sulfanylpentanoic acid;
2-(4-pyridyl)-4-sulfanylbutanoic acid;
2-(4-pyridyl)-4-sulfanylpentanoic acid;
2-(3-pyridylmethyl)-4-sulfanylpentanoic acid;
2-(3-pyridylmethyl)-4-sulfanylhexanoic acid;
2-benzyl-3-sulfanylpropanoic acid;
2-benzyl-3-sulfanylbutanoic acid;
2-benzyl-3-sulfanylpentanoic acid;
2-phenyl-3-sulfanylpropanoic acid;
2-phenyl-3-sulfanylbutanoic acid;
2-phenyl-3-sulfanylpentanoic acid;
2-(4-pyridyl)-3-sulfanypropanoic acid;
2-(4-pyridyl)-3-sulfanylbutanoic acid;
2-(4-pyridyl)-3-sulfanylpentanoic acid;
2-(4-pyridylmethyl)-3-sulfanylpropanoic acid;
2-(4-pyridylmethyl)-3-sulfanylbutanoic acid;
2-(4-pyridylmethyl)-3-sulfanylpentanoic acid; and
pharmaceutically acceptable salts, hydrates, metabolites, and prodrugs thereof.

The most preferred compounds of this embodiment are:
2-benzyl-4-sulfanylbutanoic acid;
2-benzyl-4-sulfanylpentanoic acid;
2-(3-pyridylmethyl)-4-sulfanylpentanoic acid;
2-(3-pyridylmethyl)-4-sulfanylhexanoic acid;
2-benzyl-3-sulfanylpropanoic acid;
2-benzyl-3-sulfanylpentanoic acid;
2-(4-pyridylmethyl)-3-sulfanylpentanoic acid; and pharmaceutically acceptable salts, hydrates, metabolites, and prodrugs thereof.

The structures and names of representative compounds of Formula XIII are set forth below.

| Structure | Name |
|---|---|
| 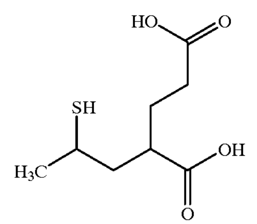 | 2-(2-sulfanylpropyl)-pentanedioic acid |
| 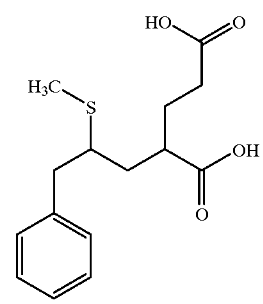 | 2-[2-(methylsulfanyl)-3-phenylpropyl]pentanedioic acid |
| 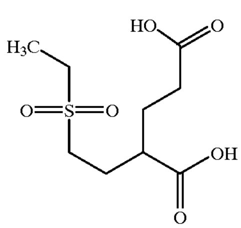 | 2-[2-(ethylsulfonyl)-ethyl]pentanedioic acid |
| 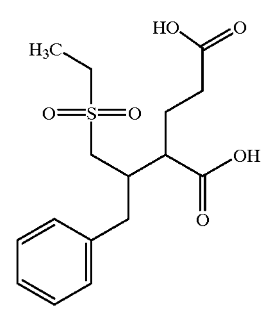 | 2-[1-benzyl-2-(ethylsulfonyl)ethyl]-pentanedioic acid |
| 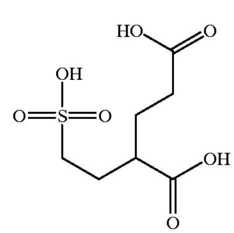 | 2-(2-sulfoethyl)-pentanedioic acid |

| Structure | Name |
|---|---|
| 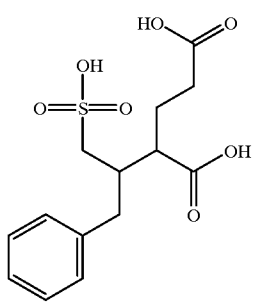 | 2-(1-benzyl-2-sulfoethyl)pentanedioic acid |
| 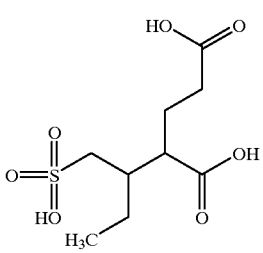 | 2-(1-ethyl-2-sulfopropyl)pentanedioic acid |
| 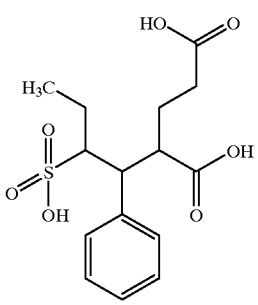 | 2-(1-phenyl-2-sulfobutyl)pentanedioic acid |
| 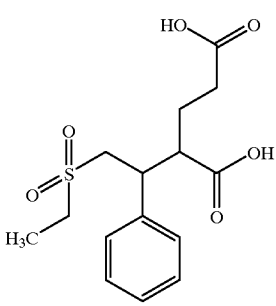 | 2-[2-(ethylsulfonyl)-1-phenylethyl]pentanedioic acid |
| 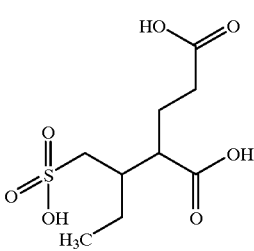 | 2-[1-(sulfomethyl)-propyl]pentanedioic acid |

| Structure | Name |
|---|---|
| 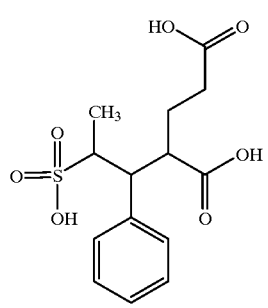 | 2-(1-phenyl-2-sulfopropyl)pentanedioic acid |
| 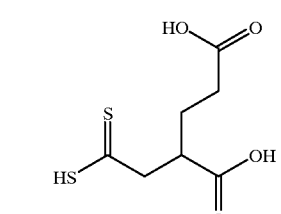 | 2-(dithiocarboxymethyl)-pentanedioic acid |
| 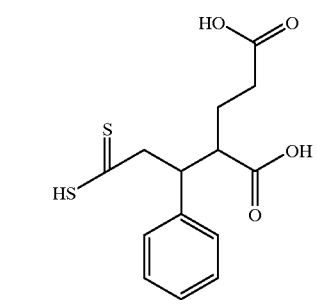 | 2-(2-dithiocarboxy-1-phenylethyl)pentanedioic acid |
| 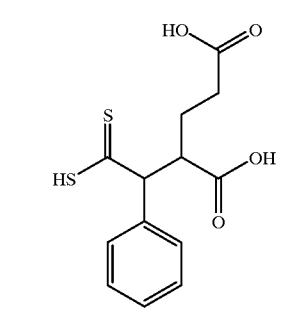 | 2-[dithiocarboxy(phenyl)-methyl]pentanedioic acid |
| 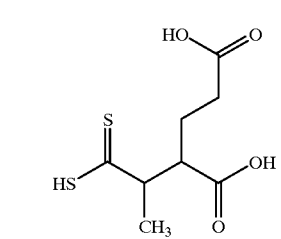 | 2-(1-dithiocarboxyethyl)-pentanedioic acid |

-continued

| Structure | Name |
|---|---|
| 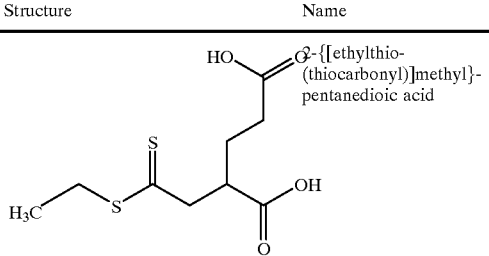 | 2-{[ethylthio-(thiocarbonyl)]methyl}-pentanedioic acid |
| 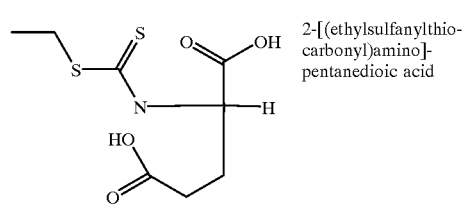 | 2-[(ethylsulfanylthio-carbonyl)amino]-pentanedioic acid |
| 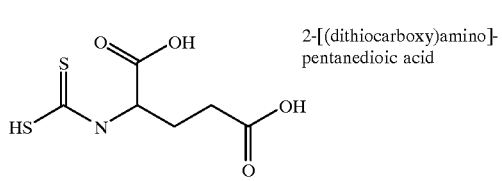 | 2-[(dithiocarboxy)amino]-pentanedioic acid |
| 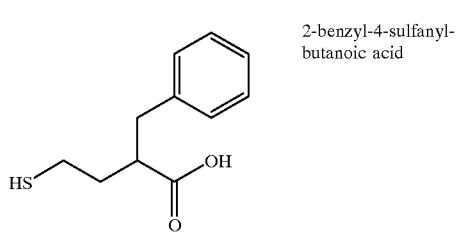 | 2-benzyl-4-sulfanyl-butanoic acid |
| 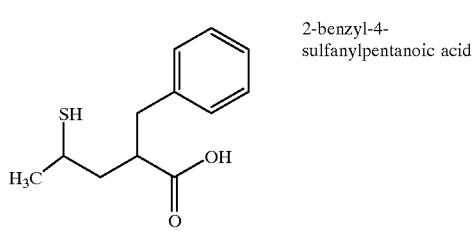 | 2-benzyl-4-sulfanylpentanoic acid |
| 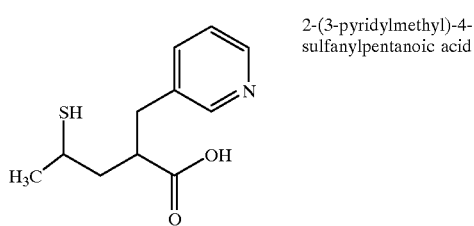 | 2-(3-pyridylmethyl)-4-sulfanylpentanoic acid |
| 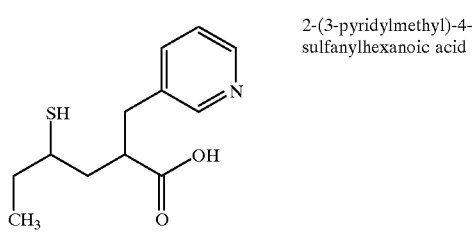 | 2-(3-pyridylmethyl)-4-sulfanylhexanoic acid |

-continued

| Structure | Name |
|---|---|
| 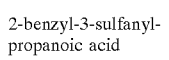 | 2-benzyl-3-sulfanyl-propanoic acid |
| 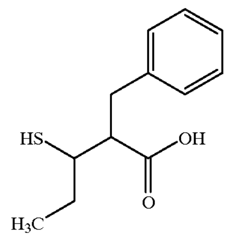 | 2-benzyl-3-sulfanylpentanoic acid |
| 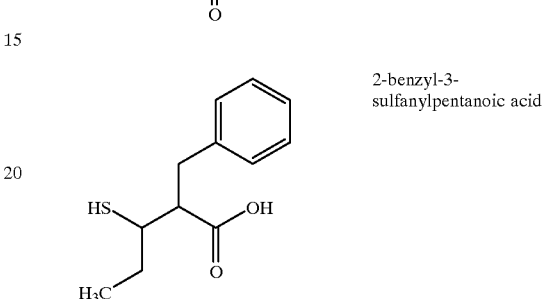 | 2-(4-pyridylmethyl)-3-sulfanylpentanoic acid |
| 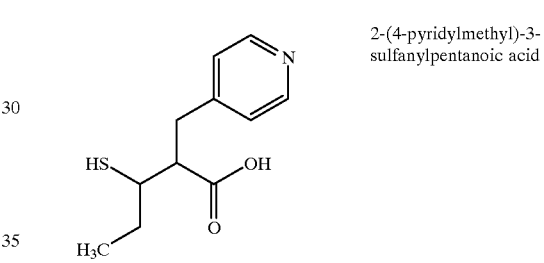 | 2-(1-benzyl-2-sulfanylethyl)-pentanedioic acid |
| 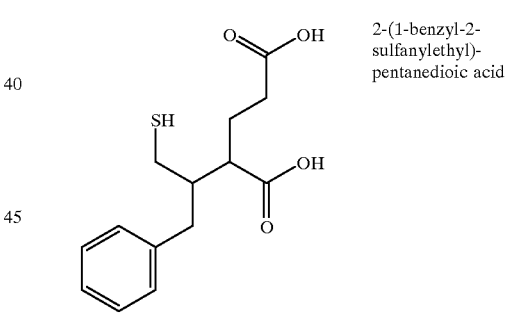 | 2-(1-methyl-2-sulfanylethyl)-pentanedioic acid |
| 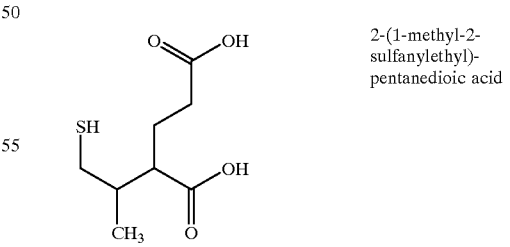 | |

A final preferred NAALADase inhibitor is a compound of Formula XIX:

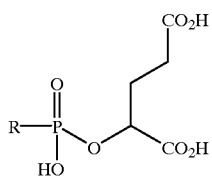

or a pharmaceutically acceptable salt or hydrate thereof, wherein:

R is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, Ar and mixtures thereof, wherein said R is unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar or a mixture thereof;

Ar is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_6$ alkoxy or $C_1$–$C_6$ alkenyloxy, phenoxy, benzyloxy, and amino.

In a preferred embodiment, the compound is selected from the group consisting of:
2-[[methylhydroxyphosphinyl]oxy]pentanedioic acid;
2-[[ethylhydroxyphosphinyl]oxy]pentanedioic acid;
2-[[butylhydroxyphosphinyl]oxy]pentanedioic acid;
2-[[phenylhydroxyphosphinyl]oxy]pentanedioic acid;
2-[[((4-pyridyl)methyl)hydroxyphosphinyl]oxy]pentanedioic acid;
2-[[((2-pyridyl)methyl)hydroxyphosphinyl]oxy]pentanedioic acid;
2-[[(phenylmethyl)hydroxyphosphinyl]oxy]pentanedioic acid; and
2-[[((2-phenylethyl)methyl)hydroxyphosphinyl]oxy]pentanedioic acid.

The compounds of the present invention possess one or more asymmetric center(s) and thus can be produced as mixtures (racemic and non-racemic) of stereoisomers, or as individual R- and S-stereoisomers. The individual stereoisomers may be obtained by using an optically active starting material, by resolving a racemic or non-racemic mixture of an intermediate at some appropriate stage of synthesis, or by resolving a compound of formula I. It is understood that the compounds of the present invention encompass optical isomers, individual stereoisomers as well as mixtures (racemic and non-racemic) of stereoisomers.

Synthesis of NAALADase Inhibitors

The NAALADase inhibitors of the present invention can be readily prepared by standard techniques of organic chemistry, utilizing the general synthetic pathways depicted below in Schemes I–XII. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995).

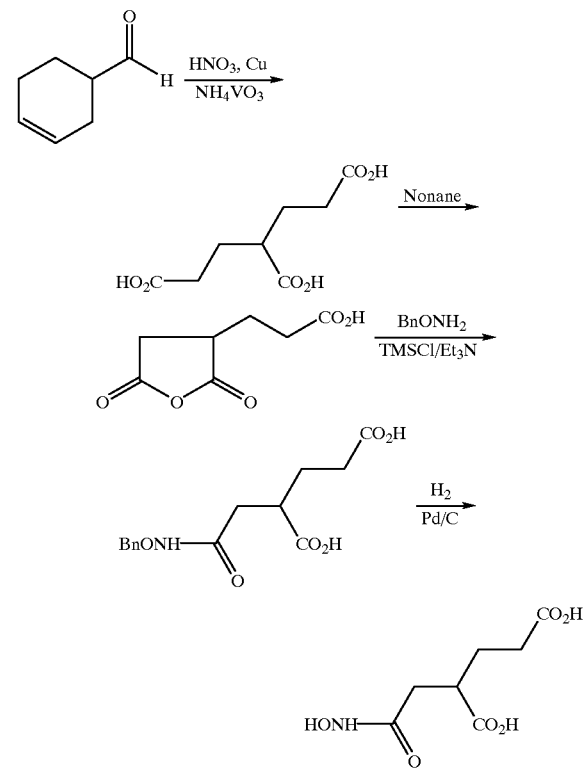

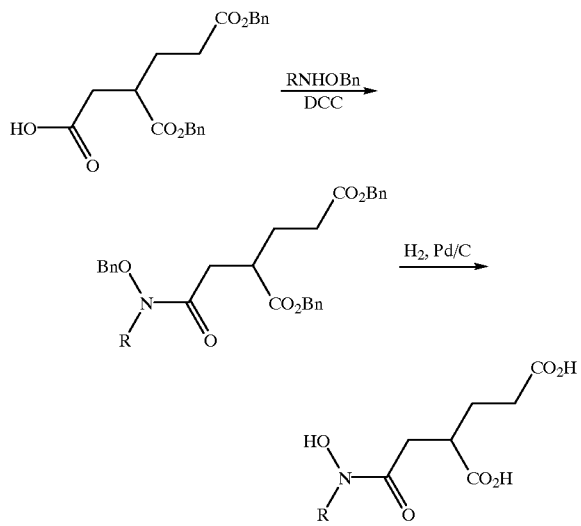

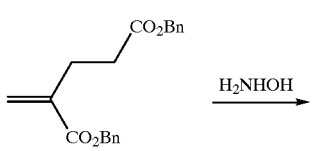

-continued

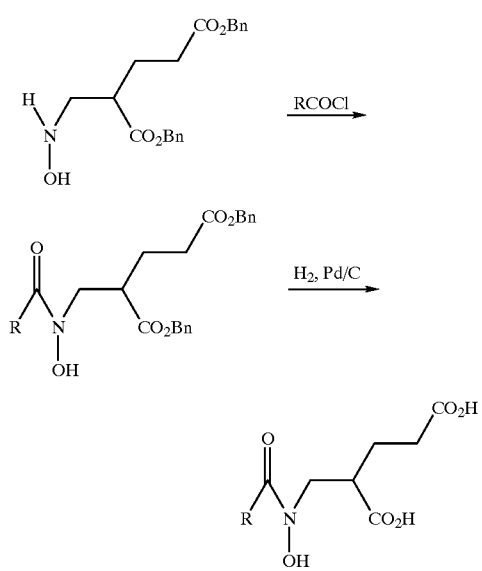

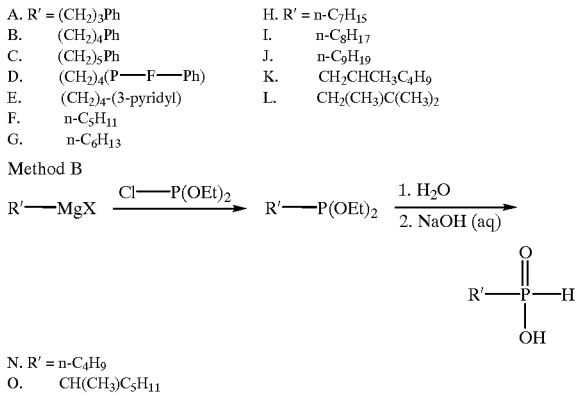

A. R' = (CH₂)₃Ph  H. R' = n-C₇H₁₅
B.    (CH₂)₄Ph  I.    n-C₈H₁₇
C.    (CH₂)₅Ph  J.    n-C₉H₁₉
D.    (CH₂)₄(P—F—Ph)  K.    CH₂CHCH₃C₄H₉
E.    (CH₂)₄-(3-pyridyl)  L.    CH₂(CH₃)C(CH₃)₂
F.    n-C₅H₁₁
G.    n-C₆H₁₃

N. R' = n-C₄H₉
O.    CH(CH₃)C₅H₁₁

Starting with the aforementioned phosphinic acid esters, there are a variety of routes for preparing the compounds of Formula I. For example, a general route has been described in *J. Med. Chem.*, Vol. 39, pp. 619–622 (1996), and is set forth below in Scheme VI.

Scheme IV

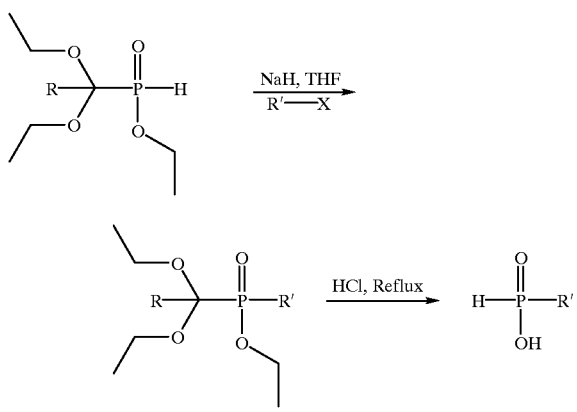

Scheme VI

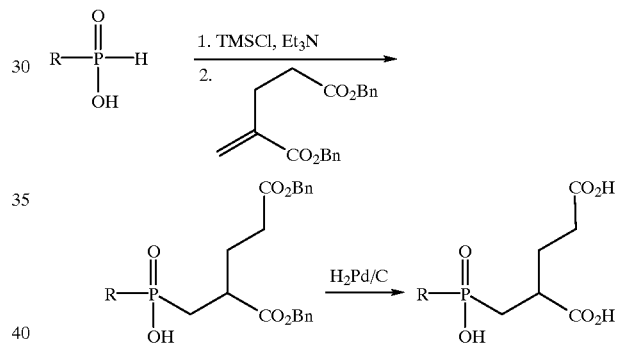

Methods of substituting the R group are known in the art. Additional methods of synthesizing phosphinic acid esters are described in *J. Med. Chem.*, Vol. 31, pp. 204–212 (1988), and set forth below in Scheme V.

Other routes for preparing the compounds of Formula I are set forth below in Scheme VII and Scheme VIII. Scheme VII and Scheme VIII show the starting material as a phosphinic acid derivative and the R group as any reasonable chemical substituent including without limitation the substituents listed in Scheme V and throughout the specification.

Scheme V

Method A

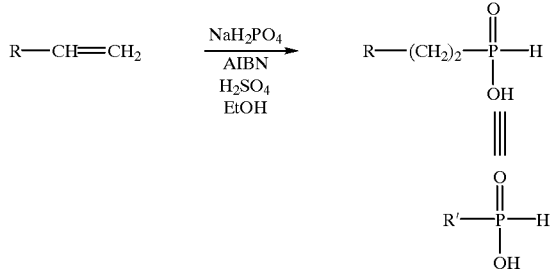

Scheme VII

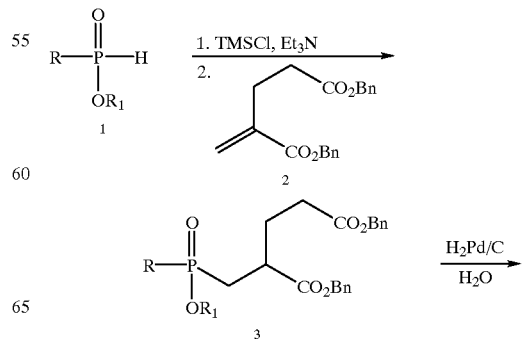

Scheme VIII
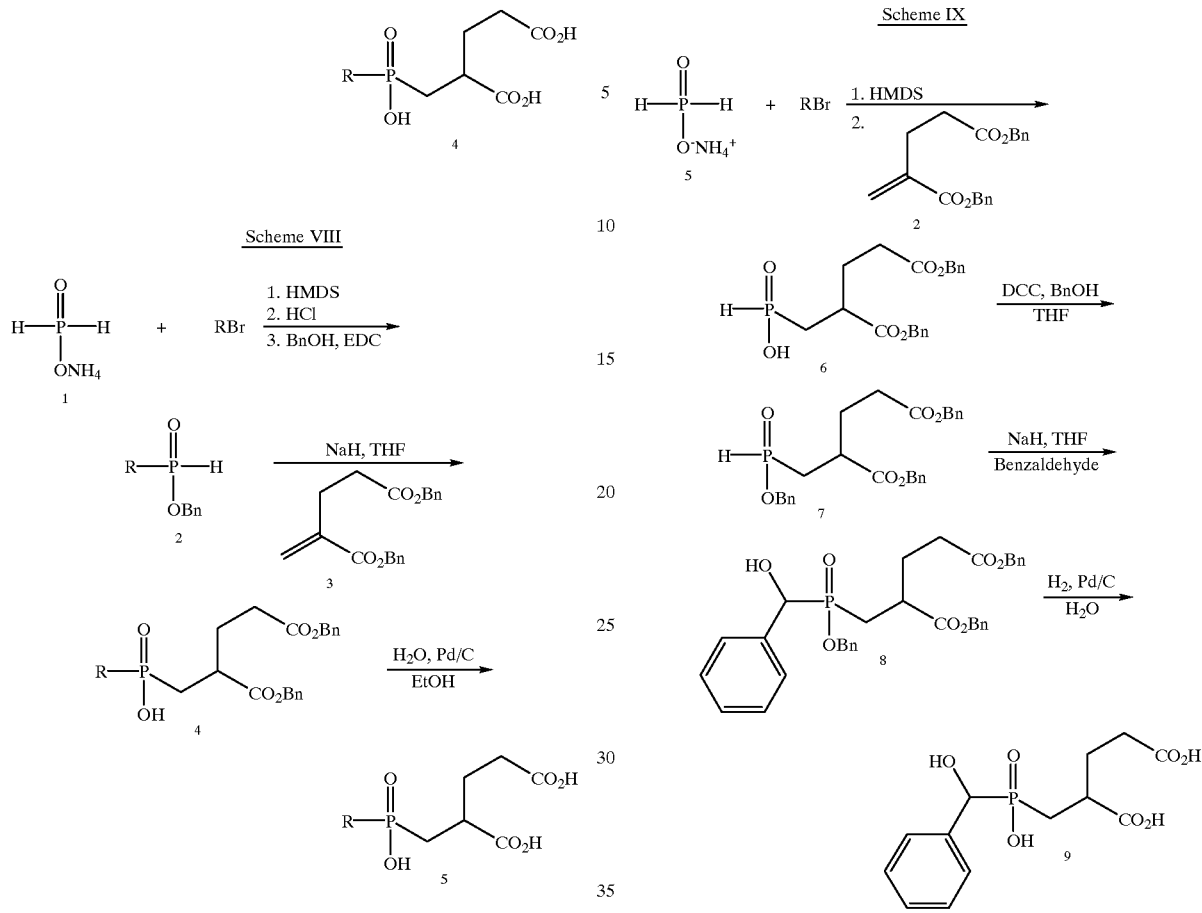
Scheme IX
Another route for preparing the compounds of Formula I allows for aromatic substitution at $R_1$, and is set forth below in Scheme IX.
Another route for preparing the compounds of Formula I allows for aromatic substitution at the $R_2$ position, and is set forth below in Scheme X.
Scheme X
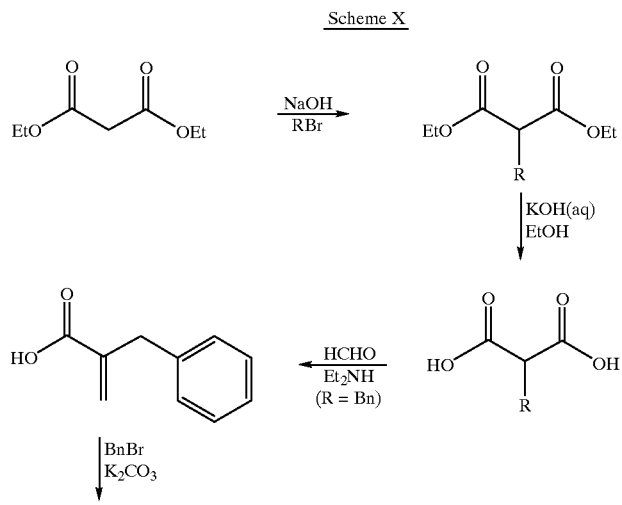

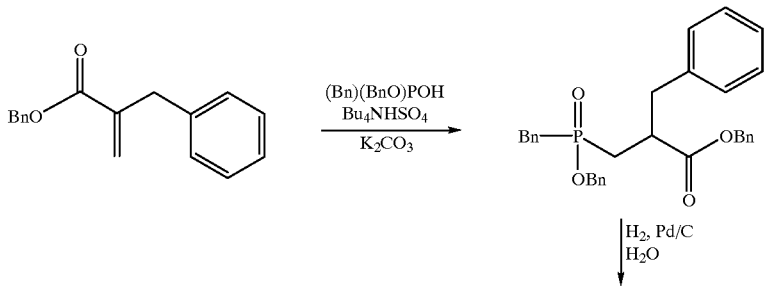
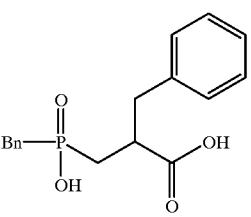
Another route for preparing the compounds of Formula I wherein Y is NR$_5$ is set forth below in Scheme XI.
Scheme XI
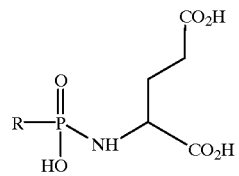
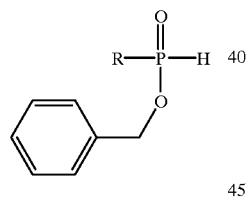
Another route for preparing the compounds of Formula I wherein Y is oxygen is set forth below in Scheme XII.
Scheme XII
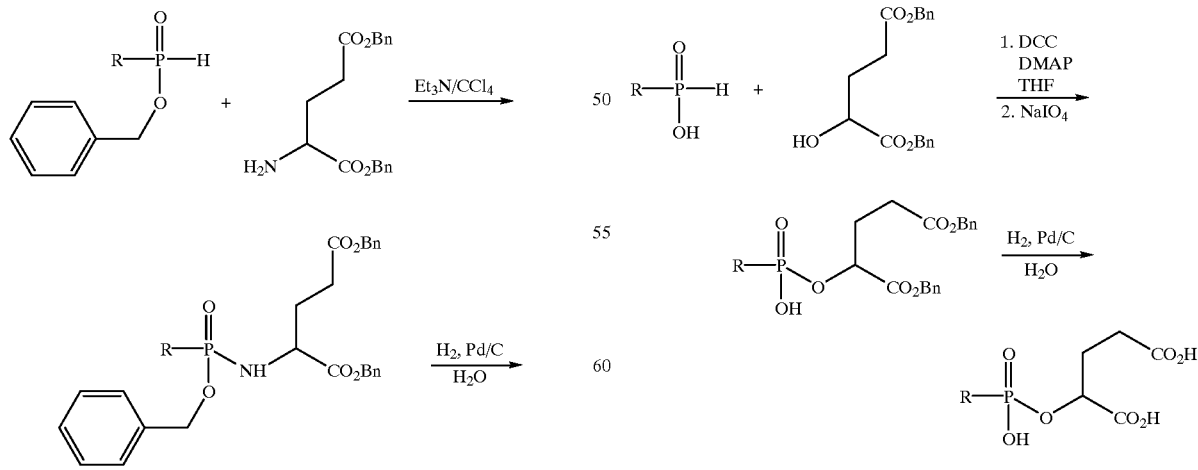

Scheme XIII
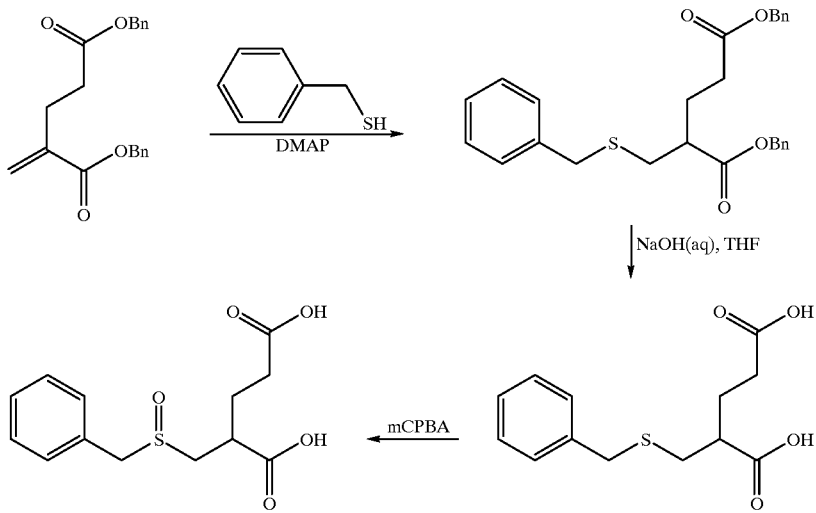
Scheme XIV
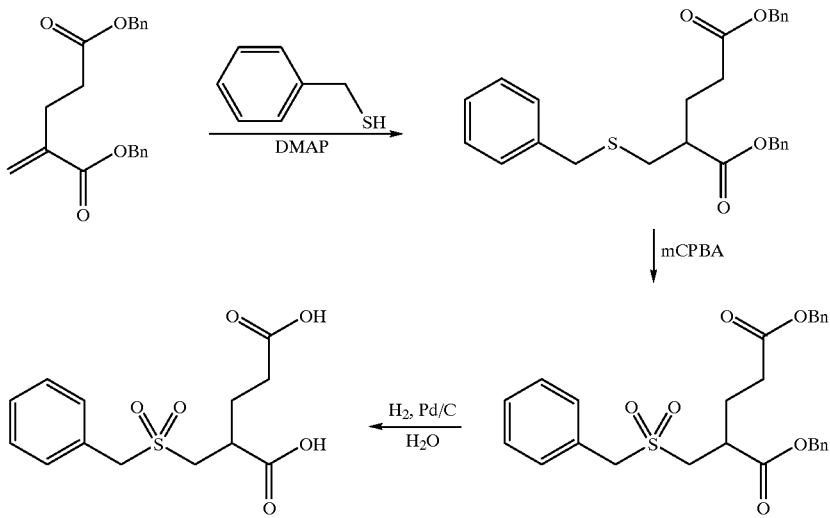
Scheme XV
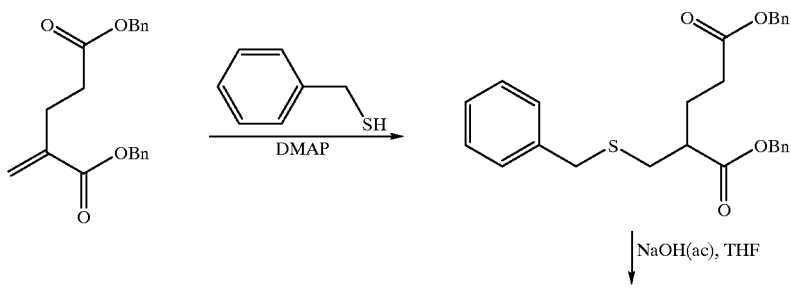

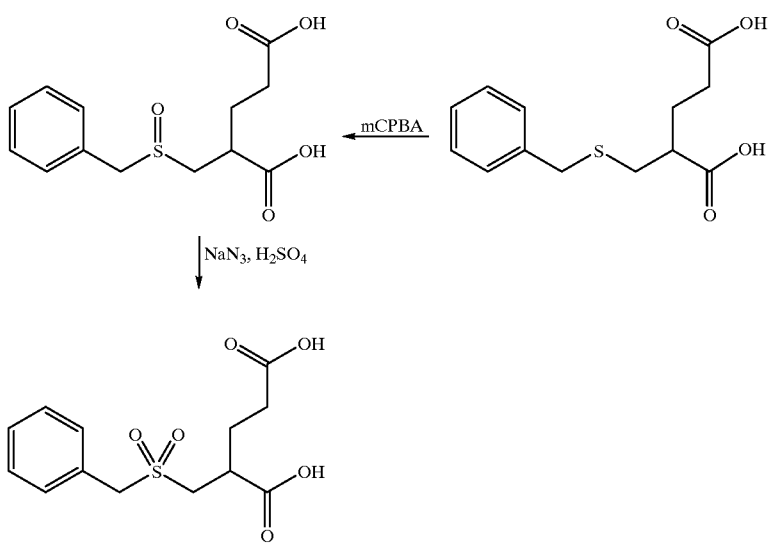
The compounds of the present invention where X is a moiety of Formula XIII can be readily prepared by standard techniques of organic chemistry, utilizing the general synthetic pathways depicted below in Schemes XVI–XX. Precursor compounds can be prepared by methods known in the art.
Scheme XVI
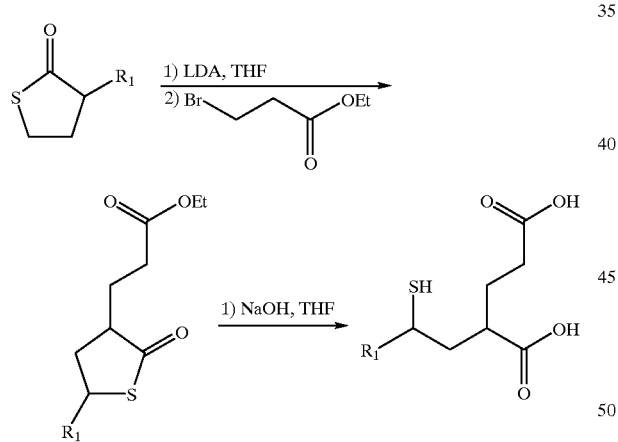
Scheme XVII
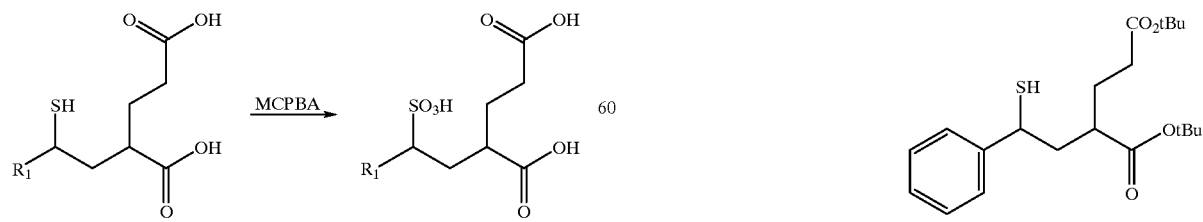
Scheme XVIII
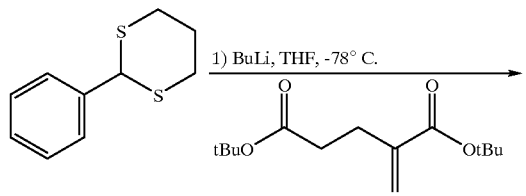
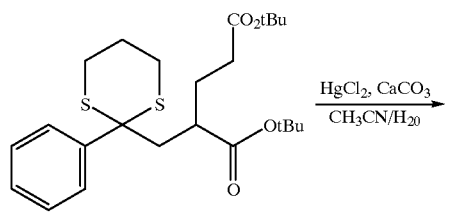
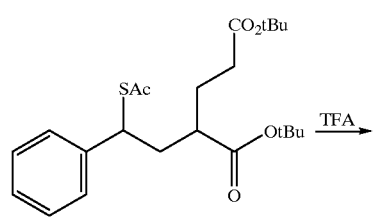
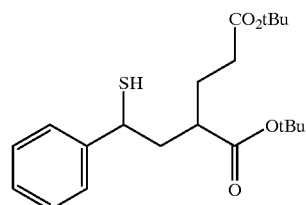

Scheme XIX

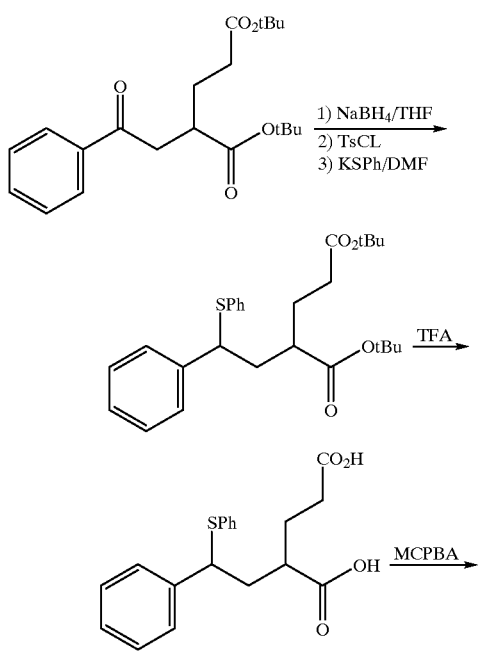

Scheme XX

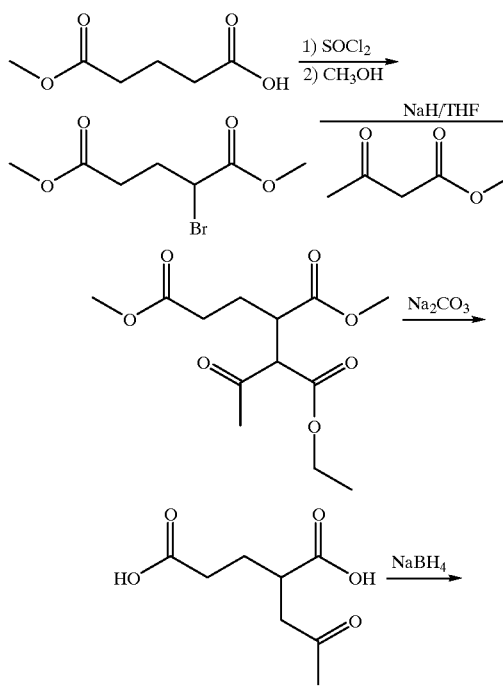

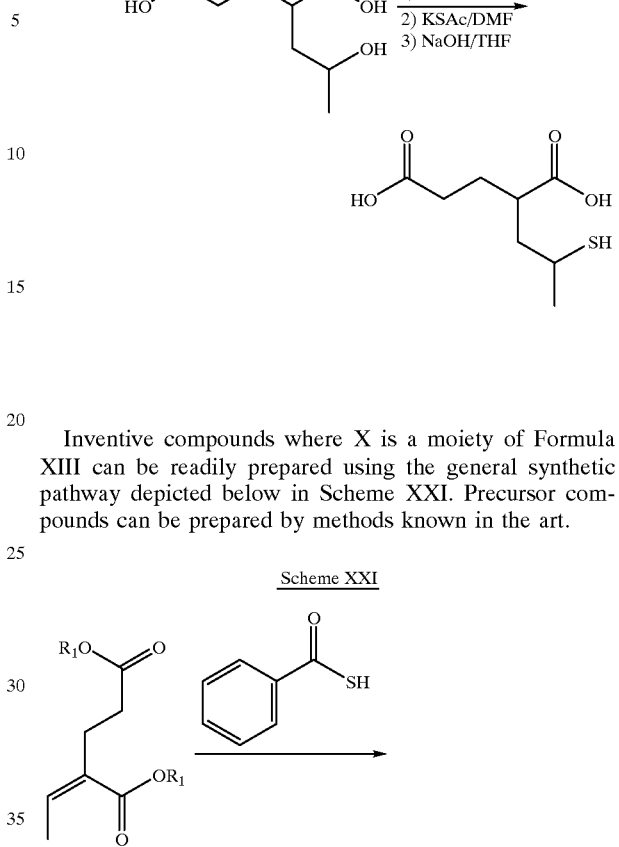

Inventive compounds where X is a moiety of Formula XIII can be readily prepared using the general synthetic pathway depicted below in Scheme XXI. Precursor compounds can be prepared by methods known in the art.

Scheme XXI

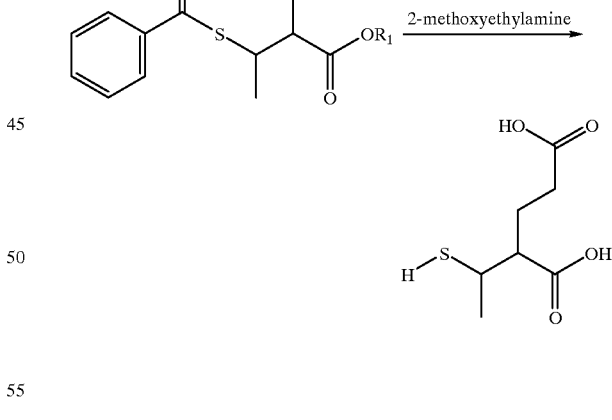

Inventive compounds where X is a moiety of Formula XVI can be readily prepared using several synthetic pathways, such as reacting a glutamate derivative with carbon disulfide.

Inventive compounds where X is a moiety of Formula XVII can be readily prepared using the general synthetic pathway depicted below in Schemes XXII–XXIV. Precursor compounds can be prepared by methods known in the art.

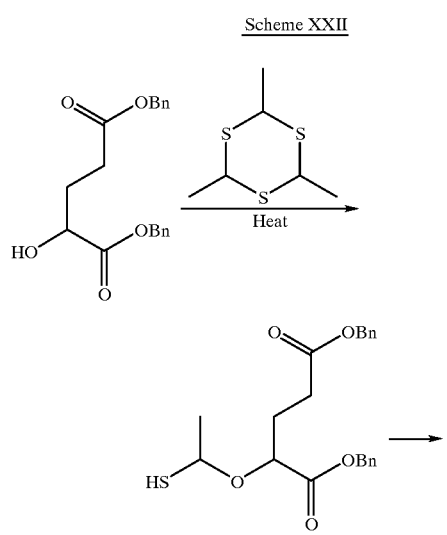
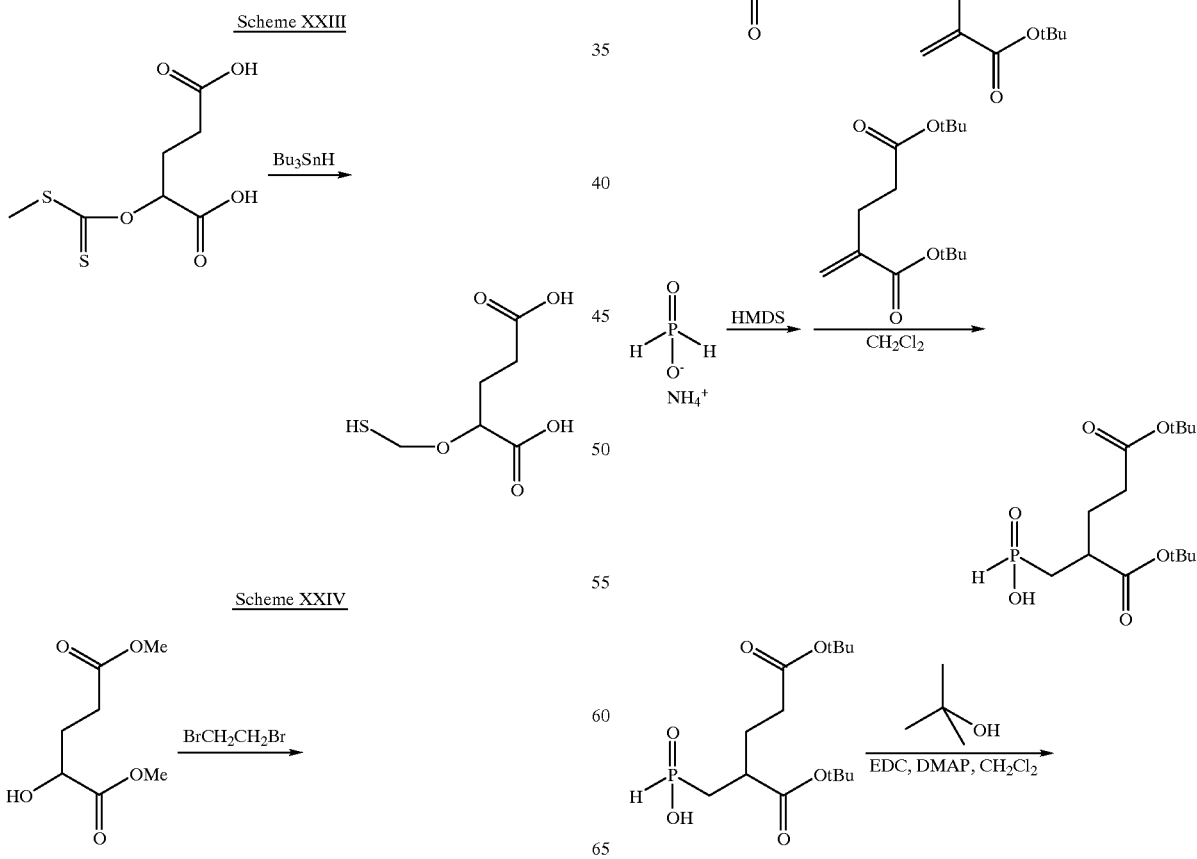
The compounds of Formula XI can be readily prepared by standard techniques of organic chemistry, utilizing the general synthetic pathways depicted below in Scheme XXV. Precursor compounds can be prepared by methods known in the art.

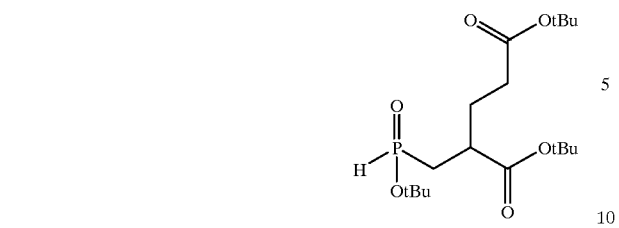
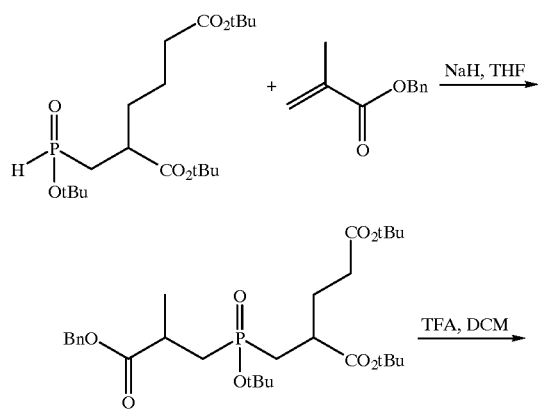
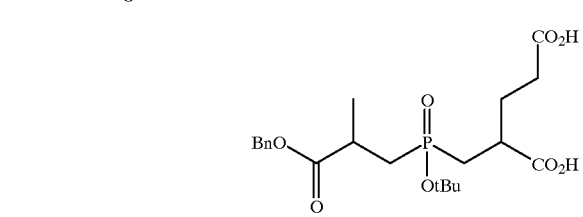
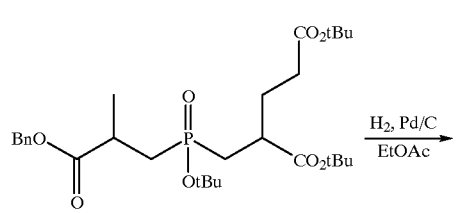
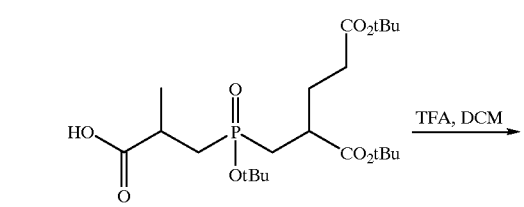
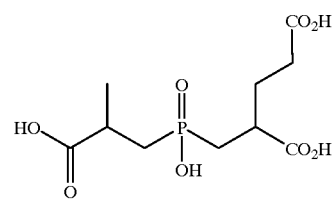
The compounds of Formula XII can be readily prepared by standard techniques of organic chemistry, utilizing the general synthetic pathways depicted below in Scheme XXVI and Scheme XXVII. Precursor compounds can be prepared by methods known in the art.
Scheme XXVI
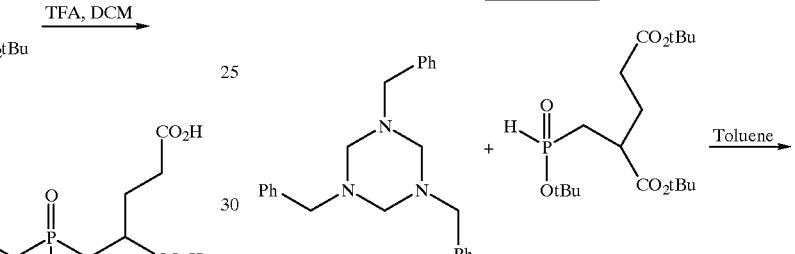
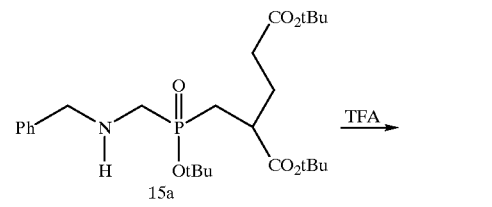
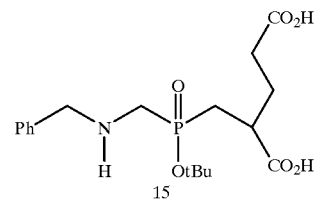
Scheme XXVII
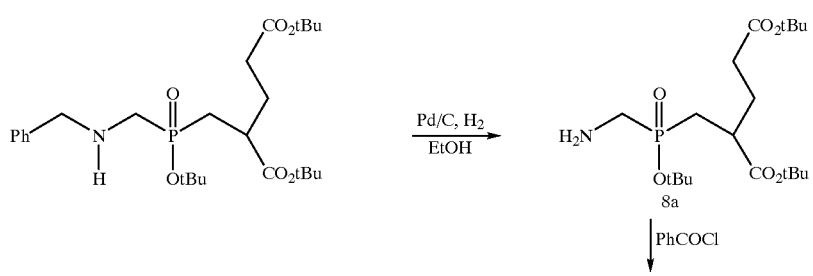

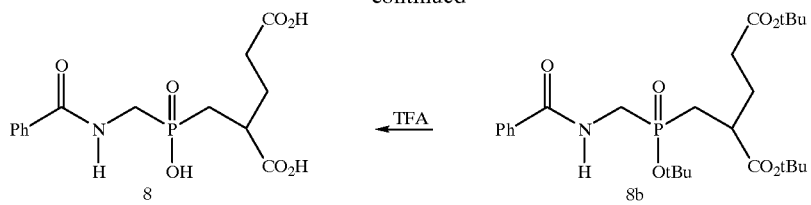

Methods of the Present Invention

The inventors have unexpectedly found that NAALA-Dase inhibitors are effective in inhibiting angiogenesis.

Accordingly, the present invention further relates to a method of inhibiting angiogenesis, comprising administering an effective amount of a NAALADase inhibitor to a patient in need thereof.

The angiogenesis to be inhibited may be involved in any angiogenic-dependent disease. Methods of angiogenic-dependent diseases treatable by the methods of the present invention include, but are not limited to, cancerous tumor growth, invasion, and metastasis, rheumatoid arthritis, cardiovascular disease, neovascular diseases of the eye, and peripheral vascular disorders.

Examples of NAALADase inhibitors useful for the methods of the present invention are identified above in relation to pharmaceutical compositions.

Method of Treating Cancer

By inhibiting angiogenesis, several forms of cancer may be treated with the compounds of the present invention including without limitation: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

The compounds of the present invention are particularly useful in inhibiting angiogenesis in cancerous tumors in tissues where NAALADase enzymes reside. Such tissues include, but are not limited to, the brain, kidney, prostate, testis, and blood vessels.

Route of Administration

In the methods of the present invention, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be effective therapeutically as central nervous system targets, the NAALADase inhibitors used in the methods of the present invention should readily penetrate the blood-brain barrier when peripherally administered. Compounds which cannot penetrate the blood-brain barrier can be effectively administered by an intraventricular route.

Compositions and methods of the invention also may utilize controlled release technology. Thus, for example, NAALADase inhibitors may be incorporated into a hydrophobic polymer matrix for controlled release over a period of days. Such controlled release films are well known to the art. Examples of polymers commonly employed for this purpose that may be used in the present invention include nondegradable ethylene-vinyl acetate copolymer and degradable lactic acid-glycolic acid copolymers. Certain hydrogels such as poly(hydroxyethylmethacrylate) or poly(vinylalcohol) also may be useful, but for shorter release cycles then the other polymer releases systems, such as those mentioned above.

The NAALADase inhibitor preparation of the invention may be coupled to a bridging compound coupled to a solid support. The bridging compound, which is designed to link the solid support and the NAALADase inhibitor, may be hydrazide, Protein A, glutaraldehyde, carbodiimide, or lysine.

The solid support employed is, e.g., a polymer or it may be a matrix coated with a polymer. The matrix may be of any suitable solid material, e.g., glass, paper, or plastic. The polymer may be a plastic, cellulose such as specially treated paper, nitrocellulose paper, or cyanogenbromide-activated paper. Examples of suitable plastics are latex, a polystyrene, polyvinylchloride, polyurethane, polyacrylamide, polyvinylacetate, and any suitable copolymer thereof. Examples of silicone polymers include siloxane.

The solid support may be in the form of a tray, a plate such as a microtiter plate, e.g., a thin layer or, preferably, strip, film, threads, solid particles such as beads, including Protein A-coated bacteria, or paper.

The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed.

Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The NAALADase inhibitors may be administered vaginally using gels, foams, creams, suppositories, or carbopol polymers. Particularly preferred vehicles include acrylic acid polymers including polymers modified by long chain ($C_{10}$–$C_{30}$) alkyl acrylates. A representative vehicle is manufactured by B. F. Goodrich and is identified as a carbopol polymer having viscosities of around 20,400–39,400. Useful vehicles should also possess a pH around 3 to 6 to be compatible with the normal vaginal pH of 4.0 to 5.5 and furthermore be stable when pH buffers in the range of vaginal pH are used.

The NAALADase inhibitors used in the methods of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

Dosage

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

In a preferred embodiment, the NAALADase inhibitors are administered in lyophilized form. In this case, 1 to 100 mg of a NAALADase inhibitor may be lyophilized in individual vials, together with a carrier and a buffer, such as mannitol and sodium phosphate. The compound may be reconstituted in the vials with bacteriostatic water before administration.

The NAALADase inhibitors used in the methods of the present invention may be administered in combination with one or more therapeutic agents, including chemo-therapeutic agents. TABLE I provides known median dosages for selected chemotherapeutic agents. Specific dose levels for these agents will depend upon considerations such as those identified above for the NAALADase inhibitors.

TABLE I

| ADMINISTRATION REGIMEN | |
|---|---|
| CHEMOTHERAPEUTIC AGENT | MEDIAN DOSAGE |
| Aldesleukin | 22 million units |
| Asparaginase | 10,000 units |
| Bleomycin Sulfate | 15 units |
| Carboplatin | 50–450 mg |
| Carmustine | 100 mg |
| Cisplatin | 10–50 mg |
| Cladribine | 10 mg |
| Cyclophosphamide (lyophilized) | 100 mg–2 gm |
| Cyclophosphamide (non-lyophilized) | 100 mg–2 gm |
| Dacarbazine | 100 mg–200 mg |
| Dactinomycin | 0.5 mg |
| Daunorubicin | 20 mg |
| Diethylstilbestrol | 250 mg |
| Doxorubicin | 10–150 mg |
| Epoetin Alfa | 2,000–10,000 units |
| Etidronate | 300 mg |
| Etoposide | 100 mg |
| Filgrastim | 300–480 mcgm |
| Floxuridine | 500 mg |
| Fludarabine Phosphate | 50 mg |
| Fluorouracil | 500 mg–5 gm |
| Goserelin | 3.6 mg |
| Granisetron Hydrochloride | 1 mg |
| Idarubicin | 5–10 mg |
| Ifosfamide | 1–3 gm |
| Immune Globulin | 500 mg–10 gm |
| Interferon Alpha-2a | 3–36 million units |
| Interferon Alpha-2b | 3–50 million units |
| Leucovorin Calcium | 50–350 mg |
| Leuprolide | 3.75–7.5 mg |
| Levamisole | 50 mg |
| Mechlorethamine | 10 mg |
| Medroxyprogesterone | 1 gm |
| Melphalan | 50 gm |

TABLE I-continued

ADMINISTRATION REGIMEN

| CHEMOTHERAPEUTIC AGENT | MEDIAN DOSAGE |
|---|---|
| Nethotrexate | 20 mg–1 gm |
| Mitomycin | 5–40 mg |
| Mitoxantrone | 20–30 mg |
| Octreotide | 1,000–5,000 mcgm |
| Ondansetron Hydrochloride | 40 mg |
| Paclitaxel | 30 mg |
| Pamidronate Disodium | 30–90 mg |
| Pegaspargase | 750 units |
| Plicamycin | 2,500 mcgm |
| Sargramostim | 250–500 mcgm |
| Streptozocin | 1 gm |
| Teniposide | 50 mg |
| Thiotepa | 15 mg |
| Vinblastine | 10 mg |
| Vincristine | 1–5 mg |

Administration Regimen

For the methods of the present invention, any administration regimen regulating the timing and sequence of drug delivery can be used and repeated as necessary to effect treatment. Such regimen may include pretreatment and/or co-administration with additional therapeutic agents.

For patients with prostate cancer that is neither advanced nor metastatic, the compounds of the present invention may be administered (i) prior to surgery or radiation treatment to reduce the risk of metastasis; (ii) during surgery or in conjunction with radiation treatment; and/or (iii) after surgery or radiation therapy to reduce the risk of recurrence and to inhibit the growth of any residual tumorous cells.

For patients with advanced or metastatic cancer, the compounds of the present invention may be administered as a continuous supplement to, or as a replacement for, hormonal ablation in order to slow tumor cell growth in both the untreated primary tumor and the existing metastatic lesions.

The methods of the present invention are particularly useful where shed cells could not be removed by surgical intervention. After post-surgical recovery, the methods of the present invention would be effective in reducing the chances of recurrence of a tumor engendered by such shed cells.

Combination with Other Treatments a. Angiogenesis-Dependent Disease

The NAALADase inhibitors can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a NAALADase inhibitor, as well as one or more pharmaceutical excipients, such as wetting, emulsifying and pH buffering agents.

b. Cancer (i) Surgery and Radiation Treatment

In general, surgery and radiation treatment are employed as potentially curative therapies for patients with localized cancer who are under 70 years of age and are expected to live at least 10 more years.

If treated with surgery alone, however, many patients will experience recurrence of the cancer. Radiation treatment can also be problematic as the radiotherapeutic agents are toxic to normal tissues, and often create life-threatening side effects.

Use of the present invention in conjunction with surgery and radiation treatment could prevent remission and allow lower dosage levels of toxic radiotherapeutic agents. Based on the above statistics, there is considerable opportunity to use the present invention in conjunction with, or as an alternative to, surgery and/or radiation treatment.

(ii) Radiosensitizers

Radiosensitizers are known to increase the sensitivity of cancerous cells to the toxic effects of electromagnetic radiation. Several mechanisms for the mode of action of radiosensitizers have been suggested in the literature, among them are: hypoxic cell radiosensitizers (e.g. 2-nitroimidazole compounds, and benzotriazine dioxide compounds) promote the reoxygenation of hypoxic tissue, and/or catalyze the generation of damaging oxygen radicals; non-hypoxic cell radiosensitizers (e.g. halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include the following, but are not limited to: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the electromagnetic radiation activator of the sensitizing agent. Examples of photodynamic electromagnetic radiosensitizers include the following, but are not limited to: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

The compounds of the present invention may be administered in combination with electromagnetic radiosensitizers to increase the sensitivity of cancerous cells to the toxic effects of electromagnetic radiation. Use of the present invention in conjunction with electromagnetic radiosensitizers could prevent remission and allow lower dosage levels of electromagnetic radiation. Combining electromagnetic radiation with the methods and compounds of the present invention should be more effective than electromagnetic radiation alone in treating cancer.

A combination consisting of electromagnetic radiosensitizers and the compounds of the present invention may also be administered in conjunction with a therapeutically effective amount of one or more other compounds, including but not limited to: compounds which promote the incorporation of radiosensitizers to the target cells; compounds which control the flow of therapeutics, nutrients and/or oxygen to the target cells; chemotherapeutic agents which act on the tumor with or without additional electromagnetic radiation; or other therapeutically effective compounds for treating cancer or other diseases. Examples of additional therapeutic agents that may be used in conjunction with the combination consisting of electromagnetic radiosensitizers and the compounds of the present invention include, but are not limited to: 5-fluorouracil, leucovorin, 5'-amino-5'deoxythymidine, oxygen, carbogen, red cell transfusions, perfluorocarbons (e.g. Fluosol-DA), 2,3-DPG, BW12C, calcium channel blockers, pentoxyfylline, hydralazine, and L-BSO. Examples of chemotherapeutic agents that may be used in conjunction with the combination consisting of electromagnetic radiosensitizers and the compounds of the present invention include, but are not limited to, the chemotherapeutic agents listed in TABLE I.

(iii) Hormonal Therapy

Hormonal ablation by medication and/or orchiectomy is used to block hormones that promote further growth and metastasis of cancer. With time, both the primary and metastatic tumors of virtually all of these patients become hormone-independent and resistant to therapy. Continuous supplementation with the compounds of the present invention may be used to prevent or reverse this potentially metastasis-permissive state.

(iv) Chemotherapy

Chemotherapy has been successful in treating some forms of cancer. However, in treating other forms of cancer, chemotherapy has been reserved only as a last resort. In any case, chemotherapy can be problematic as chemotherapeutic agents are toxic to normal tissues and often create life threatening side effects. Additionally, chemotherapy often has high failure and/or remission rates.

Use of the present invention in conjunction with chemotherapy could prevent remission and allow lower dosage levels of toxic chemotherapeutic agents. Combining chemotherapy with the methods of the present invention should be more effective than chemotherapy alone in treating cancer.

(v) Immunotherapy

The compounds of the present invention may also be used in combination with monoclonal antibodies to treat cancer. The present invention may also be used with immunotherapies based on polyclonal or monoclonal antibody-derived reagents. These reagents are well known in the art, and include radiolabeled monoclonal antibodies such as monoclonal antibodies conjugated with strontium-89.

In Vivo Toxicity of NAALADase Inhibitors

To examine the toxicological effect of NAALADase inhibition in vivo, a group of mice were injected with 2-(phosphonomethyl)pentanedioic acid, a NAALADase inhibitor of high activity, in doses of 1, 5, 10, 30, 100, 300 and 500 mg/kg body weight. The mice were subsequently observed two times per day for 5 consecutive days. The survival rate at each dose level is provided below in TABLE II. The results show that the NAALADase inhibitor is non-toxic to mice, suggesting that it would be similarly non-toxic to humans when administered at therapeutically effective amounts.

TABLE II

| TOXICOLOGICAL EFFECTS OF NAALADASE INHIBITORS | | | | | | | |
|---|---|---|---|---|---|---|---|
| Dose (mg/kg) | 1 | 5 | 10 | 30 | 100 | 300 | 500 |
| Survival Rate After 5 days (%) | 100 | 100 | 100 | 100 | 100 | 100 | 66.7 |

In Vitro Inhibition of NAALADase Activity

Various compounds of the present invention were tested for in vitro inhibition of NAALADase activity. The results are provided below in TABLE III.

TABLE III

IN VITRO INHIBITION OF NAALADASE ACTIVITY

| Compound | $K_i$ (nM) |
|---|---|
| 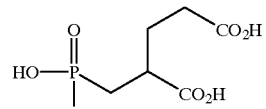<br>2-(phosphonomethyl)pentanedioic acid | 0.293 + 0.08 |
| 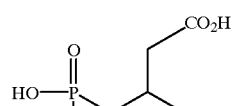<br>2-(phosphonomethyl)succinic acid | 700.00 + 67.3 |
| 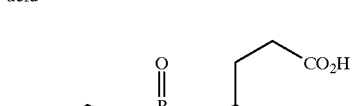<br>carboxyethyl)hydroxyphosphinyl]-methyl]pentanedioic acid | 1.89 + 0.19 |

TABLE III-continued

IN VITRO INHIBITION OF NAALADASE ACTIVITY

| Compound | $K_i$ (nM) |
|---|---|
| benzyl-P(=O)(OH)-CH$_2$-CH(CO$_2$H)-CH$_2$-CH$_2$-CO$_2$H | 34.15 |
| phenyl-P(=O)(OH)-CH$_2$-CH(CO$_2$H)-CH$_2$-CH$_2$-CO$_2$H | 35.85 |
| α-hydroxybenzyl-P(=O)(OH)-CH$_2$-CH(CO$_2$H)-CH$_2$-CH$_2$-CO$_2$H | 54.50 |
| n-butyl-P(=O)(OH)-CH$_2$-CH(CO$_2$H)-CH$_2$-CH$_2$-CO$_2$H | 113.50 |
| m-tolyl-P(=O)(OH)-CH$_2$-CH(CO$_2$H)-CH$_2$-CH$_2$-CO$_2$H | 180.00 |
| phenethyl-P(=O)(OH)-CH$_2$-CH(CO$_2$H)-CH$_2$-CH$_2$-CO$_2$H | 148.50 |
| 3-phenylpropyl-P(=O)(OH)-CH$_2$-CH(CO$_2$H)-CH$_2$-CH$_2$-CO$_2$H | 231.67 |
| 4-fluorophenyl-P(=O)(OH)-CH$_2$-CH(CO$_2$H)-CH$_2$-CH$_2$-CO$_2$H | 532.00 |

TABLE III-continued

IN VITRO INHIBITION OF NAALADASE ACTIVITY

| Compound | $K_i$ (nM) |
|---|---|
| (methylphosphinyl)-substituted pentanedioic acid | 1100.00 |
| (4-methylbenzylphosphinyl)-substituted pentanedioic acid | 68.00 |
| (4-fluorobenzylphosphinyl)-substituted pentanedioic acid | 70.00 |
| (4-methoxybenzylphosphinyl)-substituted pentanedioic acid | 89.50 |
| (2-fluorobenzylphosphinyl)-substituted pentanedioic acid | 145.00 |
| (pentafluorobenzylphosphinyl)-substituted pentanedioic acid | 22.67 |
| (4-methylphenylphosphinyl)-substituted pentanedioic acid | 204.00 |

TABLE III-continued

IN VITRO INHIBITION OF NAALADASE ACTIVITY

| Compound | $K_i$ (nM) |
|---|---|
| 2-(phosphonomethyl)-4-phenylbutanoic acid derivative (phenethyl-CH₂-CH(CO₂H)-CH₂-P(O)(OH)₂) | 199.00 |
| 6-carboxy-2-(phosphonomethyl)hexanoic acid derivative | 185.00 |
| 4-benzyloxybenzyl phosphinic acid derivative | 177.00 |
| 3-(trifluoromethyl)benzyl phosphinic acid derivative | 22.50 |
| 2-(trifluoromethyl)benzyl phosphinic acid derivative | 92.00 |
| 4-hydroxybenzyl phosphinic acid derivative | 117.00 |

TABLE III-continued

IN VITRO INHIBITION OF NAALADASE ACTIVITY

| Compound | $K_i$ (nM) |
| --- | --- |
| | 740.0000 |
| | 198.5000 |
| | 4250.0000 |
| | 12.6667 |
| | 0.5700 |

TABLE III-continued

IN VITRO INHIBITION OF NAALADASE ACTIVITY

| Compound | $K_i$ (nM) |
|---|---|
| (structure) | 95.0000 |
| (structure) | 1.5000 |
| (structure) | 313.3 |
| (structure) | 2000.0 |
| (structure) | 51.8 |
| (structure) | 117.5 |

TABLE III-continued

IN VITRO INHIBITION OF NAALADASE ACTIVITY

| Compound | $K_i$ (nM) |
|---|---|
| dibenzylaminomethyl phosphinyl glutaric acid derivative | 175.0 |
| phthalimidomethyl phosphinyl glutaric acid derivative | 34.5 |
| phenylaminomethyl phosphinyl glutaric acid derivative | 6.3 |
| benzoylaminomethyl phosphinyl glutaric acid derivative | 142.0 |
| phenylsulfonylaminomethyl phosphinyl glutaric acid derivative | 90.0 |

TABLE III-continued

IN VITRO INHIBITION OF NAALADASE ACTIVITY

| Compound | $K_i$ (nM) |
|---|---|
| 4-fluoroanilinomethyl phosphinic acid pentanedioic derivative | 9.0 |
| 4-methoxyanilinomethyl phosphinic acid pentanedioic derivative | 2.5 |
| 4-methylanilinomethyl phosphinic acid pentanedioic derivative | 5.2 |
| 4-tert-butylanilinomethyl phosphinic acid pentanedioic derivative | 2.0 |
| phenylureidomethyl phosphinic acid pentanedioic derivative | 75.0 |
| 2-(2-sulfanylethyl)pentanedioic acid | 510.00 |

The results show that 2-(phosphonomethyl)pentane-dioic acid exhibits high NAALADase inhibiting activity, with a $K_i$ of 0.293 nM. The activity of this compound is over 1000 times greater than that of previously described NAALADase inhibitors.

By comparison, 2-(phosphonomethyl)succinic acid exhibits much lower NAALADase inhibiting activity, suggesting that a glutamate analog attached to the phosphonic acid contributes to its NAALADase inhibiting activity.

The results also show that 2-[[(2-carboxyethyl)-hydroxyphosphinyl]methyl]pentanedioic acid, which has an additional carboxylic acid side chain similar to the aspartate residue found in NAAG, exhibits a lower NAALADase inhibiting activity than 2-(phosphonomethyl)-pentanedioic acid.

In Viva Assay of Daily Dosages of NAALADase Inhibitors on Angiogenesis

C57B1 female mice age 8 to 10 weeks (5/group) were injected subcutaneously with 0.5 mL of Matrigel™, 150 ng/mL of the angiogenic factor basic FGF (bFGF) and with 0, 0.47 µM or 4.7 µM 2-(phosphono)pentanedioic acid (PMPA). The injected Matrigel™ rapidly formed a gel. On the same a day as the Matrigel™ injection, daily subcutaneous injections of 2-(phosphono)pentanedioic acid around the Matrigel™ plug were initiated. Seven days post Matrigel™ injection, Matrigel™ plugs were excised and histology was performed.

The concentrations of the daily dosages as well as the coinciding initial Matrigel™ plug compositions are provided below in TABLE IV.

TABLE IV

CONCENTRATIONS OF DAILY DOSAGES OF NAALADASE INHIBITORS

| Daily Subcutaneous Injection Concentration | Initial Concentrations in Matrigel ™ |
|---|---|
| Vehicle | 50 mM Hepes |
| 3 mg/kg | 0.47 µM PMPA in 50 mM Hepes |
| 30 mg/kg | 4.7 µM PMPA in 50 mM Hepes |

As detailed in FIG. 1/Row 1, a good angiogenic response was observed in the vehicle dose group. The resultant decrease in blood vessels or angiogenesis in the Matrigel™ plugs from the 3 mg/kg and 30 mg/kg daily dose groups is shown in FIG. 1/Row 2 and FIG. 1/Row 3, respectively.

In Vivo Assay of a Continuous Dosage of NAALADase Inhibitors on Angiogenesis

Miniosmotic pumps were implanted into C57B1 female mice (5/group) at the PMPA concentrations shown in TABLE V below. Minipumps filled with vehicle (50 mM Hepes) were also implanted at this time. Twenty-four hours later, mice were each injected subcutaneously with 0.5 mL Matrigel™ and the 150 ng/mL of the angiogenic factor, basic FGF (bFGF). Thirteen days post Matrigel™/bFGF injection, the gels were recovered, fixed in formalin and sections were stained with Trichrome-Masson stain.

TABLE V

CONCENTRATIONS OF CONTINUOUSLY ADMINISTERED DOSAGES OF NAALADASE INHIBITORS

PMPA Released by Minipump

| |
|---|
| 50 mN Hepes |
| 1 µg/day |
| 10 µg/day |
| 100 µg/day |

Figure 2:
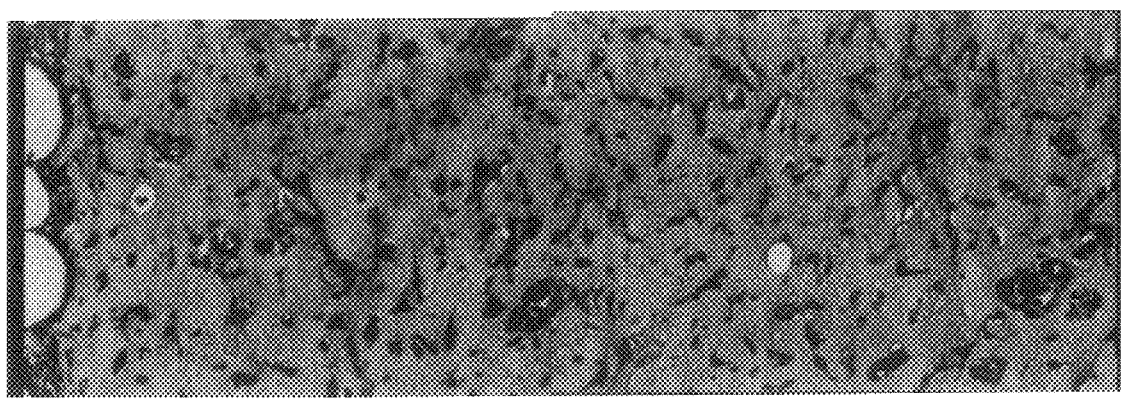
FIG. 2 is a microphotograph of a Matrigel™ plug subcutaneously injected into a mouse and treated with a continuous concentration dosage of a vehicle alone following injection of an angiogenic factor.
Figure 3:
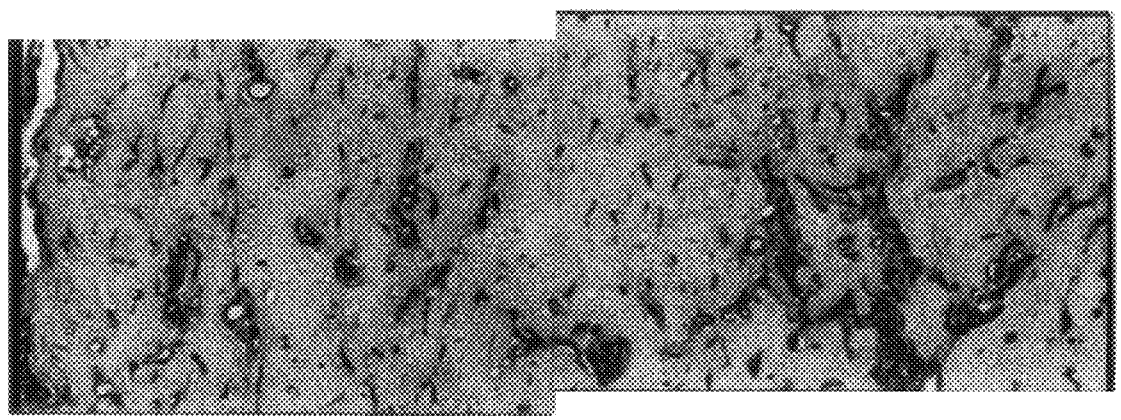
FIG. 3 is a microphotograph of a Matrigel™ plug subcutaneously injected into a mouse and treated with a 1 μg/day continuous dosage of 2-(phosphono)pentanedioic acid following injection of an angiogenic factor.
Figure 4:
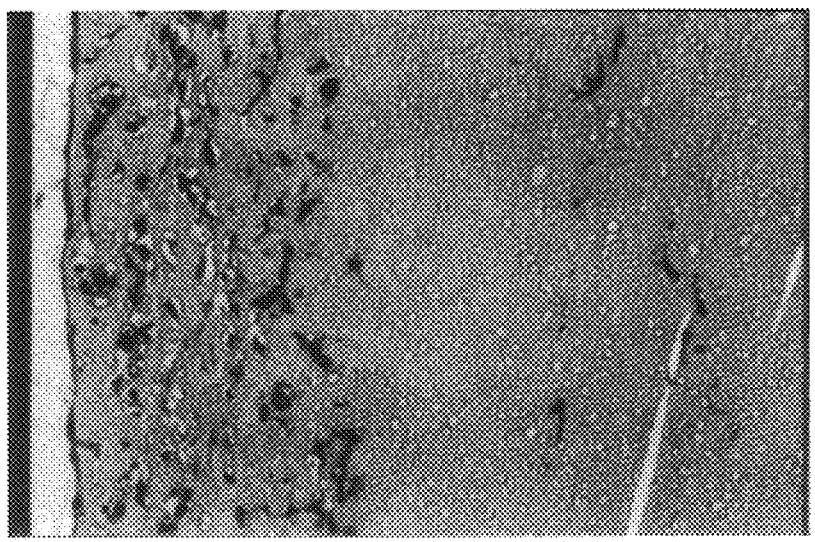
FIG. 4 is a microphotograph of a Matrigel™ plug subcutaneously injected into a mouse and treated with a 10 μg/day continuous dosage of 2-(phosphono)pentanedioic acid following injection of an angiogenic factor.
Figure 5:
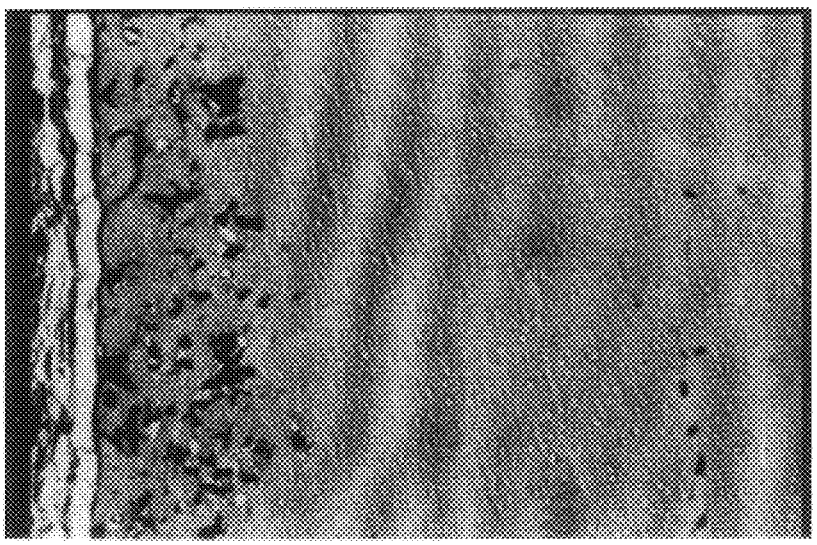
FIG. 5 is a microphotograph of a Matrigel™ plug subcutaneously injected into a mouse and treated with a 100 μg/day continuous dosage of 2-(phosphono)pentanedioic acid following injection of an angiogenic factor.

A strong angiogenic response was observed in the vehicle and 1 µg/day dose group, as shown in FIGS. 2 and 3, respectively. As detailed in FIGS. 4 and 5, respectively, delivery of 10 µg/day and 100 µg/day of PMPA significantly decreased angiogenesis in the Matrigel™/bFGF gels.

EXAMPLES

The following examples are illustrative of the present invention and are not intended to be limitations thereon. Unless otherwise indicated, all percentages are based upon 100% by weight of the final composition.

Example 1

Preparation of 2-[(methylhydroxyphosphinyl) methyl]pentanedioic acid

Scheme VII: R=CH$_3$, R$_1$=CH$_2$Ph

Methyl-O-benzylphosphinic acid

Dichloromethylphosphite (10.0 g, 77 mmol) in 80 mL of dry diethyl ether was cooled to −20° C. under an atmosphere of nitrogen. A solution of benzyl alcohol (23 g, 213 mmol) and triethylamine (10.2 g, 100 mmol) in 40 mL of diethyl ether was added dropwise over 1 hour while maintaining an internal temperature range of 0° C. to 10° C. Once addition was complete the mixture was warmed to room temperature and stirred overnight. The mixture was filtered and the solid cake washed with 200 mL of diethyl ether. The organics were combined and evaporated under reduced pressure to give 25 g of a clear and colorless liquid. The liquid was purified by flash chromatography and eluted with a 1:1 hexane/ethyl acetate to ethyl acetate gradient. The desired fractions were collected and evaporated to give methyl-O-benzylphosphinic acid (1, R=CH$_3$, R$_1$=CH$_2$Ph, 6.5 g, 50%) as a clear and colorless oil. Rf 0.1 (1:1, Hexane/EtOAc).

$^1$H NMR (d6-DMSO): 7.4 ppm (m, 5H), 7.1 ppm (d, 1H), 5.0 ppm (dd, 2H), 1.5 ppm (d, 3H)

2,4-Di(benzyloxycarbonyl)butyl(methyl)-O-benzylphosphinic acid

Methyl-O-benzylphosphinic acid (3.53 g, 20.7 mmol) in 200 mL of dichloromethane was cooled to −5° C. under an atmosphere of nitrogen. Triethylamine (3.2 g, 32 mmol) was added via syringe followed by trimethylsilyl chloride (2.9 g, 27 mmol). The reaction mixture was stirred and warmed to room temperature over 1 hour. Dibenzyl 2-methylenepentanedioate (2, 6.0 g, 18.5 mmol) in 10 mL of dichloromethane was added. The mixture was then stirred at room temperature overnight. The reaction mixture was cooled to 0° C. and trimethylaluminum (9 mL, 18 mmol, 2.0 M in dichloromethane) was added. The flask was warmed and stirred for 72 hours. The clear light yellow solution was cooled to 5° C. and quenched by the slow addition of 5% hydrochloric acid. The quenched reaction mixture was warmed to room temperature and the organic layer removed. The organic layer was washed with 5% hydrochloric acid and with water. The organics were dried (MgSO$_4$) and evaporated under reduced pressure to give 8 g of a clear light yellow oil. The oil was purified on silica gel and eluted with a gradient of 1:1 hexanes/ethyl acetate to 100% ethyl acetate. The desired fractions were collected and evaporated to give 2,4-di(benzyloxycarbonyl)butyl(methyl)-O-benzylphosphinic acid (3, R=CH$_3$, R$_1$=CH$_2$Ph, 0.8 g, 8%) as a clear and colorless oil. Rf 0.5 (ethyl acetate).

$^1$H NMR (CDCl$_3$): 7.4 ppm (m, 15H), 5.1 ppm (m, 6H), 3.0 ppm (m, 1H), 2.4 ppm (m, 3H), 2.1 ppm (m, 3H), 1.5 ppm (dd, 3H).

Elemental Analysis Calculated C$_{28}$H$_{31}$O$_6$P, 0.5 H$_2$O: C, 68.01; H, 6.32. Found: C, 66.85; H, 6.35.

2-[(Methylhydroxyphosphinyl)methyl]pentanedioic acid 2,4-di(benzyloxycarbonyl)butyl(methyl)-O-benzylphosphinic acid (0.8 g, 1.6 mmol) in 20 mL of water containing 100 mg of 10% Pd/C was hydrogenated at 40 psi for 4 hours. The mixture was filtered over a pad of Celite and evaporated at high vacuum to give 2-[(methylhydroxyphosphinyl)methyl]pentanedioic acid (4, R=CH$_3$, 0.28 g), 78% as a clear and colorless viscous oil.

$^1$H NMR (D$_2$O): 2.5 ppm (m, 1H), 2.2 ppm (t, 2H), 2.0 ppm (m, 1H), 1.7 ppm (m, 3H), 1.3 ppm (d, 3H). Elemental Analysis Calculated C$_7$H$_{13}$O$_6$P, 0.2 H$_2$O: C, 36.92; H, 5.93. Found: C, 37.06; H, 6.31.

Example 2

Preparation of 2-[butylhydroxyphosphinyl)methyl]pentanedioic acid
Scheme VII: R=n-butyl, R$_1$=H Butylphosphinic Acid Diethyl chlorophosphite (25 g, 0.16 mol) in 60 mL of dry ether was cooled to 0° C. under an atmosphere of nitrogen. Butylmagnesium chloride (80 mL, 0.16 mol, 2.0 M solution in ether) was added dropwise over a period of 2 hours while maintaining the internal temperature at 0° C. Once addition was complete the thick white slurry was heated to 30° C. for 1 hour. The suspension was filtered under a nitrogen atmosphere and the filtrate evaporated under reduced pressure. The clear light yellow liquid was then brought up in 15 mL of water and stirred at room temperature. Concentrated hydrochloric acid (0.5 mL) was then added and an exothermic reaction was observed. The mixture was stirred an additional 15 minutes and extracted with two 75 mL portions of ethyl acetate. The organics were combined, dried (MgSO$_4$) and evaporated to give a clear and colorless liquid. The liquid was treated with NaOH (40 mL, 2.0 M) and stirred for 1 hour. The mixture was then washed with diethyl ether and acidified to pH 1.0. The desired material was extracted from the acidified extract with two 100 mL portions of ethyl acetate. The organics were combined, dried (MgSO$_4$) and evaporated under reduced pressure to give butylphosphinic acid (1, R=n-butyl, R$_1$=H, 10 g, 51%) as a clear and colorless liquid.

$^1$H NMR (d6-DMSO): 6.9 ppm (d, 1H), 1.6 ppm (m, 2H), 1.4 ppm (m, 4H), 0.9 ppm (t, 3H).

Butyl[2,4-di(benzyloxycarbonyl)butyl]phosphinic acid

Butylphosphinic acid (2.0 g, 16 mmol) in 80 mL of dry dichloromethane was cooled to 0° C. under an atmosphere of nitrogen. Triethylamine (6.7 g, 66 mmol) was added followed by trimethylsilyl chloride (58 mL, 58 mmol, 1.0 M in dichloromethane). The mixture was stirred at 0° C. for 10 minutes and dibenzyl 2-methylenepentanedioate (2)(6.4 g, 20 mmol) in 20 mL of dichloromethane was added. The cold bath was removed and the reaction warmed to room temperature and stirred overnight. The mixture was then cooled to 0° C. and quenched by the slow addition of 5% hydrochloric acid (50 mL). The dichloromethane layer was then removed and washed with 5% hydrochloric acid and with brine. The organic layer was dried (MgSO$_4$) and evaporated to give a clear light golden liquid. The liquid was purified by flash chromatography and eluted with 3:1 hexane/ethyl acetate containing 5% acetic acid. The desired fractions were combined and evaporated to give butyl[2,4-di(benzyloxycarbonyl)butyl]phosphinic acid (3, R=n-butyl, R$_1$=H) (2.9 g, 40%) as a clear and colorless oil. Rf 0.12 (3:1 Hexane/EtOAc, 5% AcOH).

$^1$H NMR (d6-DMSO): 7.3 ppm (m, 10H), 5.0 ppm (s, 4H), 2.7 ppm (m, 1H), 2.3 ppm (t, 2H), 1.8 ppm (m, 2H), 1.3 ppm (m, 4H), 0.8 ppm (t, 3H).

2-[(Butylhydroxyphosphinyl)methyl]pentanedioic acid

Butyl[2,4-di(benzyloxycarbonyl)butyl]phosphinic acid (2.9 g, 6.5 mmol) in 30 mL of water containing 0.32 g 10% Pd/C was hydrogenated at 40 psi for 4.5 hours. The mixture was filtered through a pad of Celite and evaporated under high vacuum to give 2-[(butylhydroxyphosphinyl)methyl]pentanedioic acid (4, R=n-butyl)(0.75 g, 43%) as a clear and colorless viscous oil.

$^1$H NMR (D$_2$O): 2.4 ppm (m, 1H), 2.1 ppm (t, 2H), 1.9 ppm (m, 1H), 1.6 ppm (m, 3H), 1.4 ppm (m, 2H), 1.1 ppm (m, 4H), 0.6 ppm (t, 3H).

Elemental Analysis Calculated C$_{10}$H$_{19}$O$_6$P, 0.5 H$_2$O: C, 43.64; H, 7.32. Found: C, 43.25; H, 7.12.

Example 3

Preparation of 2-[(benzylhydroxyphosphinyl)methyl]pentanedioic acid
Scheme VII: R=CH$_2$Ph, R$_1$=H Benzylphosphinic acid Diethylchlorophosphite (25 g, 0.16 mol) in 100 mL of dry diethyl ether was cooled to 0° C. under an atmosphere of nitrogen. Benzylmagnesium chloride (80 mL, 0.16 mol, 2.0 M solution in Et$_2$O) was added dropwise over two hours while maintaining a temperature below 10° C. A thick white slurry formed and stirring was continued at room temperature for 1 hour. The mixture was filtered under a nitrogen atmosphere and the filtrate evaporated under reduced pressure to give a clear and colorless liquid. The liquid was stirred as 15 mL of water was added followed by 0.5 mL concentrated hydrochloric acid. An exothermic reaction was observed and stirring was continued for an additional 30 minutes followed by extraction with ethyl acetate. The organics were combined, washed with brine, dried (MgSO$_4$) and evaporated. The clear light golden liquid was added to sodium hydroxide (50 mL, 2.0 M NaOH), stirred for 1 hour and washed with diethyl ether. The aqueous layer was acidified to pH 1.0 with concentrated hydrochloric acid and extracted with ethyl acetate. The organics were combined, dried (MgSO$_4$) and evaporated to give benzylphosphinic acid (1, R=CH$_2$Ph, R$_1$=H) (8 g, 32%) as a clear light golden oil.

$^1$H NMR (d6-DMSO): 7.3 ppm (m, 5H), 6.9 ppm (d, 1H), 3.1 ppm (d, 2H).

Benzyl[2,4-di(benzyloxycarbonyl)butyl]phosphinic acid

Benzylphosphinic acid (2.3 g, 15 mmol) in 150 mL of dry dichloromethane was cooled to 0° C. under a nitrogen atmosphere. Triethylamine (6.5 g, 65 mmol) was added followed by trimethylsilyl chloride (5.8 g, 54 mmol) while the reaction temperature was maintained at 0° C. After 30 minutes dibenzyl 2-methylene-pentanedioate (2) (4.4 g, 13.6 mmol) in 20 mL of dichloromethane was added over 5 minutes. The reaction mixture was allowed to warm to room temperature and stirred overnight. The clear solution was cooled to 0° C. and quenched with 5% hydrochloric acid followed by removal of the organic layer. The organic layer was washed with 5% hydrochloric acid and with brine, dried (MgSO$_4$) and evaporated to give a clear yellow liquid. Purification by flash chromatography and elution with 1:1 hexane/ethyl acetate containing 10% acetic acid yielded 2.0 g (28%) of benzyl[2,4-di(benzyloxycarbonyl)butyl]phosphinic acid (3, R=CH$_2$Ph, R$_1$=H) as a clear light yellow oil. Rf 0.37 (1:1 Hexane/EtOAc, 10% AcOH).

$^1$H NMR (d6-DMSO): 7.2 ppm (m, 15H), 5.0 ppm (s, 4H), 3.0 (d, 2H), 2.8 ppm (m, 1H), 2.3 ppm (t, 2H), 1.9 ppm (m, 2H), 1.7 ppm (t, 1H).

2-[(Benzylhydroxyphosphinyl)methyl]pentanedioic acid

Benzyl [2,4-di(benzyloxycarbonyl)butyl]phosphinic acid (0.5 g, 1.0 mmol) in 20 mL of water containing 120 mg of 10% Pd/C was hydrogenated at 40 psi for 6 hours. Filtration through a Celite pad followed by evaporation on high vacuum gave 0.17 g (57%) of 2-[(benzylhydroxyphosphinyl)methyl]-pentanedioic acid (4, R=CH$_2$Ph) as a white solid.

$^1$H NMR (D$_2$O): 7.1 ppm (m, 5H), 2.9 ppm (d, 2H), 2.4 ppm (m, 1H), 2.1 ppm (t, 2H), 1.8 ppm (m, 1H), 1.6 ppm (m, 3H).

Elemental Analysis Calculated C$_{13}$H$_{17}$O$_6$P: C, 52.00; H, 5.71. Found: C, 51.48; H, 5.70.

Example 4

Preparation of 2-[phenylethylhydroxyphosphinyl)methyl]pentanedioic acid
Scheme VII: R=CH$_2$CH$_2$Ph, R$_1$=H

Phenethylphosphinic acid

Diethylchlorophosphite (15.6 g, 0.1 mol) in 100 mL of dry diethyl ether was cooled to 5° C. under an atmosphere of nitrogen. Phenethylmagnesium chloride (100 mL, 0.1 mol, 1.0 M in THF) was added dropwise over 2 hours while maintaining a temperature between 0–10° C. A thick white slurry formed and stirred at room temperature overnight. The mixture was filtered under a nitrogen atmosphere and the filtrate evaporated under reduced pressure to give a clear and colorless liquid. The liquid was stirred as 15 mL of water was added followed by 0.5 mL of concentrated hydrochloric acid. An exothermic reaction was observed and stirring continued for 15 minutes followed by extraction with ethyl acetate. The organics were combined, washed with brine, dried (MgSO$_4$) and evaporated. The clear liquid was brought up in sodium hydroxide (40 mL, 2.0 M NaOH), stirred for 1 hour and washed once with diethyl ether. The aqueous layer was acidified to pH 1.0 with concentrated hydrochloric acid and extracted with ethyl acetate. The organics were combined, dried (MgSO$_4$) and evaporated to give phenethylphosphinic acid (1, R=CH$_2$CH$_2$Ph, R$_1$=H)(9.8 g, 58%) as a clear light yellow oil.

$^1$H NMR (d6-DMSO): 7.2 ppm (m, 5H), 6.9 ppm (d, 1H), 2.8 ppm (m, 2H), 1.9 ppm (m, 2H).

2,4-Di(benzyloxycarbonyl)butyl(phenethyl)phosphinic acid

Phenethylphosphinic acid (1.0 g, 5.9 mmol) in 50 mL of dry dichloromethane was cooled to –5° C. under a nitrogen atmosphere. Triethylamine (2.3 g, 23 mmol) was added followed by trimethylsilyl chloride (2.2 g, 21 mmol) while the reaction temperature was maintained at 0° C. After 10 minutes dibenzyl 2-methylenepentanedioate (2)(1.7 g, 5.2 mmol) in 10 mL of dichloromethane was added over 10 minutes. The reaction mixture was left to warm to room temperature and stirred overnight. The clear solution was cooled to 0° C. and quenched with 5% hydrochloric acid followed by removal of the organic layer. The organic layer was washed with brine, dried (MgSO4) and evaporated to give a clear light golden liquid. Purification by flash chromatography and elution with 1:1 Hexane/EtOAc containing 5% AcOH yielded 1.2 g (41%) of 2,4-di(benzyloxycarbonyl)-butyl(phenethyl)phosphinic acid (3, R=CH$_2$CH$_2$Ph, R$_1$=H) as a clear and colorless oil.

$^1$H NMR (d6-DMSO): 7.2 ppm (m, 15H), 5.0 ppm (s, 4H), 3.3 ppm (m, 1H), 2.8 ppm (m, 4H), 2.3 ppm (m, 2H), 1.8 ppm (m, 4H).

2-[(Phenethylhydroxyphosphinyl)methyl]pentanedioic acid 2,4-Di(benzyloxycarbonyl)butyl(phenethyl)phosphinic acid (1.1 g, 2.2 mmol) in 20 mL of water containing 120 mg of 10% Pd/C was hydrogenated at 40 psi overnight. Filtration through a Celite pad followed by evaporation on high vacuum gave 0.8 g (114%) of 2-[(phenethylhydroxyphosphinyl)methyl]pentanedioic acid (4, R=CH$_2$CH$_2$Ph) as a white solid.

$^1$H NMR (D$_2$O): 7.2 ppm (m, 5H), 2.7 ppm (m, 2H), 2.5 ppm (m, 1H), 2.3 ppm (t, 2H), 1.9 ppm (m, 6H), 1.5 ppm (t, 1H)

Elemental Analysis Calculated C$_{14}$H$_{19}$O$_6$P, 0.75 H$_2$O, 0.5 AcOH: C, 50.35; H, 6.34. Found: C, 50.26; H, 5.78.

Example 5

Preparation of 2-[(3-phenylpropylhydroxyphosphinyl)methyl]pentanedioic acid
Scheme VII: R=CH$_2$CH$_2$CH$_2$Ph, R$_1$=H

3-Phenylpropylphosphinic acid

To magnesium turnings (2.44 g, 0.10 mol) in 20 mL of dry diethyl ether under an atmosphere of nitrogen was added several iodine crystals. Phenylpropyl bromide (20.0 g, 0.10 mol) in 80 mL of diethyl ether was placed in a dropping funnel. Approximately 10 mL of the bromide solution was added to the magnesium turnings and stirring was initiated. After several minutes the iodine was consumed and additional phenylpropyl bromide was added while maintaining a temperature of 35° C. Once addition was complete (1.5 hours) the mixture was sealed and stored at 5° C.

Diethylchlorophosphite (15.7 g, 0.1 mol) in 50 mL of dry diethyl ether was cooled to 5° C, under an atmosphere of nitrogen. Phenethylmagnesium bromide (100 mL, 0.1 mol, 1.0 M solution of in $Et_2O$) was added dropwise over 2 hours while maintaining a temperature between 0–10° C. A thick white slurry formed and was stirred for an additional 30 minutes. The mixture was filtered under a nitrogen atmosphere and the filtrate evaporated under reduced pressure to give a clear and colorless liquid. To the liquid was added 20 mL of water followed by 0.5 mL of concentrated hydrochloric acid. An exothermic reaction was observed and stirring continued for 20 minutes followed by extraction with ethyl acetate. The organics were combined, washed with brine, dried ($MgSO_4$) and evaporated. To the clear liquid was added sodium hydroxide (40 mL, 2.0 M NaOH), the resulting solution stirred for 1 hour and then washed with diethyl ether. The aqueous layer was acidified to pH 1.0 with concentrated hydrochloric acid and extracted twice with ethyl acetate. The organics were combined, dried ($MgSO_4$) and evaporated to give 3-phenylpropylphosphinic acid (1, $R=CH_2CH_2CH_2Ph$, $R_1=H$) (9.8 g, 53%) as a clear and colorless oil.

$^1$H NMR (d6-DMSO): 7.2 ppm (m, 5H), 6.9 ppm (d, 1H), 2.6 ppm (t, 2H), 1.7 ppm (m, 2H), 1.6 ppm (m, 2H).

2,4-Di(benzyloxycarbonyl)butyl(3-phenylpropyl) phosphinic acid 3-phenylpropylphosphinic acid (1.0 g, 5.4 mmol) in 50 mL of dry dichloromethane was cooled to –5° C. under a nitrogen atmosphere. Triethylamine (2.2 g, 22 mmol) was added followed by trimethylsilyl chloride (2.1 g, 19 mmol) while the reaction temperature was maintained at 0° C. After 10 minutes dibenzyl 2-methylenepentanedioate (2)(1.6 g, 4.9 mmol) in 10 mL of dichloromethane was added over 10 minutes. The reaction mixture was warmed to room temperature and stirred overnight. The clear solution was cooled to 0° C. and quenched with 5% hydrochloric acid followed by removal of the organic layer. The organic layer was washed with brine, dried ($MgSO_4$) and evaporated to give a clear yellow liquid. Purification by flash chromatography and elution with 4:1 hexane/ethyl acetate containing 5% acetic acid resulted in 1.5 g (56%) of 2,4-di (benzyloxycarbonyl)-butyl(3-phenylpropyl)phosphinic acid (3, $R=CH_2CH_2CH_2Ph$, $R_1=H$) as a clear light yellow oil. Rf 0.58 (1:1 Hexane/EtOAc, 5% AcOH).

$^1$H NMR (d6-DMSO): 7.2 ppm (m, 15H), 5.0 ppm (s, 4H), 2.7 ppm (m, 1H), 2.5 ppm (m, 5H), 2.2 ppm (m, 2H), 1.8 ppm (m, 3H), 1.6 ppm (m, 2H).

Elemental Analysis Calculated $C_{29}H_{33}O_6P$, 1.3 $H_2O$: C, 65.48; H 6.75. Found: C, 65.24; H, 6.39.

2-[(3-Phenylpropylhydroxyphosphinyl)methyl] pentanedioic acid 2,4-Di(benzyloxycarbonyl)butyl(3-phenylpropyl) phosphinic acid (1.4 g, 2.8 mmol) in 20 mL of water containing 150 mg of 10% Pd/C was hydrogenated at 40 psi overnight. Filtration through a Celite pad followed by evaporation on high vacuum gave 0.8 g (89%) of 2-[(3-phenylpropylhydroxyphosphinyl)methyl]pentanedioic acid (4, $R=CH_2CH_2CH_2Ph$) as a light yellow viscous oil.

$^1$H NMR ($D_2O$): 7.4 ppm (m, 5H), 2.7 ppm (m, 3H), 2.4 ppm (t, 3H), 1.8 ppm (m, 7H).

Elemental Analysis Calculated $C_{15}H_{21}O_6P$, 0.75 $H_2O$, 0.75 AcOH: C, 51.23; H, 6.64. Found: C, 50.85; H, 6.02.

Example 6

Preparation of 2-[[(4-methylbenzyl) hydroxyphosphinyl]methyl]pentanedioic acid
Scheme VIII: Compound 5, R=4-methylbenzyl Hexamethyldisilazane (21.1 mL, 100 mmol) was added to vigorously stirred ammonium phosphinate (8.30 g, 100 mmol), and the resulting suspension was stirred at 105° C. for 2 hours. A solution of 4-methylbenzyl bromide (5.0 g, 27.0 mmol) was then added dropwise to the suspension at 0° C. The mixture was stirred at room temperature for 19 hours. The reaction mixture was then diluted with dichloromethane (50 mL) and washed with 1 N HCl (50 mL). The organic layer was separated, dried over $Na_2SO_4$, and concentrated to give 4.72 g of a white solid. This was dissolved in dichloromethane (50 mL) and benzyl alcohol (3.24 g, 30 mmol) was added to the solution. 1,3-Dicyclohexylcarbodiimide (DCC)(6.19 g, 30 mmol) was then added to the solution at 0° C., and the suspension was stirred at room temperature for 14 hours. The solvent was removed under reduced pressure and the residue was suspended in EtOAc. The resulting suspension was filtered and the filtrate was concentrated. The residue was purified by silica gel chromatography (hexanes: EtOAc, 4:1 to 1:1) to give 2.40 g of 4-methylbenzyl-O-benzylphosphinic acid (2, R=4-methylbenzyl) as a white solid (34% yield). Rf 0.42 (EtOAc).

$^1$H NMR (d6-DMSO): δ2.30 (s, 3H), 3.29 (d, 2H), 5.2 (m, 2H), 7.0 (d, 1H), 7.1–7.2 (m, 4H), 7.3–7.4 (m, 5H).

2,4-Di(benzyloxycarbonyl)-butyl(4-methylbenzyl)-o-benzylphosphinic acid

To a solution of 4-methylbenzyl-O-benzylphosphinic acid (2, R=4-methylbenzyl) (2.16 g, 8.3 mmol) in THF (15 mL) was added sodium hydride (0.10 g, 60% dispersion in oil) followed by dibenzyl 2-methylenepentanedioate (3) (3.24 g) at 0° C., and the mixture was stirred at room temperature for 4 hours. The reaction mixture was then diluted with EtOAc (50 mL) and poured into 1 N HCl (50 mL). The organic layer was separated, dried over $Na_2SO_4$, and concentrated. This material was purified by silica gel chromatography (hexanes: EtOAc, 4:1 to 1:1) to give 3.41 g of 2,4-di (benzyloxycarbonyl)-butyl(4-methylbenzyl)-o-benzylphosphinic acid (4, R=4-methylbenzyl) as colorless oil (70% yield). Rf 0.61 (EtOAc).

$^1$H NMR ($CDCl_3$): δ1.6–1.8 (m, 1H), 1.9–2.0 (m, 2H), 2.1–2.4 (m, 6H), 2.7–2.9 (m, 1H), 3.05 (dd, 2H), 4.8–5.1 (m, 6H), 7.0–7.1 (m, 4H), 7.2–7.4 (m, 15H).

2-[[(4-Methylbenzyl)hydroxyphosphinyl]methyl] pentanedioic acid

To a solution of 2,4-di(benzyloxycarbonyl)butyl (4-methylbenzyl)-o-benzylphosphinic acid (0.70 g, 1.2 mmol) in ethanol (30 mL) was added Pd/C (5%, 0.10 g) and the suspension was shaken under hydrogen (50 psi) for 18 hours. The suspension was then filtered through a pad of Celite and concentrated under reduced pressure. The resulting residue was dissolved in distilled water (5 ml), passed through a column of AG 50W-X8 resin ($H^+$ form), and lyophilized to give 0.21 g of 2-[[4 -methylbenzyl) hydroxyphosphinyl]methyl]-pentanedioic acid (5, R=4-methylbenzyl) as a white solid (55% yield). Rf 0.62 (i-PrOH: $H_2O$, 7:3).

$^1$H NMR ($D_2O$): δ1.7–1.9 (m, 3H), 2.0–2.2 (m, 1H), 2.33 (dt, 7.4 Hz, 2H), 2.55–2.70 (m, 1H), 3.12 (d, 2H), 7.0–7.1 (m, 2H), 7.2–7.3 (m, 2H). Elemental Analysis Calculated $C_{13}H_{17}O_6P$, 0.30 $H_2O$: C, 52.60; H, 6.18. Found: C, 52.60; H, 6.28.

Example 7

Preparation of 2-[[(4-Fluorobenzyl) hydroxyphosphinyl]methyl]pentanedioic acid
Scheme VIII: R=4-fluorobenzyl Prepared as described in the above example where R=methylbenzyl. Rf 0.64 (i-PrOH:$H_2O$, 7:3).

¹H NMR (D₂O): δ1.7–1.9 (m, 3H), 2.0–2.2 (m, 1H), 2.3–2.4 (m, 2H), 2.55–2.70 (m, 1H), 3.12 (d, 2H), 7.0–7.1 (m, 2H), 7.2–7.3 (m, 2H).

Elemental Analysis Calculated $C_{13}H_{16}FO_6P$, 0.25 $H_2O$: C, 48.38; H, 5.15. Found: C, 48.38; H, 5.15.

Example 8

Preparation of 2-[[(4-Methoxybenzyl)hydroxyphosphinyl]methyl]pentanedioic acid

Scheme VIII: R=4-methoxybenzyl

Prepared as described in the above example where R=methylbenzyl. Rf 0.56 (i-PrOH: H₂O, 7:3).

¹H NMR (D₂O): δ1.8–1.9 (m, 3H), 2.0–2.2 (m, 1H), 2.3–2.4 (m, 2H), 2.55–2.70 (m, 1H), 3.16 (d, 2H), 3.81 (s, 3H), 6.98 (d, 2H), 7.25 (d, 2H).

Elemental Analysis Calculated $C_{14}H_{19}O_7P$, 0.30 $H_2O$: C, 50.09; H, 5.89. Found: C, 49.98; H, 5.80.

Example 9

Preparation of 2-[[(2-Fluorobenzyl)hydroxyphosphinyl]methyl]pentanedioic acid

Scheme VIII: R=2-fluorobenzyl

Prepared as described in the above example where R=methylbenzyl. Rf 0.67 (i-PrOH: H₂O, 7:3).

¹H NMR (D₂O): δ1.8–1.9 (m, 3H), 2.0–2.2 (m, 1H), 2.3–2.4 (m, 2H), 2.55–2.70 (m, 1H), 3.28 (d, 2H), 7.1–7.5 (m, 4H).

Elemental Analysis Calculated $C_{13}H_{16}FO_6P$, 0.10 $H_2O$: C, 48.79; H, 5.10. Found: C, 48.84; H, 5.14.

Example 10

Preparation of 2-[[(Pentafluorobenzyl)hydroxyphosphinyl]methyl]pentanedioic acid Scheme VIII: R=pentafluorobenzyl Prepared as described in the above example where R=methylbenzyl. Rf 0.69 (i-PrOH: H₂O, 7:3).

1H NMR (D₂O): δ1.8–2.0 (m, 3H), 2.1–2.3 (m, 1H), 2.3–2.5 (m, 2H), 2.7–2.9 (m, 1H), 3.29 (d, 2H).

Elemental Analysis Calculated $C_{13}H_{12}F_5O_6P$, 0.45 $H_2O$: C, 39.20; H, 3.26. Found: C, 39.17; H, 3.28.

Example 11

Preparation of 2-[(methylhydroxyphosphinyl)methyl]pentanedioic acid

Scheme IX, Compound 9

2,4-Di(benzyloxycarbonyl)butylphosphinic acid (6)

Dry phosphinic acid (100 g, 1.52 mol) was dissolved in 100 mL of chloroform and treated with triethylamine (155 g, 1.52 mol). The mixture was evaporated and transferred to a three liter flask containing 750 mL of chloroform. The solution was stirred by means of a mechanical stirrer and the flask cooled to 0° C. The clear solution was treated with triethylamine (277 g, 2.72 mol) followed by trimethylsilyl chloride (281 g, 2.58 mol). Once addition of trimethylsilyl chloride was complete dibenzyl 2-methylenepentanedioate (2) in 150 mL of chloroform was added dropwise over 20 minutes. The low temperature bath was removed and the mixture warmed to room temperature. After 6 hours the thick slurry was filtered and the filtrate cooled to 0° C. The filtrate was then quenched with 5% hydrochloric acid and the organic layer removed. The aqueous layer was extracted with chloroform, the organics combined, dried (MgSO₄) and evaporated under reduced pressure to give 55 g or 2,4-di(benzyloxycarbonyl)butylphosphinic acid (6) as a light yellow liquid. The liquid was purified by flash chromatography and eluted using 3:1 hexanes/ethyl acetate containing 5% trifluoroacetic acid to give 40 g (7%) of the desired product. Rf 0.28 (3:1 Hexane/EtOAc 5% TFA).

¹H NMR (CDCl₃): 7.3 ppm (m, 10H), 7.2 ppm (d, 1H), 5.12 ppm (s, 2H), 2.9 ppm (m, 1H), 2.4 ppm (t, 2H), 2.2 ppm (m, 1H), 2.0 ppm (m, 3H)

2,4-Di(benzyloxycarbonyl)butylbenzylphosphinic acid (7)

To a solution of 2,4-di-(benzyloxycarbonyl)butylphosphinic acid (6) (19.3 g, 49.4 mmol) in tetrahydrofuran was added benzyl alcohol (5.3 g, 49.3 mmol) and dimethylamino pyridine (0.5 g). Dicyclohexylcarbodiimide (DCC, 12 g, 58 mmol) was added and a white precipitate formed. After 30 minutes the white suspension was filtered and the filtrate evaporated under reduced pressure. The clear and colorless oil was purified by flash chromatography and eluted with 1:1 Hexane/EtOAc to give 2,4-di(benzyloxycarbonyl)butylbenzylphosphinic acid (7) (11.5 g, 47%) as a clear and colorless oil. Rf 0.16 (1:1 Hexane/EtOAc).

¹NMR (CDCl₃): 7.3 ppm (m, 15H), 7.2 ppm (d, 1H), 5.0 ppm (m, 6H), 2.9 ppm (m, 1H), 2.2 ppm (m, 3H), 1.9 ppm (m, 3H).

2,4-Di(benzyloxycarbonyl)butyl[hydroxy(phenyl)methyl]benzylphosphinic acid (8)

2,4-Di(benzyloxycarbonyl)butylbenzylphosphinic acid (7) in 5 mL of dry THF was added dropwise to a stirring cooled (0° C.) mixture of sodium hydride (0.09 g, 2.3 mmol) in 15 mL of THF. After 15 minutes benzaldehyde (0.23 g, 2.2 mmol) was added via syringe while maintaining a temperature of 0° C. After 30 minutes the mixture was quenched with water and extracted with two portions of dichloromethane. The organics were combined and evaporated to give a clear colorless oil. The oil was chromatographed on silica and eluted with a 1:1 Hexane/EtOAc solvent system. The desired fractions were collected and evaporated to give 0.4 g (33%) of 2,4-di(benzyloxycarbonyl)butyl[hydroxy(phenyl)methyl]benzylphosphinic acid (6) as a clear and colorless oil. Rf 0.18 (1:1 Hexane/EtOAc).

¹H NMR (CDCl₃): 7.3 ppm (m, 20H), 5.2 ppm (m, 1H), 4.9 ppm (m, 6H), 2.8 ppm (dm, 1H), 2.2 ppm (m, 3H), 1.9 ppm (m, 3H).

2-([Hydroxy(phenyl)methyl]hydroxyphosphinylmethyl)pentanedioic acid (9)

2,4-Di(benzyloxycarbonyl)butyl[hydroxy(phenyl)methyl]benzylphosphinic acid (6) (0.37 g, 0.6 mmol) in 25 mL of water containing 0.10 g of 10% Pd/C was hydrogenated at 40 psi for 6 hours. The mixture was filtered through a pad of Celite and lyophilized to give 2-([hydroxy(phenyl)methyl]hydroxyphosphinylmethyl)pentanedioic acid (9) (0.14 g, 70%) as a white solid.

¹H NMR (D₂O): 7.4 ppm (m, 5H), 5.0 ppm (d, 1H), 2.7 ppm (m, 1H), 2.4 ppm (m, 2H), 2.2 ppm (m, 1H), 1.9 ppm (m, 3H).

Elemental Analysis: Calculated $C_{13}H_{17}O_7P$, 0.6 $H_2O$: C, 47.74; H, 5.61. Found: C, 47.73; H, 5.68.

Example 12

Preparation of dibenzyl 2-methylenepentanedioate using Scheme VI

Benzyl acrylate (500 g, 3.0 mol) was heated in an oil bath to 100° C. Heating was stopped and HMPT (10 g, 61 mmol)

was added dropwise while maintaining an internal temperature below 140° C. Once addition was complete, the mixture was stirred and cooled to room temperature. A slurry of silica (5:1 Hexane/EtOAc) was added and the mixture was placed in a column containing a plug of dry silica. The column was washed with 1:1 Hexane/EtOAc and the fractions were combined and evaporated to give 450 g of clear light golden liquid. The liquid was distilled under high vacuum (200 μHg) at 180° C. to give 212 g (42%) of a clear and colorless liquid.

$^1$H NMR (CDCl$_3$): 7.3 ppm (m, 10H), 6.2 ppm (s, 1H), 5.6 ppm (s, 1H), 5.2 ppm (s, 2H), 5.1 ppm (s, 2H), 2.6 ppm (m, 4H).

Example 13

Preparation of dibenzyl 2-[[bis(benzyloxy)phosphoryl]methyl]pentanedioate using Scheme VI Dibenzyl phosphite (9.5 g, 36 mmol) in 350 mL of dichloromethane was cooled to 0° C. To this stirring solution was added trimethyl aluminum (18.2 mL, 2.0 M solution in hexane, 36.4 mmol). After 30 minutes, dibenzyl 2-methylenepentanedioate (2)(6.0 g, 37 mmol) in 90 mL of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100 mL of dichloromethane. The organics were combined, dried (MgSO$_4$), and evaporated to give a clear light golden liquid. The liquid was chromatographed on silica gel (4 cm×30 cm) and eluted with a gradient (4:1–1:1) solvent system (Hexane/EtOAc). The fractions containing the desired product were combined and evaporated to yield dibenzyl 2-[[bis(benzyloxy)phosphoryl]methyl]pentanedioate (7.1 g, 42%) as a clear and colorless liquid. The liquid was then distilled on a Kughleror apparatus at 0.5 mm Hg and 195–200° C. The distillate was discarded and the remaining light golden oil was chromatographed on silica gel (1:1, Hexane/EtOAc) to give 2.9 g of dibenzyl 2-[[bis(benzyloxy)phosphoryl]methyl]pentanedioate as a clear and colorless oil. TLC Rf 0.5 (1:1 Hexane/EtOAc).

$^1$H NMR (CDCl$_3$): 7.1–7.4 (m, 20H), 5.05 (s, 2H), 4.8–5.03 (m, 6H), 2.8 (1H), 2.22–2.40 (m, 3H), 1.80–2.02 (m, 3H).

Example 14

Preparation of 2-(phosphonomethyl)pentanedioic acid (Compound 3) using Scheme VI Benzyl pentanedioate 2(2.9 g, 4.9 mmol) was added to a mixture of 20 mL of methanol containing 0.29 g (6 mol %) of 10% Pd/C. This mixture was hydrogenated at 40 psi for 24 hours, filtered and evaporated to give 3(1.0 g, 90%) as a clear slightly golden viscous oil.

$^1$H NMR (D$_2$O): 2.6–2.78 (m, 1H), 2.25–2.40 (m, 2H), 1.75–2.15 (m, 4H).

Example 15

Preparation of 2-[(N-hydroxy)carbamoyl]methyl]pentanedioic acid using Scheme I

Preparation of 2,3,4-butanetricarboxylic acid

Nitric acid (160 mL, 70%) was added to a round bottom flask followed by copper (0.05 g, 0.31 mol) and ammonium metavandate (0.20 g, 0.002 mol). The mixture was heated to 55° C., at which time 1,2,3,6-tetrahydrobenzaldehyde (28 g, 0.25 mol) was added dropwise. Addition was at such a rate as to keep the temperature between 50–60° C. Once addition was completed, the mixture was heated for one hour at 55° C., cooled and let stand at 0° C. for 72 hours. At the end of this time, the mixture was filtered to yield 20 g of a light yellow solid. NMR (d6-DMSO): 2.6 (m, 1H), 2.5–2.3 (m, 4H), 2.2 (t, 2H).

Preparation of 3-(2,5-dioxotetrahydro-3-furanyl)propionic acid 1,2,4-Butanetricarboxylic acid (20 g, 0.105 mol) and nonane (200 mL) were added to a round bottom flask equipped with a soxhlet extractor. The solution was refluxed for 16 hours, at the end of which time the nonane was decanted from the flask. To the resulting liquid was added hot ethylene dichloride which was then treated with activated charcoal. The ethylene chloride was removed under reduced pressure, and the residue was then dissolved in acetic acid. Upon cooling, 9 g (50%) of the desired material was obtained. NMR (d6-DMSO): 3.2 (m, 1H), 3.0 (dd, 1H), 2.8 (dd, 1H), 2.3 (t, 2H), 2.0 (m, 1H), 1.8 (m, 1H). Anal. Calcd. for C$_7$H$_8$O$_5$—1.0 H$_2$O: C, 44.22; H, 5.25. Found: C, 44.47; H, 5.25.

Preparation of 2-[N-benzoyl)carbamoyl)methyl]pentanedioic acid 3-(2,5-dioxotetrahydro-3-furanyl)propionic acid (3.0 g, 17.4 mmol) was added to a round bottom flask containing CH$_2$Cl$_2$ (80 mL) and the resulting reaction mixture was cooled to −25° C. Triethylamine (6.0 mL, 43.1 mmol) was added followed by trimethylsilyl chloride (2.4 mol, 18.9 mmol). After 15 minutes, o-benzylhydroxylamine (2.1 g, 17.1 mmol) was added. The mixture was stirred at 0° C. for 1 hour and then quenched with 5% HCl. The aqueous phase was then extracted with ethyl acetate, and the organic extracts were combined and dried with MgSO$_4$. The solvent was removed under reduced pressure to yield a light yellow oil. The oil was then triturated with methylene chloride/hexane, which upon cooling afforded 0.29 g of the desired product as a white solid. NMR (D20): 7.5 (m, 5H), 5.1 (t, 2H), 2,6 (m, 3H), 2.2 (t, 2H), 1.7 (m, 2H). Anal. Calcd. for C$_{14}$H$_{17}$NO$_6$—0.15 H$_2$O: C, 56.43; H, 5,85; N, 4.70. Found: C, 56.31; H, 5.74; N, 5.05.

Preparation of 2-[(N-hydroxy)carbamoyl]methyl]pentanedioic acid

2-[(N-benzoyl)carbamoyl)methyl]pentanedioic acid (0.29 g, 1,0 mmol) in 20 mL water containing 0.10 g of 10% Pd/C was hydrogenated at 40 psi for 5 hours. The mixture was filtered through a pad of celite and the resulting solution was lyophilized to obtain the desired product.

Example 16

Preparation of 2-[(benzylsulfinyl)methyl]pentanedioic acid using Scheme XIII

Preparation of dibenzyl 2-[benzylsulfinyl)methyl]pentanedioate

To a solution of dibenzyl 2-methylenepentanedioate (12.16 g, 37.5 mmol) in acetone (100 mL), was added benzylmercaptan (9.31 g, 75.0 mmol) and 4-dimethylaminopyridine (0.46 g, 3.75 mmol) with stirring. The reaction mixture was refluxed for 16 hours. The cooled solution was concentrated under reduced pressure and purified by column chromatography to yield 15.2 g (90%) of clear oil.

$^1$H NMR (CDCl$_3$): δ2.0 (m, 2H), 2.3 (m, 2H), 2.5 (m, 1H), 2.6 (m, 2H), 3.6 (s, 2H), 4.9 (s, 2H), 5.0 (m, 2H), 7.2–7.5 (m, 15H).

Preparation of 2-[(benzylsulfinyl)methyl] pentanedioic acid

To a cooled solution (5° C.) of dibenzyl 2-[(benzylsulfinyl)methyl]pentanedioate (15.2 g, 33.9 mmol) in tetrahydrofuran (750 mL) was added 0.1 N NaOH (745 mL, 74.5 mmol NaOH) with stirring. The cloudy reaction mixture was allowed to warm to room temperature. After 16 hours, the reaction mixture had become homogenous. The solution was concentrated under reduced pressure to remove the tetrahydrofuran. The remaining aqueous solution was washed with ethyl acetate, then made acidic (pH 1) with concentrated HCl. The mixture was extracted twice with ethyl acetate. The ethyl acetate was removed under reduced pressure and the resulting waxy solid was purified by column chromatography to yield 6.9 g (76%) of white solid.

$^1$H NMR (d6-DMSO): δ1.7 (m, 2H), 2.2 (t, 2H), 2.3–2.6 (m, 3H), 3.8 (s, 2H), 7.3 (s, 5H).

Preparation of 2-[(benzylsulfinyl)methyl] pentanedioic acid

To a cooled mixture (−78° C.) of 2-[(benzylsulfinyl) methyl]pentanedioic acid (5.2 g, 19.4 mmol) in dichloromethane (100 mL) was added 3-chloroperbenzoic acid (85%, 3.9 g, 19.4 mmol) with stirring. The reaction mixture was allowed to stir for 1 hour at −78° C., then allowed to warm to room temperature. If starting material was still present according to analysis by TLC, the reaction was cooled again to −78° C. and additional 3-chloroperbenzoic acid (2–4 mmol depending on the intensity of the starting material spot) added and the reaction mixture allowed to warm at room temperature. This was repeated until no more starting material was detected by TLC. The dichloromethane was removed under reduced pressure and the resulting residue was purified by column chromatography to yield 3.8 g (69%) of white solid.

Example 17

Preparation of 2-[(benzylsulfinyl)methyl] pentanedioic acid using Scheme XIV

Preparation of dibenzyl 2-[(benzylsulfinyl)methyl] pentanedioate

To a solution of dibenzyl 2-methylenepentanedioate (12.16 g, 37.5 mmol) in acetone (100 mL), was added benzylmercaptan (9.31 g, 75.0 mmol) and 4-dimethylaminopyridine (0.46 g, 3.75 mmol) with stirring. The reaction mixture was refluxed for 16 hours. The cooled solution was concentrated under reduced pressure and purified by column chromatography to yield 15.2 g (90%) of clear oil.

$^1$H NMR (CDCl$_3$): δ2.0 (m, 2H), 2.3 (m, 2H), 2.5 (m, 1H), 2.6 (m 2H), 3.6 (s, 2H), 4.9 (s, 2H) 5.0 (m, 2H), 7.2–7.5 (m, 15H).

Preparation of dibenzyl 2-[(benzylsulfinyl)methyl] pentanedioate

To a cooled solution (−78° C.) of dibenzyl 2-[(benzylsulfonyl)methyl]pentanedioate (8.2 g, 18.3 mmol) in dichloromethane (100 mL), was added 3-chloroperbenzoic acid (85%, 8.2 g, 40.3 mmol) with stirring. The reaction mixture was allowed to warm to room temperature. White solids precipitated from the reaction mixture. After 2 hours at room temperature, the reaction mixture was filtered and the white solids washed with dichloromethane. The filtrate was washed twice with a saturated aqueous solution of sodium bicarbonate and the dichloromethane removed under reduced pressure. The resulting oil was purified by column chromatography to yield 7.5 g (85%) of clear oil.

$^1$H NMR (CDCl$_3$): δ2.0 (m, 2H), 2.3 (t, 2H), 3.1 (m, 1H), 2.9 & 3.4 (ddd, 2H), 4.2 (s, 2H), 5.1 (s, 2H), 5.2 (s, 2H), 7.2–7.4 (m, 15H).

Preparation of dibenzyl 2-[(benzylsulfonyl)methyl] pentanedioic acid

A mixture of dibenzyl 2-[(benzylsulfonyl)methyl]-pentanedioate (1.1 g, 2.3 mmol), palladium on carbon catalyst (10%, 0.6 g) and water (25 mL) was shaken under hydrogen (60 psi) for 16 hours. The reaction mixture was filtered over celite and the filtrate was lyophilized to yield 0.62 g (90%) of grayish-white crystals.

$^1$H NMR (d6-DMSO): δ1.8 (m, 2H), 2.2 (t, 2H), 2.8 (m, 1H), 3.1–3.5 (ddd, 2H), 4.5 (s, 2H), 7.4 (s, 5H). Anal. Calcd. for C$_{13}$H$_{16}$SO$_6$—0.65 H$_2$O: C, 50.04; H, 5.59; S, 10.28. Found: C, 49.99; H, 5.52; S, 10.07.

Example 18

Preparation of 2-[(benzylsulfoximinyl)methyl] pentanedioic acid using Scheme XV

Preparation of dibenzyl 2-[benzylsulfanyl) methyl] pentanedioate

To a solution of dibenzyl 2-methylenepentanedioate (12.16 g, 37.5 mmol) in acetone (100 mL), was added benzylmercaptan (9.31 g, 75.0 mmol) and 4-dimethylaminopyridine (0.46 g, 3.75 mmol) with stirring. The reaction mixture was refluxed for 16 hours. The cooled solution was concentrated under reduced pressure and purified by column chromatography to yield 15.2 g (90%) of clear oil.

$^1$H NMR (CDCl$_3$): δ2.0 (m, 2H), 2.3 (m, 2H), 2.5 (m, 1H), 2.6 (m, 2H), 3.6 (s, 2H), 4.9 (s, 2H), 5.0 (m, 2H), 7.2–7.5 (m, 15H).

Preparation of 2-[(benzylsulfanyl)methyl] pentanedioic acid

To a cooled solution (5° C.) of dibenzyl 2-[(benzylsulfanyl)methyl]pentanedioate (15.2 g, 33.9 mmol) in tetrahydrofuran (750 mL) was added 0.1 N NaOH (745 mL, 74.5 mmol NaOH) with stirring. The cloudy reaction mixture was allowed to warm to room temperature. After 16 hours, the reaction mixture had become homogenous. The solution was concentrated under reduced pressure to remove the tetrahydrofuran. The remaining aqueous solution was washed with ethyl acetate, then made acidic (pH 1) with concentrated HCl. The mixture was extracted twice with ethyl acetate. The ethyl acetate was removed under reduced pressure and the resulting waxy solid was purified by column chromatography to yield 6.9 g (76%) of white solid.

$^1$H NMR (d6-DMSO): δ1.7 (m, 2H), 2.2 (t, 2H), 2.3–2.6 (m, 3H), 3.8 (s, 2H), 7.3 (s, 5H).

Preparation of 2-[(benzylsulfinyl)methyl] pentanedioic acid

To a cooled mixture (−78° C.) of 2-[(benzylsulfanyl) methyl]pentanedioic acid (5.2 g, 19.4 mmol) in dichloromethane (100 mL) was added 3-chloroperbenzoic acid (85%, 3.9 g, 19.4 mmol) with stirring. The reaction mixture was allowed to stir for 1 hour at −78° C., then allowed to warm to room temperature. If starting material was still present according to analysis by TLC, the reaction was cooled again to −78° C. and additional 3-chloroperbenzoic acid (2–4 mmol depending on the intensity of the starting material spot) added and the reaction mixture allowed to warm at room temperature. This was repeated until no more starting material was detected by TLC. The dichloromethane was removed under reduced pressure and the resulting residue was purified by column chromatography to yield 3.8 g (69%) of white solid.

Preparation of 2-[(benzylsulfoximinyl)methyl] pentanedioic acid

To a mixture of 2-[benzylsulfinyl)methyl]pentane-dioic acid (2.0 g, 7.0 mmol) in chloroform (20 mL) was added sodium azide (0.5 g, 7.7 mmol) and concentrated sulfuric acid (0.7 g, 7.0 mmol) with stirring. After 16 hours, water was added to the reaction mixture and additional chloroform. The chloroform layer was removed and saved and the aqueous layer was washed again with chloroform. The combined chloroform extracts were concentrated under vacuum and the resulting residue was purified by column chromatography to yield 0.80 g (38%) of white solid.

Example 19

Synthesis of 2-[[[2-(carboxy)propyl]hydroxyphosphinyl]methyl]pentanedioic acid

Di-tert-butyl 2-methylenepentanedioate

Tert-butyl acrylate (465 g, 3.628 mol) was warmed to 100° C. under nitrogen, then hexamethylphosphorous triamide (10 g, 61.2 mmol) was added dropwise and the addition rate was adjusted to maintain the reaction temperature at 100° C. The reaction mixture was allowed to cool, then poured over a plug of silica (~1000 mL) and washed completely off the silica with 4:1 hexane/ethyl acetate. The solvent was removed under reduced pressure and the resulting oil was distilled. Some material was collected from room temperature to 50° C. under high vacuum, and discarded. The temperature was then raised to ~80° C. and the product (300 g, 65%, b.p. 67–70° C. at 300$\mu$) was collected as a clear oil.

$^1$H NMR (CDCl$_3$): δ1.4 (m, 18H), 2.4 (t, 2H), 2.6 (t, 2H), 5.5 (s, 1H), 6.0 (s, 1H).

Di-tert-butyl 2-[(hydroxyphosphinyl)methyl]pentanedioate

A mixture of ammonium phosphinate (162.6 g, 1.96 mol) and 1,1,1,3,3,3-hexamethyldisilazane (316 g, 1.96 mol) was heated to 105° C. for 2 hours. The reaction mixture was cooled in an ice bath and di-tert-butyl 2-methylenepentane-1,5-dioate (251 g, 0.979 mol) dissolved in dichloromethane (1000 mL) was added dropwise. The reaction mixture was allowed to warm to room temperature overnight. The reaction mixture was then quenched with distilled water (500 mL) and the organic layer was retained. The aqueous layer was washed a second time with dichloromethane and the combined organic layers were dried over magnesium sulfate. Then the solvent was removed under reduced pressure leaving a slightly yellow oil (315 g, 100%). This product was found to be of sufficient purity for use in the next reaction.

$^1$H NMR (CDCl$_3$): δ1.4 (m, 18H), 1.9 (m, 3H), 2.1 (m, 1H), 2.3 (m, 2H), 2.7 (m, 1H), 6.5 & 7.9 (d, 1H, the P—H), 11.0 (s, 1H).

Di-tert-butyl 2-[(tert-butoxyphosphinyl)methyl]pentanedioate

To a solution of di-tert-butyl 2-[(hydroxyphosphinyl) methyl]pentane-1,5-dioate (315 g, 0.977 mol) in dichloromethane (1000 mL) cooled in an ice bath and under nitrogen were added tert-butanol (123.1 g, 1.66 mol), 4-dimethylaminopyridine (1 g, 8.2 mmol), and 1-ethyl-3-(3-dimethylaminopropyl)carbodiimide (281 g, 1.47 mol). The reaction was allowed to stir overnight. Water was added to the reaction mixture and the dichloromethane layer was retained and dried, and the solvent was removed under reduced pressure. The resulting residue was purified by column chromatography and the desired product was eluted with 1:1 to 2:3 hexane/ethyl acetate. The fractions containing product were concentrated under reduced pressure leaving a clear oil (260 g, 70%).

$^1$H NMR (CDCl$_3$): δ1.4 (m, 27H), 1.8 (m, 1H), 1.9 (m, 2H), 2.1 (m, 1H), 2.3 (m, 2H), 2.7–2.8 (m, 1H), 6.7 & 8.0 (d, 1H, the P—H).

Di-tert-butyl 2-[[[2-(benzylcarboxy)propyl]tert-butoxyphosphinyl]methyl]pentanedioate To a solution of di-tert-butyl 2-[(tert-butoxyphosphinyl) methyl]pentane-1,5-dioate (13.62 g, 36.0 mmol) and benzyl methacrylate (6.35 g, 36.0 mmol) in THF (100 mL) under nitrogen was added sodium hydride (0.14 g, 60% dispersion in oil, 3.60 mmol). After three hours, the reaction mixture was poured into water (300 mL) and ether (100 mL) was added. The organic layer was separated and retained, and the aqueous layer was washed again with ether (100 mL). The combined organic extracts were dried over magnesium sulfate and the solvent was removed under reduced pressure. The resulting residue was purified by column chromatography and the product was eluted with 2:3 EtOAc/Hexane. The solvent was removed under reduced pressure leaving a clear oil (10.5 g, 53%).

$^1$H NMR (CDCl$_3$): δ1.3 (m, 3H), 1.5 (m, 27H), 1.7 (m, 2H), 1.9 (m, 2H), 2.2 (m, 4H), 2.6 (m, 1H), 2.9 (m, 1H), 5.1 (m, 2H), 7.3 (m, 5H).

2-[[[2-(Benzylcarboxy)propyl]hydroxyphosphinyl)methyl]pentanedioic acid

To a solution of di-tert-butyl 2-[[[2-(benzylcarboxy) propyl]tert-butoxyphosphinyl]methyl]pentane-1,5-dioate (1.6 g, 2.89 mmol) in dichloromethane (10 mL) under nitrogen was added trifluoroacetic acid (10 mL). The reaction mixture was stirred for two hours and then concentrated under reduced pressure. Additional dichloromethane was added to the reaction residue and removed under reduced pressure. The product was dissolved in ethyl acetate and washed with water, then the organic layer was dried over magnesium sulfate and the solvent was removed under reduced pressure leaving a clear oil (800 mg, 72%)

$^1$H NMR (D$_2$O): δ1.2 (m, 3H), 1.6–1.8 (m, 4H), 2.1 (m, 2H), 2.2 (m, 2H), 2.6 (m, 1H), 2.8 (m, 1H), 5.0 (m, 2H), 7.3 (m, 5H). Analysis calculated for C$_{17}$H$_{23}$PO$_8$1.0 H$_2$O: C, 50.50; H, 6.23. Found: C, 50.52; H, 5.92.

Di-tert-butyl 2-[[[2-(carboxy)propyl]tert-butoxy-phosphinyl]methyl]pentanedioate A solution of di-tert-butyl 2-[[[2-(benzylcarboxy)propyl]tert-butoxyphosphinyl]methyl]pentane 1,5-dioate (8.9 g, 16.1 mmol), palladium on carbon catalyst (10%, 1.0 g) and ethyl acetate (100 mL) was shaken under hydrogen (60 psi) for 16 hours. The reaction mixture was filtered over celite and the filtrate was concentrated under reduced pressure leaving a clear oil (7.5 g, 100%).

$^1$H NMR (CDCl$_3$): δ1.3 (d, 3H), 1.4–1.5 (m, 27H), 1.8 (m, 2H), 1.9 (m, 2H), 2.2 (m, 4H), 2.7 (m, 1H), 2.9 (m, 1H).

2-[[[2-(Carboxy)propyl]hydroxyphosphinyl]methyl]pentanedioic acid

To a solution of di-tert-butyl 2-[[[2-(carboxy)propyl]tert-butoxyphosphinyl]methyl]pentane-1,5-dioate (2.1 g, 4.53 mmol) in dichloromethane (10 mL) under nitrogen was added trifluoroacetic acid (10 mL). The reaction mixture was stirred for two hours and then concentrated under reduced pressure. Additional dichloromethane was added to the reaction residue and removed under reduced pressure. The resulting residue was triturated with acetonitrile, then dried under reduced pressure leaving a thick clear oil (1.2 g, 89%).

$^1$H NMR (D$_2$O): δ1.2 (d, 3H), 1.9 (m, 4H), 2.2 (m, 2H), 2.4 (m, 2H), 2.8 (m, 2H). Analysis calculated for C$_{10}$H$_{17}$PO$_8$0.2 CH$_3$CN: C, 41.03; H, 5.83. Found: C, 41.05; H, 5.92.

Example 20

Synthesis of 2-[({[Benzylamino]methyl}(hydroxyphosphinyl))methyl]pentanedioic acid (3)

Di-tert-butyl 2-[((tert-butoxy){[benzylamino]methyl}phosphoryl)methyl]pentane-1,5-dioate (3a)

A solution of 1,3,5-tribenzylhexahydro-1,3,5-triazine (14.30 g, 40.0 mmol) and di-tert-butyl 2-{[(tert-butoxy)phosphoryl]methyl}pentane-1,5-dioate (37.85 g, 100 mmol) in toluene (200 mL) was stirred at 110° C. for 14 hours. The solvent was removed under reduced pressure and the residual yellow oil was purified by silica gel chromatography (hexanes/ethyl acetate, 2/1) to give 23.40 g of light yellow oil (43% yield).

$^1$H NMR (CDCl$_3$) δ1.40–1.48 (m, 27H), 1.7–2.1 (m, 4H), 2.2–2.4 (m, 3H), 2.6–3.0 (m, 3H), 3.8–4.0 (m, 2H), 7.2–7.4 (m, 5H).

2-[({[Benzylamino]methyl}(hydroxyphosphinyl))methyl]pentanedioic acid (3)

To a solution of di-tert-butyl 2-[((tert-butoxy){[benzylamino]methyl}phosphoryl)methyl]pentane-1,5-dioate (0.498 g, 1.0 mmol) in dichloromethane (10 mL) was added trifluoroacetic acid (5 mL) at 0° C., and the mixture was stirred at room temperature for eighteen hours. The solvent was removed under reduced pressure. The residual oil was taken up with dichloromethane (10 mL) and concentrated. This process was repeated three times to remove trifluoroacetic acid completely. The resulting oil was crystallized from methanol to give 0.174 g of white solid (53% yield).

$^1$H NMR (D$_2$O) δ1.40–1.48 (m, 27H), 1.7–2.1 (m, 4H), 2.2–2.4 (m, 3H), 2.6–3.0 (m, 3H), 3.8–4.0 (m, 2H), 7.2–7.4 (m, 5H).

Example 21

Synthesis of 2-[({[Phenylamino]methyl}(hydroxyphosphinyl))methyl]pentanedioic acid (7)

Using a method similar to that described above in Example 20, 2-[({[phenylamino]methyl}(hydroxyphosphinyl))methyl]pentanedioic acid was synthesized.

$^1$H NMR (D$_2$O) δ1.4–1.6 (m, 1H), 1.7–1.9 (m, 3H), 2.2–2.4 (m, 2H), 2.2–2.4 (m, 2H), 2.5–2.7 (m, 1H), 3.53 (d, J=8.8 Hz, 2H), 7.3–7.5 (m, 5H).

Example 22

Synthesis of 2-[({[4-Fluorophenylamino]methyl}(hydroxyphosphinyl))methyl]pentanedioic acid (10)

Using a method similar to that described above in Example 20, 2-[({[4-fluorophenylamine]methyl}(hydroxyphosphinyl))methyl]pentanedioic acid was synthesized.

$^1$H NMR (D$_2$O) δ1.5–1.7 (m, 1H), 1.8–2.0 (m, 3H), 2.3–2.5 (m, 2H), 2.6–2.7 (m, 1H), 3.84 (d, J=9.0 Hz, 2H), 7.2–7.5 (4H).

Example 23

Synthesis of 2-[({[4-Methoxyphenylamino]methyl}(hydroxyphosphinyl))methyl]pentanedioic acid (11)

Using a method similar to that described above in Example 20, 2-[({[4-Methoxyphenylamino]methyl}(hydroxy-phosphinyl))methyl]pentanedioic acid was synthesized.

$^1$H NMR (D$_2$O) δ1.2–1.3 (m, 1H), 1.6–1.7 (m, 3H), 2.22–2.23 (m, 2H), 2.3–2.5 (m, 1H), 3.4 (d, J=8.9 Hz, 2H), 3.7 (s, 3H), 7.0 (d, J=12 Hz, 2H), 7.4 (d, J=12 Hz, 2H).

Example 24

Synthesis of 2-({[(phenylcarbonylamino)methyl](hydroxyphosphinyl)}methyl)pentanedioic acid (8)

Di-tert-butyl 2-{[(aminomethyl)(tert-butoxy)phosphoryl]-methyl}pentane-1,5-dioate (8a)

To a solution of di-tert-butyl 2-[((tert-butoxy)-{[benzylamino]methyl}phosphoryl)methyl]pentane-1,5-dioate (8.20 g, 16.5 mmol) in ethanol (100 mL) was added palladium on carbon (0.50 g), and the suspension was shaken under hydrogen (50 psi) for 4 days. The catalyst was removed by filtration through a pad of Celite. The filtrate was concentrated to give 6.629 g of colorless oil (99% yield).

$^1$H NMR (CD$_3$OD) δ1.40–1.60 (m, 27H), 1.80–2.00 (m, 3H), 2.2–2.4 (m, 3H), 2.7–3.0 (m, 3H).

Di-tert-butyl 2-({(tert-butoxy)[(phenylcarbonylamino)methyl]phosphoryl}methyl)pentane-1,5-dioate (8b)

To a solution of di-tert-butyl 2-{[(aminomethyl)-(tert-butoxy)phosphoryl]methyl}pentane-1,5-dioate (1.222 g, 3.0 mmol) and benzoyl chloride (0.46 mL, 4.0 mmol) in dichloromethane (10 mL) was added triethylamine (0.56 mL, 4.0 mmol) at 0° C., and the mixture was stirred at room temperature for 16 hours. The reaction mixture was diluted with dichloromethane (15 mL), washed with 1 N HCl (25 mL), dried over Na$_2$SO$_4$, and concentrated. The crude material was purified by silica gel chromatography (ethyl acetate/hexanes=2/1) to give 1.259 g of colorless oil (74% yield).

$^1$H NMR (CDCl$_3$) δ1.30–1.60 (m, 27H), 1.60–2.00 (m, 3H), 2.20–2.40 (m, 3H), 2.70–2.90 (m, 3H), 3.5–4.2 (m, 2H), 7.0–7.3 (m, 1H), 7.4–7.6 (m, 3H), 7.8–7.9 (m, 1H).

2-({[(Phenylcarbonylamino)methyl](hydroxyphosphinyl)}methyl)pentanedioic acid (8)

To a solution of di-tert-butyl 2-({(tert-butoxy)-[(phenylcarbonylamino)methyl]phosphoryl}methyl)

pentane-1,5-dioate (1.230 g, 2.4 mmol) in dichloromethane (10 ML) was added trifluoroacetic acid (5 mL) at room temperature, and the mixture was stirred at room temperature for 18 hours. The solvent was removed under reduced pressure. The residual oil was taken up with dichloromethane (10 mL) and concentrated. This process was repeated three times to remove trifluoroacetic acid completely. The resulting oil was crystallized from acetonitrile-water to give 0.620 g of white solid (75% yield).

$^1$H NMR (D$_2$O) δ1.9–2.1 (m, 3H), 2.2–2.4 (m, 1H), 2.4–2.6 (m, 2H), 2.8–3.0 (m, 1H), 3.7–3.9 (m, 2H), 7.5–7.9 (m, 5H).

Example 25

Synthesis of 2-({[(phenylsulfonylamino)methyl] (hydroxyphosphinyl)}methyl)pentanedioic acid (9)

Using a method similar to that described above in Example 24, 2-({[(phenylsulfonylamino)methyl](hydroxyphosphinyl)}methyl)pentanedioic acid was synthesized.

$^1$H NMR (D$_2$O) δ1.6–2.1 (m, 4H), 2.3–2.4 (m, 2H), 2.5–2.7 (m, 1H), 2.9–3.1 (m, 2H), 7.7–8.0 (m, 5H).

Example 26

Synthesis of 2-(2-sulfanylethyl)pentanedioic acid

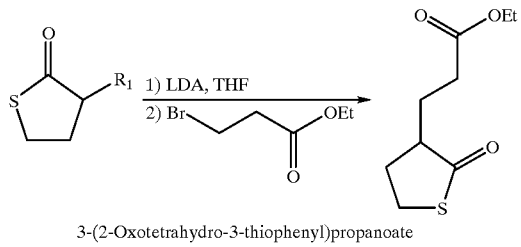

3-(2-Oxotetrahydro-3-thiophenyl)propanoate

To a cooled solution (−78° C.) of lithium diisopropylamide (LDA) (98 mmol) in THF (100 ml) was added dropwise γ-thiobutyrolactone (10 g, 98 mmol). After stirring for fifteen minutes, ethyl 3-bromopropanoate (35.4 g, 196 mmol) was added and the reaction allowed to warm to room temperature overnight. The solvent was removed under reduced pressure and the resulting residue was purified by column chromatography yielding 3 g (16%) of clear oil. $^1$H NMR (CDCl$_3$) δ1.2 (t, 3H), 1.7 (m, 1H), 1.9 (m, 1H), 2.1 (m, 1H), 2.4 (t, 2H), 2.5 (m, 2H), 3.3 (t, 2H), 4.2 (q, 2H).

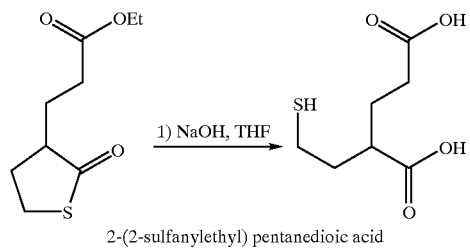

2-(2-sulfanylethyl) pentanedioic acid

To a solution of ethyl 3-(2-oxotetrahydro-3-thiophenyl) propanoate (0.77 g, 3.81 mmol) in THF (5 ml) was added sodium hydroxide (1 M in water, 5 ml). The mixture was allowed to stir for two days, then the THF was removed under reduced pressure, the aqueous layer was washed with ether, then acidified to pH 1 with HCl and extracted with ethyl acetate. The combined ethyl acetate extracts were dried over magnesium sulfate and the solvent was removed under reduced pressure. The resulting residue was purified by column chromatography yielding a 150 mg of clear oil (20%). $^1$H NMR (d6-DMSO) δ1.7 (m, 3H), 1.8 (m, 1H), 2.2 (m, 2H), 2.3–2.5 (m, 4H). Analysis calculated for C$_7$H$_{12}$SO$_4$: C, 43.74; H, 6.29; S, 16.68. Found: C, 43.61; H, 6.39; S, 16.55.

Example 27

A patient is at risk of injury from a cancerous tumor growth, invasion, or metastasis. The patient may be pretreated with an effective amount of a NAALADase inhibitor or a pharmaceutical composition of the present invention. It is expected that after the pretreatment, the patient would be protected from any injury due to a cancerous tumor growth, invasion, or metastasis.

Example 28

A patient is suffering from a cancerous tumor growth, invasion, or metastasis. The patient may be administered during or after the inception of the tumor, an effective amount of a NAALADase inhibitor or a pharmaceutical composition of the present invention. It is expected that after the treatment, the patient would recover or would not suffer any significant injury due to the cancerous tumor growth, invasion, or metastasis.

Example 29

A patient is suffering from a neovascular disease of the eye. A patient may be administered an effective amount of a NAALADase inhibitor or a pharmaceutical composition of the present invention. It is expected that after the treatment, the patient would recover or would not suffer any significant injury due to the neovascular disease of the eye.

Example 30

A patient is suffering from rheumatoid arthritis. A patient may be administered an effective amount of a NAALADase inhibitor or a pharmaceutical composition of the present invention. It is expected that after the treatment, the patient would recover or would not suffer any significant injury due to the rheumatoid arthritis.

Example 31

A patient is suffering from peripheral vascular disorder. A patient may be administered an effective amount of a NAALADase inhibitor or a pharmaceutical composition of the present invention. It is expected that after the treatment, the patient would recover or would not suffer any significant injury due to the peripheral vascular disorder.

Example 32

A patient is suffering from metastatic adenocarcinoma of cancer, as defined herein. Although the adenocarcinoma appears to have metastasized, the patient nevertheless undergoes surgery to remove the adenocarcinoma. The patient may then be locally administered an effective amount of a compound or a pharmaceutical composition of the present invention approximately from the time of initial diagnosis through post-surgical recovery. After post-surgical recovery, the patient may continue the same treatment by a regimen of periodic local administration, and carefully monitored for adverse side-effects. It is expected that after the treatments, the patient would be protected from recurrences of the adenocarcinoma, and any residual tumorous cells would be inhibited (i.e., arrested in development) or relieved (i.e., caused to regress).

Example 33

A patient is suffering from cancer, as defined herein. An effective amount of a compound or a pharmaceutical composition of the present invention may be administered directly to the cancer cells. After this initial treatment, the patient may be optionally administered an effective amount of the same or a different compound of the present invention by direct injection, subdural pump or implantation of a biocompatible polymeric matrix delivery system. It is expected that after the treatment(s), the patient would be protected from recurrences of the cancer, and the cancer would be inhibited (i.e., arrested in development) or relieved (i.e., caused to regress).

Example 34

A female patient wishes to become temporarily infertile, so as not to become pregnant during sexual intercourse. An effective amount of a compound or a pharmaceutical composition of the present invention may then be administered, using gels, foams, creams, suppositories, or carbopol polymers, to the patient. It is expected that after the treatment, angiogenesis necessary for fertility would be inhibited and the patient would be protected from pregnancy for the length of time that continued treatments were periodically administered.

Example 35

A female patient wishes to become temporarily infertile, so as not to become pregnant during sexual intercourse. An effective amount of a compound or a pharmaceutical composition of the present invention may then be administered, using carbopol polymers prepared from acrylic acid, to the patient. It is expected that after the treatment, angiogenesis necessary for fertility would be inhibited and the patient would be protected from pregnancy for the length of time that continued treatments were periodically administered.

Example 36

A patient is suffering from a dermatologic ulcer. A patient may be administered an effective amount of a NAALADase inhibitor or a pharmaceutical composition of the present invention. It is expected that after the treatment, the patient would recover or would not suffer any significant injury due to the dermatologic ulcer.

Example 37

A patient is suffering from a soft tissue wound. A patient may be administered an effective amount of a NAALADase inhibitor or a pharmaceutical composition of the present invention. It is expected that after the treatment, the patient would recover or would not suffer any significant injury due to the soft tissue wound.

Example 38

A patient is suffering from a cardiovascular disease. A patient may be administered an effective amount of a NAALADase inhibitor or a pharmaceutical composition of the present invention. It is expected that after the treatment, the patient would recover or would not suffer any significant injury due to the cardiovascular disease.

Example 39

A patient is diagnosed with an angiogenesis-dependent disease, disorder, or condition, such as, but not limited to, those identified in these examples. An effective amount of a compound or a pharmaceutical composition of the present invention may then be administered to the patient intraveneously, intramuscularly, intraventricularly to the brain, rectally, subcutaneously, intranasally, through a catheter with or without a pump, orally, through a transdermal patch, topically, or through a polymer implant. After the treatment, the patient's condition would be expected to improve.

Example 40

A patient is diagnosed with an angiogenesis-dependent disease, disorder, or condition, such as, but not limited to, those identified in these examples. A compound or a pharmaceutical composition of the present invention may then be administered to the patient in the form of a 100 mg/kg bolus, optionally followed by a 20 mg/kg per hour intravenous infusion over a two-hour period. After the treatment, the patient's condition would be expected to improve.

The invention being thus described, it will be obvious that the same may be varied in many ways. Such variations are not to be regarded as a departure from the spirit and scope of the invention and all such modifications are intended to be included within the scope of the following claims.

We claim:

1. A method of inhibiting angiogenesis in non-cancerous tissue comprising administering an anti-angiogenic amount of a NAALADase inhibitor to a patient in need of angiogenesis inhibition suffering from a disease, disorder, or condition other than cancer, wherein said tissue is other than prostate tissue.

2. The method of claim 1, wherein the NAALADase inhibitor is administered in combination with at least one additional therapeutic agent.

3. The method of claim 1, wherein the angiogenesis is related to a disease or disorder.

4. The method of claim 3, wherein the disease or disorder is a neovascular disease of the eye.

5. The method of claim 3, wherein the disease or disorder is rheumatoid arthritis.

6. The method of claim 3, wherein the disease or disorder is peripheral vascular disorder.

7. The method of claim 1, wherein the angiogenesis is necessary for fertility.

8. The method of claim 3, wherein the disease or disorder is a dermatologic ulcer.

9. The method of claim 3, wherein the disease or disorder is soft tissue wound healing.

10. The method of claim 3, wherein the disease or disorder is cardiovascular disease.

11. The method of claim 1, wherein the NAALADase inhibitor is a compound of Formula I:

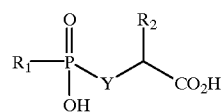

I or a pharmaceutically acceptable salt or hydrate thereof, wherein:

Y is $CR_3R_4$, $NR_5$ or O;

$R_1$ and $R_5$ are independently selected from the group consisting of hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, heteroaryl, or carbocycle, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar, or a mixture thereof;

$R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, Ar, or a mixture thereof, and $R_3$ and $R_4$ are independently selected from the group consisting of hydrogen, $C_1$–$C_6$ straight or branched chain alkyl, $C_2$–$C_6$ straight or branched chain alkenyl, $C_3$–$C_8$ cycloalkyl, $C_5$–$C_7$ cycloalkenyl, Ar, or halo;

wherein Ar represents a carbocyclic or heterocyclic moiety selected from the group consisting of phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, and adamantyl, unsubstituted or substituted with C1–C9 straight or branched chain alkyl, C2–C9 straight or branched chain alkenyl, C1–C9 alkoxy, C2–C9 alkenyloxy, phenoxy, benzyloxy, C3–C8 cycloalkyl, C5–C7 cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, or a mixture thereof.

12. The method of claim 11, wherein:
Y is $CH_2$;
$R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl, or mixtures thereof; and $R_2$ is $C_1$–$C_2$ alkyl substituted with carboxy.

13. The method of claim 12, wherein the compound is selected from the group consisting of:
2-[[(2-carboxyethyl)hydroxyphosphinyl]methyl]-pentanedioic acid;
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[(cyclohexyl)methylhydroxyphosphinyl]methyl]-pentanedioic acid;
2-[[phenylhydroxyphosphinyl]methyl]pentanedioic acid;
2-[(benzylhydroxyphosphinyl)methyl]pentanedioic acid;
2-[[(phenylmethyl)hydroxyphosphinyl]methyl]-pentanedioic acid;
2-[[(phenylethyl)hydroxyphosphinyl]methyl]-pentanedioic acid;
2-[[(phenylpropyl)hydroxyphosphinyl]methyl]-pentanedioic acid;
2-[[(phenylbutyl)hydroxyphosphinyl]methyl]-pentanedioic acid;
2-[[(4-methylbenzyl)hydroxyphosphinyl]methyl]-pentanedioic acid;
2-[[(4-fluorobenzyl)hydroxyphosphinyl]methyl]-pentanedioic acid;
2-[[(2-fluorobenzyl)hydroxyphosphinyl]methyl]-pentanedioic acid;
2-[[(pentafluorobenzyl)hydroxyphosphinyl]methyl]-pentanedioic acid;
2-[[(methoxybenzyl)hydroxyphosphinyl]methyl]-pentanedioic acid;
2[[(2,3,4-trimethoxyphenyl)hydroxyphosphinyl]methyl] pentanedioic acid;
2-[[(phenylprop-2-enyl)hydroxyphosphinyl]methyl]-pentanedioic acid;
2-[[(2-fluorobenzyl)hydroxyphosphinyl]methyl]-pentanedioic acid;
2-[[((hydroxy)phenylmethyl)hydroxyphosphinyl]-methyl] pentanedioic acid;
2-[[(3-methylbenzyl)hydroxyphosphinyl]methyl]-pentanedioic acid;
2-[[(4-fluorophenyl)hydroxyphosphinyl]methyl]-pentanedioic acid;
2-[[(3-trifluoromethylbenzyl)hydroxyphosphinyl]-methyl] pentanedioic acid; and
pharmaceutically acceptable salts and hydrates thereof.

14. The method of claim 11, wherein:
$R_1$ is 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl or $C_1$–$C_4$ straight or branched chain alkyl substituted with 2-indolyl, 3-indolyl, 4-indolyl, 2-furyl, 3-furyl, tetrahydrofuranyl, 2-thienyl, 3-thienyl, 2-pyridyl, 3-pyridyl or 4-pyridyl; or $R_1$ is 1-naphthyl, 2-naphthyl, or $C_1$–$C_4$ straight or branched chain alkyl substituted with 1-naphthyl or 2-naphthyl; and
$R_2$ is $C_3$–$C_9$ alkyl.

15. The method of claim 14, wherein the compound is selected from the group consisting of:
2-[(methylhydroxyphosphinyl)methyl]hexanedioic acid;
2-[(benzylhydroxyphosphinyl)methyl]hexanedioic acid;
2-[(methylhydroxyphosphinyl)methyl]heptanedioic acid;
2-[(benzylhydroxyphosphinyl)methyl]heptanedioic acid;
2-[(methylhydroxyphosphinyl)methyl]octanedioic acid;
2-[(benzylhydroxyphosphinyl)methyl]octanedioic acid;

2-[(methylhydroxyphosphinyl)methyl]nonanedioic acid;
2-[(benzylhydroxyphosphinyl)methyl]nonanedioic acid;
2-[(methylhydroxyphosphinyl)methyl]decanedioic acid;
2-[(benzylhydroxyphosphinyl)methyl]decanedioic acid;
2-[[(2-pyridyl)methylhydroxyphosphinyl]methyl]-pentanedioic acid;
2-[[(3-pyridyl)methylhydroxyphosphinyl]methyl]-pentanedioic acid;
2-[[(4-pyridyl)methylhydroxyphosphinyl]methyl]-pentanedioic acid;
2-[[(3-pyridyl)ethylhydroxyphosphinyl]methyl]-pentanedioic acid;
2-[[(3-pyridyl)propylhydroxyphosphinyl]methyl]-pentanedioic acid;
2-[[(tetrahydrofuranyl)methylhydroxyphosphinyl]-methyl]pentanedioic acid;
2-[[(tetrahydrofuranyl)ethylhydroxyphosphinyl]-methyl]pentanedioic acid;
2-[[(tetrahydrofuranyl)propylhydroxyphosphinyl]-methyl]pentanedioic acid;
2-[[(2-tetrahydropyranyl)hydroxyphosphinyl]methyl]-pentanedioic acid;
2-[[(3-tetrahydropyranyl)hydroxyphosphinyl]methyl]-pentanedioic acid;
2-[[(4-tetrahydropyranyl)hydroxyphosphinyl]methyl]-pentanedioic acid;
2-[[(2-indolyl)methylhydroxyphosphinyl]methyl]-pentanedioic acid;
2-[[(3-indolyl)methylhydroxyphosphinyl]methyl]-pentanedioic acid;
2-[[(4-indolyl)methylhydroxyphosphinyl]methyl]-pentanedioic acid;
2-[[(3-indolyl)ethylhydroxyphosphinyl]methyl]-pentanedioic acid;
2-[[(3-indolyl)propylhydroxyphosphinyl]methyl]-pentanedioic acid;
2-[[(2-thienyl)methylhydroxyphosphinyl]methyl]-pentanedioic acid;
2-[[(3-thienyl)methylhydroxyphosphinyl]methyl]-pentanedioic acid;
2-[[(4-thienyl)methylhydroxyphosphinyl]methyl]-pentanedioic acid;
2-[[(3-thienyl)ethylhydroxyphosphinyl]methyl]-pentanedioic acid;
2-[[(3-thienyl)propylhydroxyphosphinyl]methyl]-pentanedioic acid;
2-[[(2-pyridyl)hydroxyphosphinyl]methyl]pentanedioic acid;
2-[[(3-pyridyl)hydroxyphosphinyl]methyl]pentanedioic acid;
2-[[(4-pyridyl)hydroxyphosphinyl]methyl]pentanedioic acid;
2-[[(tetrahydrofuranyl)hydroxyphosphinyl]methyl]-pentanedioic acid;
2-[[(2-indolyl)hydroxyphosphinyl]methyl]pentanedioic acid;
2-[[(3-indolyl)hydroxyphosphinyl]methyl]pentanedioic acid;
2-[[(4-indolyl)hydroxyphosphinyl]methyl]pentanedioic acid;
2-[[(2-thienyl)hydroxyphosphinyl]methyl]pentanedioic acid;
2-[[(3-thienyl)hydroxyphosphinyl]methyl]pentanedioic acid;
2-[[(4-thienyl)hydroxyphosphinyl]methyl]pentanedioic acid;
2-[[(1-naphthyl)hydroxyphosphinyl]methyl]pentanedioic acid;
2-[[(2-naphthyl)hydroxyphosphinyl]methyl]-pentanedioic acid;
2-[[(1-naphthyl)methylhydroxyphosphinyl]methyl]-pentanedioic acid;
2-[[(2-naphthyl)methylhydroxyphosphinyl]methyl]-pentanedioic acid;
2-[[(1-naphthyl)ethylhydroxyphosphinyl]methyl]-pentanedioic acid;
2-[[(2-naphthyl)ethylhydroxyphosphinyl]methyl]-pentanedioic acid;
2-[[(1-naphthyl)propylhydroxyphosphinyl]methyl]-pentanedioic acid;
2-[[(2-naphthyl)propylhydroxyphosphinyl]methyl]-pentanedioic acid;
2-[[(1-naphthyl)butylhydroxyphosphinyl]methyl]-pentanedioic acid;
2-[[(2-naphthyl)butylhydroxyphosphinyl]methyl]-pentanedioic acid; and
pharmaceutically acceptable salts and hydrates thereof.

16. The method of claim 11, wherein:

Y is $CH_2$;

$R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl, or mixtures thereof; and $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl, or mixtures thereof.

17. The method of claim 16, wherein the compound is selected from the group consisting of:

3-(methylhydroxyphosphinyl)-2-phenylpropanoic acid;
3-(ethylhydroxyphosphinyl)-2-phenylpropanoic acid;
3-(propylhydroxyphosphinyl)-2-phenylpropanoic acid;
3-(butylhydroxyphosphinyl)-2-phenylpropanoic acid;
3-(cyclohexylhydroxyphosphinyl)-2-phenylpropanoic acid;
3-((cyclohexyl)methylhydroxyphosphinyl)-2-phenylpropanoic acid;
3-(phenylhydroxyphosphinyl)-2-phenylpropanoic acid;
3-(benzylhydroxyphosphinyl)-2-phenylpropanoic acid;
3-(phenylethylhydroxyphosphinyl)-2-phenylpropanoic acid;
3-(phenylpropylhydroxyphosphinyl)-2-phenylpropanoic acid;
3-(phenylbutylhydroxyphosphinyl)-2-phenylpropanoic acid;
3-((2,3,4-trimethoxyphenyl)-3-hydroxyphosphinyl)-2-phenylpropanoic acid;
3-(phenylprop-2-enylhydroxyphosphinyl)-2-phenylpropanoic acid;
3-(benzylhydroxyphosphinyl)-2-ethylpropanoic acid;
3-(benzylhydroxyphosphinyl)-2-propylpropanoic acid;
3-(benzylhydroxyphosphinyl)-2-butylpropanoic acid;
3-(benzylhydroxyphosphinyl)-2-cyclohexylpropanoic acid;
3-(benzylhydroxyphosphinyl)-2-(cyclohexyl)methylpropanoic acid;
3-(benzylhydroxyphosphinyl)-2-phenylpropanoic acid;

3-(benzylhydroxyphosphinyl)-2-benzylpropanoic acid;
3-(benzylhydroxyphosphinyl)-2-phenylethylpropanoic acid;
3-(benzylhydroxyphosphinyl)-2-phenylpropylpropanoic acid;
3-(benzylhydroxyphosphinyl)-2-phenylbutylpropanoic acid;
3-(benzylhydroxyphosphinyl)-2-(2,3,4-trimethoxyphenyl)-propanoic acid;
3-(benzylhydroxyphosphinyl)-2-phenylprop-2-enylpropanoic acid; and
pharmaceutically acceptable salts and hydrates thereof.

18. The method of claim 11, wherein:
at least one of $R_1$ and $R_2$ is 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, or $C_1-C_4$ straight or branched chain alkyl substituted with 2-indolyl 3-indolyl, 4-indolyl, 2-furyl, 3-furyl, tetrahydrofuranyl, 2-thienyl, 3-thienyl, 2-pyridyl, 3-pyridyl or 4-pyridyl; or
$R_1$ is 1-naphthyl, 2-naphthyl, or $C_1-C_4$ straight or branched chain alkyl substituted with 1-naphthyl or 2-naphthyl.

19. The method of claim 18, wherein the compound is selected from the group consisting of:
3-[(2-pyridyl)methylhydroxyphosphinyl]-2-phenylpropanoic acid;
3-[(3-pyridyl)methylhydroxyphosphinyl]-2-phenylpropanoic acid;
3-[(4-pyridyl)methylhydroxyphosphinyl]-2-phenylpropanoic acid;
3-[(3-pyridyl)ethylhydroxyphosphinyl]-2-phenylpropanoic acid;
3-[(3-pyridyl)propylhydroxyphosphinyl]-2-phenylpropanoic acid;
3-[(tetrahydrofuranyl)methylhydroxyphosphinyl]-2-phenylpropanoic acid;
3-[(tetrahydrofuranyl)ethylhydroxyphosphinyl]-2-phenylpropanoic acid;
3-[(tetrahydrofuranyl)propylhydroxyphosphinyl]-2-phenylpropanoic acid;
3-[(2-indolyl)methylhydroxyphosphinyl]-2-phenylpropanoic acid;
3-[(3-indolyl)methylhydroxyphosphinyl]-2-phenylpropanoic acid;
3-[(4-indolyl)methylhydroxyphosphinyl]-2-phenylpropanoic acid;
3-[(3-indolyl)ethylhydroxyphosphinyl]-2-phenylpropanoic acid;
3-[(3-indolyl)propylhydroxyphosphinyl]-2-phenylpropanoic acid;
3-[(2-thienyl)methylhydroxyphosphinyl]-2-phenylpropanoic acid;
3-[(3-thienyl)methylhydroxyphosphinyl]-2-phenylpropanoic acid;
3-[(4-thienyl)methylhydroxyphosphinyl]-2-phenylpropanoic acid;
3-[(3-thienyl)ethylhydroxyphosphinyl]-2-phenylpropanoic acid;
3-[(3-thienyl)propylhydroxyphosphinyl]-2-phenylpropanoic acid;
3-(benzylhydroxyphosphinyl)-2-(2-pyridyl)methylpropanoic acid;
3-(benzylhydroxyphosphinyl)-2-(3-pyridyl)methylpropanoic acid;
3-(benzylhydroxyphosphinyl)-2-(4-pyridyl)methylpropanoic acid;
3-(benzylhydroxyphosphinyl)-2-(3-pyridyl)ethylpropanoic acid;
3-(benzylhydroxyphosphinyl)-2-(3-pyridyl)propylpropanoic acid;
3-(benzylhydroxyphosphinyl)-2-(tetrahydrofuranyl)methylpropanoic acid;
3-(benzylhydroxyphosphinyl)-2-(tetrahydrofuranyl)ethylpropanoic acid;
3-(benzylhydroxyphosphinyl)-2-(tetrahydrofuranyl)propylpropanoic acid;
3-(benzylhydroxyphosphinyl)-2-(2-indolyl)methylpropanoic acid;
3-(benzylhydroxyphosphinyl)-2-(3-indolyl)methylpropanoic acid;
3-(benzylhydroxyphosphinyl)-2-(4-indolyl)methylpropanoic acid;
3-(benzylhydroxyphosphinyl)-2-(3-indolyl)ethylpropanoic acid;
3-(benzylhydroxyphosphinyl)-2-(3-indolyl)propylpropanoic acid;
3-(benzylhydroxyphosphinyl)-2-(2-thienyl)methylpropanoic acid;
3-(benzylhydroxyphosphinyl)-2-(3-thienyl)methylpropanoic acid;
3-(benzylhydroxyphosphinyl)-2-(4-thienyl)methylpropanoic acid;
3-(benzylhydroxyphosphinyl)-2-(3-thienyl)ethylpropanoic acid;
3-(benzylhydroxyphosphinyl)-2-(3-thienyl)propylpropanoic acid;
3-((1-naphthyl)hydroxyphosphinyl)-2-phenylpropanoic acid;
3-((2-naphthyl)hydroxyphosphinyl)2-phenylpropanoic acid;
3-((1-naphthyl)methylhydroxyphosphinyl)-2-phenylpropanoic acid;
3-((2-naphthyl)methylhydroxyphosphinyl)-2-phenylpropanoic acid;
3-((1-naphthyl)ethylhydroxyphosphinyl)-2-phenylpropanoic acid;
3-((2-naphthyl)ethylhydroxyphosphinyl)-2-phenylpropanoic acid;
3-((1-naphthyl)propylhydroxyphosphinyl)-2-phenylpropanoic acid;
3-((2-naphthyl)propylhydroxyphosphinyl)-2-phenylpropanoic acid;
3-((1-naphthyl)butylhydroxyphosphinyl)-2-phenylpropanoic acid;
3-((2-naphthyl)butylhydroxyphosphinyl)-2-phenylpropanoic acid; and
pharmaceutically acceptable salts and hydrates thereof.

20. The method of claim 11, wherein:
Y is O; and
$R_2$ is substituted with carboxy.

21. The method of claim 20, wherein the compound is selected from the group consisting of:
2-[[methylhydroxyphosphinyl]oxy]pentanedioic acid;
2-[[ethylhydroxyphosphinyl]oxy]pentanedioic acid;
2-[[propylhydroxyphosphinyl]oxy]pentanedioic acid;
2-[[butylhydroxyphosphinyl]oxy]pentanedioic acid;
2-[[cyclohexylhydroxyphosphinyl]oxy]pentanedioic acid;
2-[[(cyclohexyl)methylhydroxyphosphinyl]oxy]-pentanedioic acid;
2-[[phenylhydroxyphosphinyl]oxy]pentanedioic acid;
2-[[benzylhydroxyphosphinyl]oxy]pentanedioic acid;
2-[[phenylethylhydroxyphosphinyl]oxy]pentanedioic acid;
2-[[phenylpropylhydroxyphosphinyl]oxy]pentanedioic acid;
2-[[phenylbutylhydroxyphosphinyl]oxy]pentanedioic acid;
2-[[(4-methylbenzyl)hydroxyphosphinyl]oxy]-pentanedioic acid;

2-[[(4-fluorobenzyl)hydroxyphosphinyl]oxy]-pentanedioic acid;
2-[[(2-fluorobenzyl)hydroxyphosphinyl]oxy]-pentanedioic acid;
2-[[(pentafluorobenzyl)hydroxyphosphinyl]oxy]-pentanedioic acid;
2-[[(methoxybenzyl)hydroxyphosphinyl]oxy]-pentanedioic acid;
2-[[(2,3,4-trimethoxyphenyl)hydroxyphosphinyl]oxy]-pentanedioic acid;
2-[[(1-naphthyl)hydroxyphosphinyl]oxy]pentanedioic acid;
2-[[(2-naphthyl)hydroxyphosphinyl]oxy]pentanedioic acid;
2-[[(1-naphthyl)methylhydroxyphosphinyl]oxy]-pentanedioic acid;
2-[[(2-naphthyl)methylhydroxyphosphinyl]oxy]-pentanedioic acid;
2-[[(1-naphthyl)ethylhydroxyphosphinyl]oxy]-pentanedioic acid;
2-[[(2-naphthyl)ethylhydroxyphosphinyl]oxy]-pentanedioic acid;
2-[[(1-naphthyl)propylhydroxyphosphinyl]oxy]-pentanedioic acid;
2-[[(2-naphthyl)propylhydroxyphosphinyl]oxy]-pentanedioic acid;
2-[[(1-naphthyl)butylhydroxyphosphinyl]oxy]-pentanedioic acid;
2-[[(2-naphthyl)butylhydroxyphosphinyl]oxy]-pentanedioic acid;
2-[[(phenylprop-2-enyl)hydroxyphosphinyl]oxy]-pentanedioic acid;
2-[[benzylhydroxyphosphinyl]oxy]pentanedioic acid;
2-[[((hydroxy)phenylmethyl)hydroxyphosphinyl]oxy]-pentanedioic acid;
2-[[(3-methylbenzyl)hydroxyphosphinyl]oxy]-pentanedioic acid;
2-[[(4-fluorophenyl)hydroxyphosphinyl]oxy]-pentanedioic acid;
2-[[(2-fluorobenzyl)hydroxyphosphinyl]oxy]-pentanedioic acid;
2-(phosphono)oxy]pentanedioic acid;
2-[[(3-trifluoromethylbenzyl)hydroxyphosphinyl]oxy]-pentanedioic acid;
2-[[methylhydroxyphosphinyl]oxy]-2-phenylethanoic acid;
2-[[ethylhydroxyphosphinyl]oxy]-2-phenylethanoic acid;
2-[[propylhydroxyphosphinyl]oxy]-2-phenylethanoic acid;
2-[[butylhydroxyphosphinyl]oxy]-2-phenylethanoic acid;
2-[[cyclohexylhydroxyphosphinyl]oxy]-2-phenylethanoic acid;
2-[[(cyclohexyl)methylhydroxyphosphinyl]oxy]-2-phenylethanoic acid;
2-[[phenylhydroxyphosphinyl]oxy]-2-phenylethanoic acid;
2-[[benzylhydroxyphosphinyl]oxy]-2-phenylethanoic acid;
2-[[phenylethylhydroxyphosphinyl]oxy]-2-phenylethanoic acid;
2-[[phenylpropylhydroxyphosphinyl]oxy]-2-phenylethanoic acid;
2-[[phenylbutylhydroxyphosphinyl]oxy]-2-phenylethanoic acid;
2-[[(2,3,4-trimethoxyphenyl)-3-hydroxyphosphinyl]oxy]-2-phenylethanoic acid;
2-[[(1-naphthyl)hydroxyphosphinyl]oxy]-2-phenylethanoic acid;
2-[[(2-naphthyl)hydroxyphosphinyl]oxy]-2-phenylethanoic acid;
2-[[(1-naphthyl)methylhydroxyphosphinyl]oxy]-2-phenylethanoic acid;
2-[[(2-naphthyl)methylhydroxyphosphinyl]oxy]-2-phenylethanoic acid;
2-[[(1-naphthyl)ethylhydroxyphosphinyl]oxy]-2-phenylethanoic acid;
2-[[(2-naphthyl)ethylhydroxyphosphinyl]oxy]-2-phenylethanoic acid;
2-[[(1-naphthyl)propylhydroxyphosphinyl]oxy]-2-phenylethanoic acid;
2-[[(2-naphthyl)propylhydroxyphosphinyl]oxy]-2-phenylethanoic acid;
2-[[(1-naphthyl)butylhydroxyphosphinyl]oxy]-2-phenylethanoic acid;
2-[[(2-naphthyl)butylhydroxyphosphinyl]oxy]-2-phenylethanoic acid;
2-[[phenylprop-2-enylhydroxyphosphinyl]oxy]-2-phenylethanoic acid;
2-[(methylhydroxyphosphinyl)oxy]hexanedioic acid;
2-[(benzylhydroxyphosphinyl)oxy]hexanedioic acid;
2-[(methylhydroxyphosphinyl)oxy]heptanedioic acid;
2-[(benzylhydroxyphosphinyl)oxy]heptanedioic acid;
2-[(methylhydroxyphosphinyl)oxy]octanedioic acid;
2-[(benzylhydroxyphosphinyl)oxy]octanedioic acid;
2-[(methylhydroxyphosphinyl)oxy]nonanedioic acid;
2-[(benzylhydroxyphosphinyl)oxy]nonanedioic acid;
2-[(methylhydroxyphosphinyl)oxy]decanedioic acid;
2-[(benzylhydroxyphosphinyl)oxy]decanedioic acid;
2-[[benzylhydroxyphosphinyl]oxy]-2-methylethanoic acid;
2-[[benzylhydroxyphosphinyl]oxy]-2-ethylethanoic acid;
2-[[benzylhydroxyphosphinyl]oxy]-2-propylethanoic acid;
2-[[benzylhydroxyphosphinyl]oxy]-2-butylethanoic acid;
2-[[benzylhydroxyphosphinyl]oxy]-2-cyclohexylethanoic acid;
2-[[benzylhydroxyphosphinyl]oxy]-2-(cyclohexyl)methylethanoic acid;
2-[[benzylhydroxyphosphinyl]oxy]-2-phenylethanoic acid;
2-[[benzylhydroxyphosphinyl]oxy]-2-benzylethanoic acid;
2-[[benzylhydroxyphosphinyl]oxy]-2-phenylethylethanoic acid;
2-[[benzylhydroxyphosphinyl]oxy]-2-phenylpropylethanoic acid;
2-[[benzylhydroxyphosphinyl]oxy]-2-phenylbutylethanoic acid;
2-[[benzylhydroxyphosphinyl]oxy]-2-(2,3,4-trimethoxyphenyl)ethanoic acid;
2-[[benzylhydroxyphosphinyl]oxy]-2-(1-naphthyl)ethanoic acid;
2-[[benzylhydroxyphosphinyl]oxy]-2-(2-naphthyl)ethanoic acid;
2-[[benzylhydroxyphosphinyl]oxy]-2-(1-naphthyl)methylethanoic acid;
2-[[benzylhydroxyphosphinyl]oxy]-2-(2-naphthyl)methylethanoic acid;
2-[[benzylhydroxyphosphinyl]oxy]-2-(1-naphthyl)ethylethanoic acid;
2-[[benzylhydroxyphosphinyl]oxy]-2-(2-naphthyl)ethylethanoic acid;
2-[[benzylhydroxyphosphinyl]oxy]-2-(1-naphthyl)propylethanoic acid;
2-[[benzylhydroxyphosphinyl]oxy]-2-(2-naphthyl)propylethanoic acid;
2-[[benzylhydroxyphosphinyl]oxy]-2-(1-naphthyl)butylethanoic acid;
2-[[benzylhydroxyphosphinyl]oxy]-2-(2-naphthyl)butylethanoic acid;
2-[[benzylhydroxyphosphinyl]oxy]-2-phenylprop-2-enylethanoic acid;
2-[[(2-pyridyl)methylhydroxyphosphinyl]oxy]-pentanedioic acid;
2-[[(3-pyridyl)methylhydroxyphosphinyl]oxy]-pentanedioic acid;

2-[[(4-pyridyl)methylhydroxyphosphinyl]oxy]-pentanedioic acid;
2-[[(3-pyridyl)ethylhydroxyphosphinyl]oxy]-pentanedioic acid;
2-[[(3-pyridyl)propylhydroxyphosphinyl]oxy]-pentanedioic acid;
2-[[(tetrahydrofuranyl)methylhydroxyphosphinyl]oxy]-pentanedioic acid;
2-[[(tetrahydrofuranyl)ethylhydroxyphosphinyl]oxy]-pentanedioic acid;
2-[[(tetrahydrofuranyl)propylhydroxyphosphinyl]oxy]-pentanedioic acid;
2-[[(2-indolyl)methylhydroxyphosphinyl]oxy]-pentanedioic acid;
2-[[(3-indolyl)methylhydroxyphosphinyl]oxy]-pentanedioic acid;
2-[[(4-indolyl)methylhydroxyphosphinyl]oxy]-pentanedioic acid;
2-[[(3-indolyl)ethylhydroxyphosphinyl]oxy]-pentanedioic acid;
2-[[(3-indolyl)propylhydroxyphosphinyl]oxy]-pentanedioic acid;
2-[[(2-thienyl)methylhydroxyphosphinyl]oxy]-pentanedioic acid;
2-[[(3-thienyl)methylhydroxyphosphinyl]oxy]-pentanedioic acid;
2-[[(4-thienyl)methylhydroxyphosphinyl]oxy]-pentanedioic acid;
2-[[(3-thienyl)ethylhydroxyphosphinyl]oxy]-pentanedioic acid;
2-[[(3-thienyl)propylhydroxyphosphinyl]oxy]-pentanedioic acid; and pharmaceutically acceptable salts and hydrates thereof.

22. The method of claim 11, wherein:

Y is O or NR$_5$; and

R$_2$ is selected from the group consisting of hydrogen, C$_1$–C$_9$ straight or branched chain alkyl, C$_2$–C$_9$ straight or branched chain alkenyl, C$_3$–C$_8$ cycloalkyl, C$_5$–C$_7$ cycloalkenyl, benzyl and phenyl, wherein said R$_2$ is unsubstituted or substituted with C$_3$–C$_8$ cycloalkyl, C$_5$–C$_7$ cycloalkenyl, C$_1$–C$_6$ straight or branched chain alkyl, C$_2$–C$_6$ straight or branched chain alkenyl, C$_1$–C$_4$ alkoxy, carboxy, phenyl, or mixtures thereof.

23. The method of claim 22, wherein the compound is selected from the group consisting of:

2-[[(2-pyridyl)methylhydroxyphosphinyl]oxy]-2-phenylethanoic acid;
2-[[(3-pyridyl)methylhydroxyphosphinyl]oxy]-2-phenylethanoic acid;
2-[[(4-pyridyl)methylhydroxyphosphinyl]oxy]-2-phenylethanoic acid;
2-[[(3-pyridyl)ethylhydroxyphosphinyl]oxy]-2-phenylethanoic acid;
2-[[(3-pyridyl)propylhydroxyphosphinyl]oxy]-2-phenylethanoic acid;
2-[[(tetrahydrofuranyl)methylhydroxyphosphinyl]oxy]-2-phenylethanoic acid;
2-[[(tetrahydrofuranyl)ethylhydroxyphosphinyl]oxy]-2-phenylethanoic acid;
2-[[(tetrahydrofuranyl)propylhydroxyphosphinyl]oxy]-2-phenylethanoic acid;
2-[[(2-indolyl)methylhydroxyphosphinyl]oxy]-2-phenylethanoic acid;
2-[[(3-indolyl)methylhydroxyphosphinyl]oxy]-2-phenylethanoic acid;
2-[[(4-indolyl)methylhydroxyphosphinyl]oxy]-2-phenylethanoic acid;
2-[[(3-indolyl)ethylhydroxyphosphinyl]oxy]-2-phenylethanoic acid;
2-[[(3-indolyl)propylhydroxyphosphinyl]oxy]-2-phenylethanoic acid;
2-[[(2-thienyl)methylhydroxyphosphinyl]oxy]-2-phenylethanoic acid;
2-[[(3-thienyl)methylhydroxyphosphinyl]oxy]-2-phenylethanoic acid;
2-[[(4-thienyl)methylhydroxyphosphinyl]oxy]-2-phenylethanoic acid;
2-[[(3-thienyl)ethylhydroxyphosphinyl]oxy]-2-phenylethanoic acid;
2-[[(3-thienyl)propylhydroxyphosphinyl]oxy]-2-phenylethanoic acid;
2-[[benzylhydroxyphosphinyl]oxy]-2-(2-pyridyl)methylethanoic acid;
2-[[benzylhydroxyphosphinyl]oxy]-2-(3-pyridyl)methylethanoic acid;
2-[[benzylhydroxyphosphinyl]oxy]-2-(4-pyridyl)methylethanoic acid;
2-[[benzylhydroxyphosphinyl]oxy]-2-(3-pyridyl)ethylethanoic acid;
2-[[benzylhydroxyphosphinyl]oxy]-2-(3-pyridyl)propylethanoic acid;
2-[[benzylhydroxyphosphinyl]oxy]-2-(tetrahydrofuranyl)methylethanoic acid;
2-[[benzylhydroxyphosphinyl]oxy]-2-(tetrahydrofuranyl)-ethylethanoic acid;
2-[[benzylhydroxyphosphinyl]oxy]-2-(tetrahydrofuranyl)-propylethanoic acid;
2-[[benzylhydroxyphosphinyl]oxy]-2-(2-indolyl)methylethanoic acid;
2-[[benzylhydroxyphosphinyl]oxy]-2-(3-indolyl)methylethanoic acid;
2-[[benzylhydroxyphosphinyl]oxy]-2-(4-indolyl)methylethanoic acid;
2-[[benzylhydroxyphosphinyl]oxy]-2-(3-indolyl)ethylethanoic acid;
2-[[benzylhydroxyphosphinyl]oxy]-2-(3-indolyl)propylethanoic acid;
2-[[benzylhydroxyphosphinyl]oxy]-2-(2-thienyl)methylethanoic acid;
2-[[benzylhydroxyphosphinyl]oxy]-2-(3-thienyl)methylethanoic acid;
2-[[benzylhydroxyphosphinyl]oxy]-2-(4-thienyl)methylethanoic acid;
2-[[benzylhydroxyphosphinyl]oxy]-2-(3-thienyl)ethylethanoic acid;
2-[[benzylhydroxyphosphinyl]oxy]-2-(3-thienyl)propylethanoic acid;
2-[[methylhydroxyphosphinyl]amino]pentanedioic acid;
2-[[ethylhydroxyphosphinyl]amino]pentanedioic acid;
2-[[propylhydroxyphosphinyl]amino]pentanedioic acid;
2-[[butylhydroxyphosphinyl]amino]pentanedioic acid;
2-[[cyclohexylhydroxyphosphinyl]amino]pentanedioic acid;
2-[[(cyclohexyl)methylhydroxyphosphinyl]amino]-pentanedioic acid;
2-[[phenylhydroxyphosphinyl]amino]pentanedioic acid;
2-[[benzylhydroxyphosphinyl]amino]pentanedioic acid;
2-[[phenylethylhydroxyphosphinyl]amino]pentanedioic acid;
2-[[phenylpropylhydroxyphosphinyl]amino]pentanedioic acid;
2-[[phenylbutylhydroxyphosphinyl]amino]pentanedioic acid;
2-[[(4-methylbenzyl)hydroxyphosphinyl]amino]-pentanedioic acid;

2-[[(4-fluorobenzyl)hydroxyphosphinyl]amino]-pentanedioic acid;
2-[[(2-fluorobenzyl)hydroxyphosphinyl]amino]-pentanedioic acid;
2-[[(pentafluorobenzyl)hydroxyphosphinyl]amino]-pentanedioic acid;
2-[[(methoxybenzyl)hydroxyphosphinyl]amino]-pentanedioic acid;
2-[[(2,3,4-trimethoxyphenyl)hydroxyphosphinyl]-amino]pentanedioic acid;
2-[[(1-naphthyl)hydroxyphosphinyl]amino]pentanedioic acid;
2-[[(2-naphthyl)hydroxyphosphinyl]amino]pentanedioic acid;
2-[[(1-naphthyl)methylhydroxyphosphinyl]amino]-pentanedioic acid;
2-[[(2-naphthyl)methylhydroxyphosphinyl]amino]-pentanedioic acid;
2-[[(1-naphthyl)ethylhydroxyphosphinyl]amino]-pentanedioic acid;
2-[[(2-naphthyl)ethylhydroxyphosphinyl]amino]-pentanedioic acid;
2-[[(1-naphthyl)propylhydroxyphosphinyl]amino]-pentanedioic acid;
2-[[(2-naphthyl)propylhydroxyphosphinyl]amino]-pentanedioic acid;
2-[[(1-naphthyl)butylhydroxyphosphinyl]amino]-pentanedioic acid;
2-[[(2-naphthyl)butylhydroxyphosphinyl]amino]-pentanedioic acid;
2-[[(phenylprop-2-enyl)hydroxyphosphinyl]amino]pentanedioic acid;
2-[[benzylhydroxyphosphinyl]amino]pentanedioic acid;
2-[[(2-fluorobenzyl)hydroxyphosphinyl]amino]-2-pentanedioic acid;
2-[[((hydroxy)phenylmethyl)hydroxyphosphinyl]amino]-pentanedioic acid;
2-[[(3-methylbenzyl)hydroxyphosphinyl]amino]-pentanedioic acid;
2-[[(4-fluorophenyl)hydroxyphosphinyl]amino]-pentanedioic acid;
2-[(phosphono)amino]pentanedioic acid;
2-[[(3-trifluoromethylbenzyl)hydroxyphosphinyl]-amino]pentanedioic acid;
2-[(methylhydroxyphosphinyl)amino]hexanedioic acid;
2-[(benzylhydroxyphosphinyl)amino]hexanedioic acid;
2-[(methylhydroxyphosphinyl)amino]heptanedioic acid;
2-[(benzylhydroxyphosphinyl)amino]heptanedioic acid;
2-[(methylhydroxyphosphinyl)amino]octanedioic acid;
2-[(benzylhydroxyphosphinyl)amino]octanedioic acid;
2-[(methylhydroxyphosphinyl)amino]nonanedioic acid;
2-[(benzylhydroxyphosphinyl)amino]nonanedioic acid;
2-[(methylhydroxyphosphinyl)amino]decanedioic acid;
2-[(benzylhydroxyphosphinyl)amino]decanedioic acid;
3-[[(2-pyridyl)methylhydroxyphosphinyl]amino]-pentanedioic acid;
3-[[(3-pyridyl)methylhydroxyphosphinyl]amino]-pentanedioic acid;
3-[[(4-pyridyl)methylhydroxyphosphinyl]amino]-pentanedioic acid;
3-[[(3-pyridyl)ethylhydroxyphosphinyl]amino]-pentanedioic acid;
3-[[(3-pyridyl)propylhydroxyphosphinyl]amino]-pentanedioic acid;
3-[[(tetrahydrofuranyl)methylhydroxyphosphinyl]-amino]pentanedioic acid;
3-[[(tetrahydrofuranyl)ethylhydroxyphosphinyl]-amino]pentanedioic acid;
3-[[(tetrahydrofuranyl)propylhydroxyphosphinyl]-amino]pentanedioic acid;
3-[[(2-indolyl)methylhydroxyphosphinyl]amino]-pentanedioic acid;
3-[[(3-indolyl)methylhydroxyphosphinyl]amino]-pentanedioic acid;
3-[[(4-indolyl)methylhydroxyphosphinyl]amino]-pentanedioic acid;
3-[[(3-indolyl)ethylhydroxyphosphinyl]amino]-pentanedioic acid;
3-[[(3-indolyl)propylhydroxyphosphinyl]amino]-pentanedioic acid;
3-[[(2-thienyl)methylhydroxyphosphinyl]amino]-pentanedioic acid;
3-[[(3-thienyl)methylhydroxyphosphinyl]amino]-pentanedioic acid;
3-[[(4-thienyl)methylhydroxyphosphinyl]amino]-pentanedioic acid;
3-[[(3-thienyl)ethylhydroxyphosphinyl]amino]-pentanedioic acid;
3-[[(3-thienyl)propylhydroxyphosphinyl]amino]-pentanedioic acid;
2-[[methylhydroxyphosphinyl]amino]-2-phenylethanoic acid;
2-[[ethylhydroxyphosphinyl]amino]-2-phenylethanoic acid;
2-[[propylhydroxyphosphinyl]amino]-2-phenylethanoic acid;
2-[[butylhydroxyphosphinyl]amino]-2-phenylethanoic acid;
2-[[cyclohexylhydroxyphosphinyl]amino]-2-phenylethanoic acid;
2-[[(cyclohexyl)methylhydroxyphosphinyl]amino]-2-phenylethanoic acid;
2-[[phenylhydroxyphosphinyl]amino]-2-phenylethanoic acid;
2-[[benzylhydroxyphosphinyl]amino]-2-phenylethanoic acid;
2-[[phenylethylhydroxyphosphinyl]amino]-2-phenylethanoic acid;
2-[[phenylpropylhydroxyphosphinyl]amino]-2-phenylethanoic acid;
2-[[phenylbutylhydroxyphosphinyl]amino]-2-phenylethanoic acid;
2-[[(2,3,4-trimethoxyphenyl)-3-hydroxyphosphinyl]amino]-2-phenylethanoic acid;
2-[[(1-naphthyl)hydroxyphosphinyl]amino]-2-phenylethanoic acid;
2-[[(2-naphthyl)hydroxyphosphinyl]amino]-2-phenylethanoic acid;
2-[[(1-naphthyl)methylhydroxyphosphinyl]amino]-2-phenylethanoic acid;
2-[[(2-naphthyl)methylhydroxyphosphinyl]amino]-2-phenylethanoic acid;
2-[[(1-naphthyl)ethylhydroxyphosphinyl]amino]-2-phenylethanoic acid;
2-[[(2-naphthyl)ethylhydroxyphosphinyl]amino]-2-phenylethanoic acid;
2-[[(1-naphthyl)propylhydroxyphosphinyl]amino]-2-phenylethanoic acid;
2-[[(2-naphthyl)propylhydroxyphosphinyl]amino]-2-phenylethanoic acid;
2-[[(1-naphthyl)butylhydroxyphosphinyl]amino]-2-phenylethanoic acid;
2-[[(2-naphthyl)butylhydroxyphosphinyl]amino]-2-phenylethanoic acid;
2-[[phenylprop-2-enylhydroxyphosphinyl]amino]-2-phenylethanoic acid;
2-[[benzylhydroxyphosphinyl]amino]-2-methylethanoic acid;

2-[[benzylhydroxyphosphinyl]amino]-2-ethylethanoic acid;
2-[[benzylhydroxyphosphinyl]amino]-2-propylethanoic acid;
2-[[benzylhydroxyphosphinyl]amino]-2-butylethanoic acid;
2-[[benzylhydroxyphosphinyl]amino]-2-cyclohexylethanoic acid;
2-[[benzylhydroxyphosphinyl]amino]-2-(cyclohexyl)methylethanoic acid;
2-[[benzylhydroxyphosphinyl]amino]-2-phenylethanoic acid;
2-[[benzylhydroxyphosphinyl]amino]-2-benzylethanoic acid;
2-[[benzylhydroxyphosphinyl]amino]-2-phenylethylethanoic acid;
2-[[benzylhydroxyphosphinyl]amino]-2-phenylpropylethanoic acid;
2-[[benzylhydroxyphosphinyl]amino]-2-phenylbutylethanoic acid;
2-[[benzylhydroxyphosphinyl]amino]-2-(2,3,4-trimethoxyphenyl)ethanoic acid;
2-[[benzylhydroxyphosphinyl]amino]-2-(1-naphthyl)ethanoic acid;
2-[[benzylhydroxyphosphinyl]amino]-2-(2-naphthyl)ethanoic acid;
2-[[benzylhydroxyphosphinyl]amino]-2-(1-naphthyl)methylethanoic acid;
2-[[benzylhydroxyphosphinyl]amino]-2-(2-naphthyl)methylethanoic acid;
2-[[benzylhydroxyphosphinyl]amino]-2-(1-naphthyl)ethylethanoic acid;
2-[[benzylhydroxyphosphinyl]amino]-2-(2-naphthyl)ethylethanoic acid;
2-[[benzylhydroxyphosphinyl]amino]-2-(1-naphthyl)propylethanoic acid;
2-[[benzylhydroxyphosphinyl]amino]-2-(2-naphthyl)propylethanoic acid;
2-[[benzylhydroxyphosphinyl]amino]-2-(1-naphthyl)butylethanoic acid;
2-[[benzylhydroxyphosphinyl]amino]-2-(2-naphthyl)butylethanoic acid;
2-[[benzylhydroxyphosphinyl]amino]-2-phenolprop-2-enylethanoic acid;
2-[[(2-pyridyl)methylhydroxyphosphinyl]amino]-2-phenylethanoic acid;
2-[[(3-pyridyl)methylhydroxyphosphinyl]amino]-2-phenylethanoic acid;
2-[[(4-pyridyl)methylhydroxyphosphinyl]amino]-2-phenylethanoic acid;
2-[[(3-pyridyl)ethylhydroxyphosphinyl]amino]-2-phenylethanoic acid;
2-[[(3-pyridyl)propylhydroxyphosphinyl]amino]-2-phenylethanoic acid;
2-[[(tetrahydrofuranyl)methylhydroxyphosphinyl]-amino]-2-phenylethanoic acid;
2-[[(tetrahydrofuranyl)ethylhydroxyphosphinyl]-amino]-2-phenylethanoic acid;
2-[[(tetrahydrofuranyl)propylhydroxyphosphinyl]-amino]-2-phenylethanoic acid;
2-[[(2-indolyl)methylhydroxyphosphinyl]amino]-2-phenylethanoic acid;
2-[[(3-indolyl)methylhydroxyphosphinyl]amino]-2-phenylethanoic acid;
2-[[(4-indolyl)methylhydroxyphosphinyl]amino]-2-phenylethanoic acid;
2-[[(3-indolyl)ethylhydroxyphosphinyl]amino]-2-phenylethanoic acid;
2-[[(3-indolyl)propylhydroxyphosphinyl]amino]-2-phenylethanoic acid;
2-[[(2-thienyl)methylhydroxyphosphinyl]amino]-2-phenylethanoic acid;
2-[[(3-thienyl)methylhydroxyphosphinyl]amino]-2-phenylethanoic acid;
2-[[(4-thienyl)methylhydroxyphosphinyl]amino]-2-phenylethanoic acid;
2-[[(3-thienyl)ethylhydroxyphosphinyl]amino]-2-phenylethanoic acid;
2-[[(3-thienyl)propylhydroxyphosphinyl]amino]-2-phenylethanoic acid;
2-[[benzylhydroxyphosphinyl]amino]-2-(2-pyridyl)methylethanoic acid;
2-[[benzylhydroxyphosphinyl]amino]-2-(3-pyridyl)methylethanoic acid;
2-[[benzylhydroxyphosphinyl]amino]-2-(4-pyridyl)methylethanoic acid;
2-[[benzylhydroxyphosphinyl]amino]-2-(3-pyridyl)ethylethanoic acid;
2-[[benzylhydroxyphosphinyl]amino]-2-(3-pyridyl)propylethanoic acid;
2-[[benzylhydroxyphosphinyl]amino]-2-(tetrahydrofuranyl)methylethanoic acid;
2-[[benzylhydroxyphosphinyl]amino]-2-(tetrahydrofuranyl)ethylethanoic acid;
2-[[benzylhydroxyphosphinyl]amino]-2-(tetrahydrofuranyl)propylethanoic acid;
2-[[benzylhydroxyphosphinyl]amino]-2-(2-indolyl)methylethanoic acid;
2-[[benzylhydroxyphosphinyl]amino]-2-(3-indolyl)methylethanoic acid;
2-[[benzylhydroxyphosphinyl]amino]-2-(4-indolyl)methylethanoic acid;
2-[[benzylhydroxyphosphinyl]amino]-2-(3-indolyl)ethylethanoic acid;
2-[[benzylhydroxyphosphinyl]amino]-2-(3-indolyl)propylethanoic acid;
2-[[benzylhydroxyphosphinyl]amino]-2-(2-thienyl)methylethanoic acid;
2-[[benzylhydroxyphosphinyl]amino]-2-(3-thienyl)methylethanoic acid;
2-[[benzylhydroxyphosphinyl]amino]-2-(4-thienyl)methylethanoic acid;
2-[[benzylhydroxyphosphinyl]amino]-2-(3-thienyl)ethylethanoic acid;
2-[[benzylhydroxyphosphinyl]amino]-2-(3-thienyl)propylethanoic acid; and pharmaceutically acceptable salts and hydrates thereof.

24. The method of claim 1, wherein the NAALADase inhibitor is a compound of Formula II:

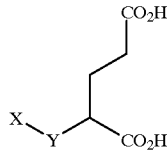

or a pharmaceutically acceptable salt or hydrate thereof, wherein:

X is

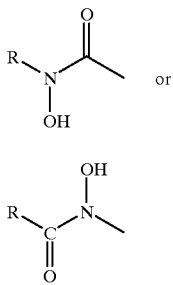

Y is $CR_1R_2$, $NR_3$ or O;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, Ar and mixtures thereof, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar, or a mixture thereof; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, or a mixture thereof.

25. The method of claim 24, wherein:

Y is $CH_2$; and

R is selected from the group consisting of hydrogen, $C_1$–$C_4$ straight or branched chain alkyl, 4-pyridyl, benzyl and phenyl, said R having one to three substituent(s) independently selected from the group consisting of hydrogen, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar, and mixtures thereof.

26. The method of claim 25, wherein the compound is selected from the group consisting of:

2-[[(N-hydroxy)carbamoyl]methyl]pentanedioic acid;
2-[[(N-hydroxy-N-methyl)carbamoyl]methyl]pentanedioic acid;
2-[[(N-butyl-N-hydroxy)carbamoyl]methyl]pentanedioic acid;
2-[[(N-benzyl-N-hydroxy)carbamoyl]methyl]pentanedioic acid;
2-[[(N-hydroxy-N-phenyl)carbamoyl]methyl]pentanedioic acid;
2-[[(N-hydroxy-N-2-phenylethyl)carbamoyl]methyl] pentanedioic acid;
2-[[(N-ethyl-N-hydroxy)carbamoyl]methyl]pentanedioic acid;
2-[[(N-hydroxy-N-propyl)carbamoyl]methyl]pentanedioic acid;
2-[[(N-hydroxy-N-3-phenylpropyl)carbamoyl]methyl] pentanedioic acid;
2-[[(N-hydroxy-N-4-pyridyl)carbamoyl]methyl] pentanedioic acid;
2-[[(N-hydroxy)carboxamido]methyl]pentanedioic acid;
2-[[N-hydroxy(methyl)carboxamido]methyl]pentanedioic acid;
2-[[N-hydroxy(benzyl)carboxamido]methyl]pentanedioic acid;
2-[[N-hydroxy(phenyl)carboxamido]methyl]pentanedioic acid;
2-[[N-hydroxy(2-phenylethyl)carboxamido]methyl] pentanedioic acid;
2-[[N-hydroxy(ethyl)carboxamido]methyl]pentanedioic acid;
2-[[N-hydroxy(propyl)carboxamido]methyl]pentanedioic acid;
2-[[N-hydroxy(3-phenylpropyl)carboxamido]methyl] pentanedioic acid; and
2-[[N-hydroxy(4-pyridyl)carboxamido]methyl] pentanedioic acid.

27. The method of claim 1, wherein the NAALADase inhibitor is a compound of Formula V:

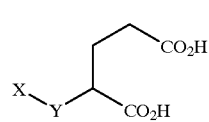

or a pharmaceutically acceptable salt or hydrate thereof, wherein:

X is selected from the group consisting of

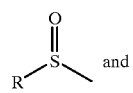

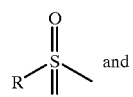

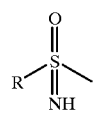

Y is $CR_1R_2$, $NR_3$ or O;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar, or a mixture thereof; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, said Ar having one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, and mixtures thereof.

28. The method of claim 27, wherein:

at least one of said $R_1$, $R_2$ and $R_3$ is/are independently substituted with $C_3$–$C_8$ cycloalkyl, $C_5$–$C_7$ cycloalkenyl, hydroxy, halo, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar, or a mixture thereof;

Y is $CH_2$; and

R is selected from the group consisting of hydrogen, $C_1$–$C_4$ straight or branched chain alkyl, 4-pyridyl, benzyl and phenyl, said R having one to three substituent(s) independently selected from the group consisting of hydrogen, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, and Ar.

29. The method of claim 28, wherein the compound is selected from the group consisting of:

2-[(sulfinyl)methyl]pentanedioic acid;
2-[(methylsulfinyl)methyl]pentanedioic acid;
2-[(ethylsulfinyl)methyl]pentanedioic acid;
2-[(propylsulfinyl)methyl]pentanedioic acid;
2-[(butylsulfinyl)methyl]pentanedioic acid;
2-[(phenylsulfinyl]methyl]pentanedioic acid;
2-[[(2-phenylethyl)sulfinyl]methyl]pentanedioic acid;
2-[[(3-phenylpropyl)sulfinyl]methyl]pentanedioic acid;
2-[[(4-pyridyl)sulfinyl]methyl]pentanedioic acid;
2-[(benzylsulfinyl)methyl]pentanedioic acid;
2-(sulfonyl)methyl]pentanedioic acid;
2-[(methylsulfonyl)methyl]pentanedioic acid;
2-[(ethylsulfonyl)methyl]pentanedioic acid;
2-[(propylsulfonyl)methyl]pentanedioic acid;
2-[(butylsulfonyl)methyl]pentanedioic acid;
2-[(phenylsulfonyl]methyl]pentanedioic acid;
2-[[(2-phenylethyl)sulfonyl]methyl]pentanedioic acid;
2-[[(3-phenylpropyl)sulfonyl]methyl]pentanedioic acid;
2-[[(4-pyridyl)sulfonyl]methyl]pentanedioic acid; and
2-[(benzylsulfinyl)methyl]pentanedioic acid;
2-[(sulfoximinyl)methyl]pentanedioic acid;
2-[(methylsulfoximinyl)methyl]pentanedioic acid;
2-[(ethylsulfoximinyl)methyl]pentanedioic acid;
2-[(propylsulfoximinyl)methyl]pentanedioic acid;
2-[(butylsulfoximinyl)methyl]pentanedioic acid;
2-[(phenylsulfoximinyl]methyl]pentanedioic acid;
2-[[(2-phenylethyl)sulfoximinyl]methyl]pentanedioic acid;
2-[[(3-phenylpropyl)sulfoximinyl]methyl]pentanedioic acid;
2-[[(4-pyridyl)sulfoximinyl]methyl]pentanedioic acid; and
2-[(benzylsulfoximinyl)methyl]pentanedioic acid.

30. The method of claim 1, wherein the NAALADase inhibitor is a compound of Formula IX:

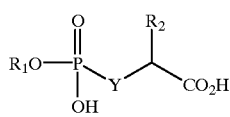

IX or a pharmaceutically acceptable salt or hydrate thereof, wherein:

Y is $CR_3R_4$, $NR_5$ or O;

$R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar, or a mixture thereof;

$R_1$, $R_3$, $R_4$ and $R_5$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar, or a mixture thereof; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, and mixtures thereof.

31. The method of claim 30, wherein the compound is selected from the group consisting of:

phosphonopropanoic acid;
2-methyl-3-phosphonopropanoic acid;
2-ethyl-3-phosphonopropanoic acid;
2-propyl-3-phosphonopropanoic acid;
2-butyl-3-phosphonopropanoic acid;
2-phenyl-3-phosphonopropanoic acid;
2-(2-phenylethyl)-3-phosphonopropanoic acid;
2-(3-phenylpropyl)-3-phosphonopropanoic acid;
2-(4-pyridyl)-3-phosphonopropanoic acid;
2-benzyl-3-phosphonopropanoic acid;
2-(hydrohydroxyphosphonomethyl)pentanedioic acid;
2-(hydromethoxyphosphonomethyl)pentanedioic acid;
2-(hydroethoxyphosphonomethyl)pentanedioic acid;
2-(hydropropoxyphosphonomethyl)pentanedioic acid;
2-(hydrobutoxyphosphonomethyl)pentanedioic acid;
2-(hydrophenoxyphosphonomethyl)pentanedioic acid;
2-[hydro(2-phenylethoxy)phosphonomethyl]pentanedioic acid;
2-[hydro(3-phenylpropoxy)phosphonomethyl]pentanedioic acid;
2-[hydro(4-pyridyloxy)phosphonomethyl]pentanedioic acid; and
2-(hydrobenzyloxyphosphonomethyl)pentanedioic acid.

32. The method of claim 1, wherein the NAALADase inhibitor is a compound of Formula X:

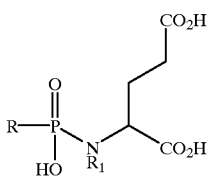

or a pharmaceutically acceptable salt or hydrate thereof, wherein:
R and $R_1$ are independently selected from the group consisting of hydrogen, $C_1$–$C_9$ straight or branched chain alkyl or alkenyl group, $C_3$–$C_8$ cycloalkyl, $C_3$ or $C_5$ cycloalkyl, $C_5$–$C_7$ cycloalkenyl and Ar, wherein said R and $R_1$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar, or a mixture thereof; and Ar is selected from the group consisting of 1-napthyl, 2-napthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1$–$C_6$ straight or branched alkyl, $C_2$–$C_6$ straight or branched chain alkenyl, $C_1$–$C_6$ alkoxy, $C_2$–$C_6$ alkenyloxy, phenoxy, benzyloxy, amino, or a mixture thereof.

33. The method of claim 32, wherein the compound is selected from the group consisting of:
N-[methylhydroxyphosphinyl]glutamic acid;
N-[ethylhydroxyphosphinyl]glutamic acid;
N-[propylhydroxyphosphinyl]glutamic acid;
N-[butylhydroxyphosphinyl]glutamic acid;
N-[phenylhydroxyphosphinyl]glutamic acid;
N-[(phenylmethyl)hydroxyphosphinyl]glutamic acid;
N-[((2-phenylethyl)methyl)hydroxyphosphinyl]glutamic acid; and
N-methyl-N-[phenylhydroxyphosphinyl]glutamic acid.

34. The method of claim 1, wherein the NAALADase inhibitor is a compound of Formula XI:

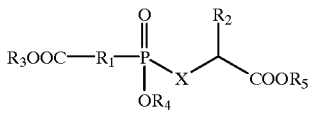

or a pharmaceutically acceptable salt, hydrate or prodrug thereof, wherein:
X is $C_6R_7$, O or $NR_8$;
$R_1$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$ is unsubstituted or substituted with one or more substituent(s) independently selected from the group consisting of carboxy, carbonyl, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, and amino, and Ar;

$R_2$, $R_3$, $R_4$, $R_5$, $R_6$, $R_7$, and $R_8$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$, $R_3$, $R_4$, $R_5$, $R_6$, $R_7$, and $R_8$ are independently unsubstituted or substituted with one or more substituent(s) independently selected from the group consisting of carboxy, carbonyl, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with one or more substituent(s) independently selected from the group consisting of carboxy, carbonyl, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, and amino.

35. The method of claim 34, wherein:
X is $CH_2$;
$R_2$ is —$(CH_2)_2COOR_9$;
$R_9$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_9$ is unsubstituted or substituted with one or more substituent(s) independently selected from the group consisting of carboxy, carbonyl, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, and Ar; and $R_3$, $R_4$, $R_5$, and $R_9$ are hydrogen.

36. The method of claim 35, wherein the compound is selected from the group consisting of:
2-[[(2-carboxypropyl)hydroxyphosphinyl]methyl]-pentanedioic acid;
2-[[(2-carboxybutyl)hydroxyphosphinyl]methyl]-pentanedioic acid;
2-[[(2-carboxypentyl)hydroxyphosphinyl]methyl]-pentanedioic acid;
2-[[(2-carboxy-3-phenylpropyl)hydroxyphosphinyl]methyl]-pentanedioic acid;
2-[[(2-carboxy-3-naphthylpropyl)hydroxyphosphinyl]methyl]pentanedioic acid;
2-[[(2-carboxy-3-pyridylpropyl)hydroxyphosphinyl]methyl]-pentanedioic acid;
2-[[(2-benzyloxycarbonyl)-3-phenylpropyl)hydroxyphosphinyl]methyl]pentanedioic acid;
2-[[(2-methoxycarbonyl)-3-phenylpropyl)hydroxyphosphinyl]methyl]pentanedioic acid;
2-[[(3-carboxy-2-methoxycarbonyl)propyl)hydroxyphosphinyl]methyl]pentanedioic acid;
2-[[(4-carboxy-2-methoxycarbonyl)butyl)hydroxyphosphinyl]methyl]pentanedioic acid; and
pharmaceutically acceptable salts, hydrates and prodrugs thereof.

37. The method of claim 1, wherein the NAALADase inhibitor is a compound of Formula II:

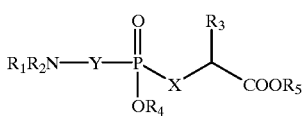

XII or a pharmaceutically acceptable salt, hydrate, or prodrug thereof, wherein:

X is $C_6R_7$, O, or $NR_8$;

Y is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_1$, wherein Y is unsubstituted or substituted with one or more substituent(s);

$R_1$ and $R_2$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_2$, carboxy, carbonyl, sulfonyl, formanilido, and thioformamido, wherein $R_1$ and $R_2$ are independently unsubstituted or substituted with one or more substituent(s); or $R_1$ and $R_2$ are taken together, with the nitrogen atom to which they are attached, to form a 5–7 membered azaheterocyclic ring, wherein said azaheterocyclic ring contains one or more heteroatom(s) independently selected from the group consisting of N, O, and S, and said azaheterocyclic ring is unsubstituted or substituted with one or more substituent(s);

$R_3$, $R_4$, $R_5$, $R_6$, $R_7$, and $R_8$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, and $Ar_3$, wherein $R_3$, $R_4$, $R_5$, $R_6$, $R_7$, and $R_8$ are independently unsubstituted or substituted with one or more substituent(s); and $Ar_1$, $Ar_2$, and $Ar_3$ are independently a carbocyclic or heterocyclic moiety, which is unsubstituted or substituted with one or more substituent(s);

wherein said substituent(s) is/are independently selected from the group consisting of C1–C9 straight or branched chain alkyl, C2–C9 straight or branched chain alkenyl, C1–C9 alkoxy, C2–C9 alkenyloxy, phenoxy, benzyloxy, C3–C8 cycloalkyl, C5–C7 cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties selected from the group consisting of phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

38. The methods of claim 37, wherein:

X is $CH_2$, $R_3$ is $(CH_2)_2COOH$, $R_4$ is hydrogen, $R_5$ is hydrogen, and $R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_2$, carboxy, carbonyl, sulfonyl, formanilido, or thioformamido, wherein $R_1$ is unsubstituted or substituted with one or more substituent(s).

39. The method of claim 38, wherein the compound of Formula XII is selected from the group consisting of:

2-[({[Benzylamino]benzyl}(hydroxyphosphinyl))-methyl]pentanedioic acid;

2-[({[Carboxyamino]benzyl}(hydroxyphosphinyl))-methyl]pentanedioic acid;

2-[({[Acetylamino]benzyl}(hydroxyphosphinyl))-methyl]pentanedioic acid;

2-[({[Dibenzylamino]benzyl}(hydroxyphosphinyl))-methyl]pentanedioic acid;

2-[({[Phenylamino]benzyl}(hydroxyphosphinyl))-methyl]pentanedioic acid;

2-({[(Phenylcarbonylamino)benzyl](hydroxy-phosphinyl)}methyl)pentanedioic acid;

2-({[(Phenylsulfonylamino)benzyl](hydroxy-phosphinyl)}methyl)pentanedioic acid;

2-[({[(2-Fluorophenyl)amino]benzyl}(hydroxy-phosphinyl))methyl]pentanedioic acid;

2-[({[(3-Fluorophenyl)amino]benzyl}(hydroxy-phosphinyl))methyl]pentanedioic acid;

2-[({[(4-Fluorophenyl)amino]benzyl}(hydroxy-phosphinyl))methyl]pentanedioic acid;

2-[({[(2-Chlorophenyl)amino]benzyl}(hydroxy-phosphinyl))methyl]pentanedioic acid;

2-[({[(3-Chlorophenyl)amino]benzyl}(hydroxy-phosphinyl))methyl]pentanedioic acid;

2-[({[(4-Chlorophenyl)amino]benzyl}(hydroxy-phosphinyl))methyl]pentanedioic acid;

2-[({[(2-Methoxyphenyl)amino]benzyl}(hydroxy-phosphinyl))methyl]pentanedioic acid;

2-[({[(3-Methoxyphenyl)amino]benzyl}(hydroxy-phosphinyl))methyl]pentanedioic acid;

2-[({[(4-Methoxyphenyl)amino]benzyl}(hydroxy-phosphinyl))methyl]pentanedioic acid;

2-[({[(2-Hydroxyphenyl)amino]benzyl}(hydroxy-phosphinyl))methyl]pentanedioic acid;

2-[({[(3-Hydroxyphenyl)amino]benzyl}(hydroxy-phosphinyl))methyl]pentanedioic acid;

2-[({[(4-Hydroxyphenyl)amino]benzyl}(hydroxy-phosphinyl))methyl]pentanedioic acid;

2-[({[(2-Carboxyphenyl)amino]benzyl}(hydroxy-phosphinyl))methyl]pentanedioic acid;

2-[({[(3-Carboxyphenyl)amino]benzyl}(hydroxy-phosphinyl))methyl]pentanedioic acid;

2-[({[(4-Carboxyphenyl)amino]benzyl}(hydroxy-phosphinyl))methyl]pentanedioic acid;

2-[({[(2-Nitrophenyl)amino]benzyl}(hydroxy-phosphinyl))methyl]pentanedioic acid;

2-[({[(3-Nitrophenyl)amino]benzyl}(hydroxy-phosphinyl))methyl]pentanedioic acid;

2-[({[(4-Nitrophenyl)amino]benzyl}(hydroxy-phosphinyl))methyl]pentanedioic acid;

2-[({[(2-Sulfonylphenyl)amino]benzyl}(hydroxy-phosphinyl))methyl]pentanedioic acid;

2-[({[(3-Sulfonylphenyl)amino]benzyl}(hydroxy-phosphinyl))methyl]pentanedioic acid;

2-[({[(4-Sulfonylphenyl)amino]benzyl}(hydroxy-phosphinyl))methyl]pentanedioic acid;
2-[({[(2-Methylphenyl)amino]benzyl}-(hydroxyphosphinyl))methyl]pentanedioic acid;
2-[({[(3-Methylphenyl)amino]benzyl}-(hydroxyphosphinyl))methyl]pentanedioic acid;
2-[({[(4-Methylphenyl)amino]benzyl}-(hydroxyphosphinyl))methyl]pentanedioic acid;
2-[({[(2-Tert-butylphenyl)amino]benzyl}-(hydroxyphosphinyl))methyl]pentanedioic acid;
2-[({[(3-Tert-butylphenyl)amino]benzyl}-(hydroxyphosphinyl))methyl]pentanedioic acid;
2-[({[(4-Tert-butylphenyl)amino]benzyl}-(hydroxyphosphinyl))methyl]pentanedioic acid;
2-[({[(2-Trifluoromethylphenyl)amino]benzyl}-(hydroxyphosphinyl))methyl]pentanedioic acid;
2-[({[(3-Trifluoromethylphenyl)amino]benzyl}-(hydroxyphosphinyl))methyl]pentanedioic acid;
2-[({[(4-Trifluoromethylphenyl)amino]benzyl}-(hydroxyphosphinyl))methyl]pentanedioic acid;
2-[({[(Thioformanilido)amino]benzyl}-(hydroxyphosphinyl))methyl]pentanedioic acid;
2-[({[1,3-Dioxo-2,3-dihydro-1H-2-isoindolyl]benzyl}hydroxyphosphinyl)methyl]pentanedioic acid;
2-[({[Benzylamino]methyl}(hydroxyphosphinyl))-methyl]pentanedioic acid;
2-[({[Carboxyamino]methyl}(hydroxyphosphinyl))-methyl]pentanedioic acid;
2-[({[Acetylamino]methyl}(hydroxyphosphinyl))-methyl]pentanedioic acid;
2-[({[Diphenylamino]methyl}(hydroxyphosphinyl))-methyl]pentanedioic acid;
2-[({[Phenylamino]methyl}(hydroxyphosphinyl))-methyl]pentanedioic acid;
2-({[(Phenylcarbonylamino)methyl](hydroxy-phosphinyl)}methyl)pentanedioic acid;
2-({[(Phenylsulfonylamino)methyl](hydroxy-phosphinyl)}methyl)pentanedioic acid;
2-[({[(2-Fluorophenyl)amino]methyl}(hydroxy-phosphinyl))methyl]pentanedioic acid;
2-[({[(3-Fluorophenyl)amino]methyl}(hydroxy-phosphinyl))methyl]pentanedioic acid;
2-[({[(4-Fluorophenyl)amino]methyl}(hydroxy-phosphinyl))methyl]pentanedioic acid;
2-[({[(2-Chlorophenyl)amino]methyl}(hydroxy-phosphinyl))methyl]pentanedioic acid;
2-[({[(3-Chlorophenyl)amino]methyl}(hydroxy-phosphinyl))methyl]pentanedioic acid;
2-[({[(4-Chlorophenyl)amino]methyl}(hydroxy-phosphinyl))methyl]pentanedioic acid;
2-[({[(2-Methoxyphenyl)amino]methyl}(hydroxy-phosphinyl))methyl]pentanedioic acid;
2-[({[(3-Methoxyphenyl)amino]methyl}(hydroxy-phosphinyl))methyl]pentanedioic acid;
2-[({[(4-Methoxyphenyl)amino]methyl}(hydroxy-phosphinyl))methyl]pentanedioic acid;
2-[({[(2-Hydroxyphenyl)amino]methyl}(hydroxy-phosphinyl))methyl]pentanedioic acid;
2-[({[(3-Hydroxyphenyl)amino]methyl}(hydroxy-phosphinyl))methyl]pentanedioic acid;
2-[({[(4-Hydroxyphenyl)amino]methyl}(hydroxy-phosphinyl))methyl]pentanedioic acid;
2-[({[(2-Carboxyphenyl)amino]methyl}(hydroxy-phosphinyl))methyl]pentanedioic acid;
2-[({[(3-Carboxyphenyl)amino]methyl}(hydroxy-phosphinyl))methyl]pentanedioic acid;
2-[({[(4-Carboxyphenyl)amino]methyl}(hydroxy-phosphinyl))methyl]pentanedioic acid;
2-[({[(2-Nitrophenyl)amino]methyl}(hydroxy-phosphinyl))methyl]pentanedioic acid;
2-[({[(3-Nitrophenyl)amino]methyl}(hydroxy-phosphinyl))methyl]pentanedioic acid;
2-[({[(4-Nitrophenyl)amino]methyl}(hydroxy-phosphinyl))methyl]pentanedioic acid;
2-[({[(2-Sulfonylphenyl)amino]methyl}(hydroxy-phosphinyl))methyl]pentanedioic acid;
2-[({[(3-Sulfonylphenyl)amino]methyl}(hydroxy-phosphinyl))methyl]pentanedioic acid;
2-[({[(4-Sulfonylphenyl)amino]methyl}(hydroxy-phosphinyl))methyl]pentanedioic acid;
2-[({[(2-Methylphenyl)amino]methyl}-(hydroxyphosphinyl))methyl]pentanedioic acid;
2-[({[(3-Methylphenyl)amino]methyl}-(hydroxyphosphinyl))methyl]pentanedioic acid;
2-[({[(4-Methylphenyl)amino]methyl}-(hydroxyphosphinyl))methyl]pentanedioic acid;
2-[({[(2-Tert-butylphenyl)amino]methyl}-(hydroxyphosphinyl))methyl]pentanedioic acid;
2-[({[(3-Tert-butylphenyl)amino]methyl}-(hydroxyphosphinyl))methyl]pentanedioic acid;
2-[({[(4-Tert-butylphenyl)amino]methyl}-(hydroxyphosphinyl))methyl]pentanedioic acid;
2-[({[(2-Trifluoromethylphenyl)amino]methyl}-(hydroxyphosphinyl))methyl]pentanedioic acid;
2-[({[(3-Trifluoromethylphenyl)amino]methyl}-(hydroxyphosphinyl))methyl]pentanedioic acid;
2-[({[(4-Trifluoromethylphenyl)amino]methyl}-(hydroxyphosphinyl))methyl]pentanedioic acid;
2-[({[(Thioformanilido)amino]benzyl}-(hydroxyphosphinyl))methyl]pentanedioic acid;
2-[({[1,3-Dioxo-2,3-dihydro-1H-2-isoindolyl]methyl}-hydroxyphosphinyl)methyl]pentanedioic acid; and pharmaceutically acceptable salts, hydrates and prodrugs thereof.

40. The method of claim 1, wherein the NAALADase inhibitor is a compound of Formula XIII:

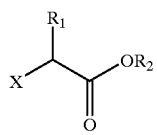

XIII or a pharmaceutically acceptable salt, hydrate, metabolite, or prodrug thereof, wherein:

X is a moiety of Formula XIV, XV, XVI, XVII or XVIII:

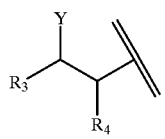

XIV

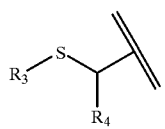

XV

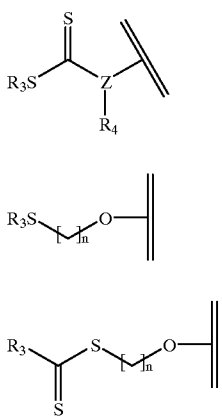

n is 1, 2, 3 or 4;

Y is $SR_5$, $SO3R_5$, $SO_2R_5$, $SOR_5$, $SO(NR_5)_6$ or $S(N_2R_5R_6)R_7$;

Z is N or $CR_8$;

R, $R_1$, $R_2$, $R_3$, $R_4$, $R_5$, $R_6$, $R_7$ and $R_8$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said alkyl, alkenyl, cycloalkyl, cycloalkenyl and $Ar_1$ are independently unsubstituted or substituted with one or more substituent(s); and $Ar_1$ is a carbocyclic or heterocyclic moiety, which is unsubstituted or substituted with one or more substituent(s);

provided that when X is a moiety of Formula XV, $R_1$ is $(CH_2)_2COOR$ or $(CH_2)_2CONHR$, and $R_4$ is hydrogen, then $R_3$ is not hydrogen or COR; and when X is a moiety of Formula XVI, Z is N and $R_1$ is $(CH_2)_2COOH$, then $R_4$ is not hydrogen;

wherein said substituent(s) is/are selected from the group consisting of C1–C9 straight or branched chain alkyl, C2–C9 straight or branched chain alkenyl, C1–C9 alkoxy, C2–C9 alkenyloxy, phenoxy, benzyloxy, C3–C8 cycloalkyl, C5–C7 cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties selected from the group consisting of phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

41. The method of claim 40, wherein:
    $R_1$ is $(CH_2)_2COOH$; and
    $R_2$ is hydrogen.

42. The method of claim 41, wherein the compound is selected from the group consisting of:
2-(2-sulfanylethyl)pentanedioic acid;
2-(2-sulfanylpropyl)pentanedioic acid;
2-(2-sulfanylbutyl)pentanedioic acid;
2-(2-phenyl-2-sulfanylethyl)pentanedioic acid;
2-(2-(4-pyridyl)-2-sulfanylethyl)pentanedioic acid;
2-(1-methyl-2-sulfanylethyl)pentanedioic acid;
2-(1-benzyl-2-sulfanylethyl)pentanedioic acid;
2-(1-methyl-2-sulfanylpropyl)pentanedioic acid;
2-(1-ethyl-2-sulfanylpropyl)pentanedioic acid;
2-(1-propyl-2-sulfanylpropyl)pentanedioic acid;
2-(1-butyl-2-sulfanylpropyl)pentanedioic acid;
2-(2-sulfoethyl)pentanedioic acid;
2-[2-(methylsulfonyl)ethyl]pentanedioic acid;
2-[2-(ethylsulfonyl)ethyl]pentanedioic acid;
2-[2-(propylsulfonyl)ethyl]pentanedioic acid;
2-[2-(butylsulfonyl)ethyl]pentanedioic acid;
2-[2-(methylsulfanyl)-3-phenylpropyl]pentanedioic acid;
2-[2-(ethylsulfanyl)-3-phenylpropyl]pentanedioic acid;
2-[2-(propylsulfanyl)-3-phenylpropyl]pentanedioic acid;
2-[2-(butylsulfanyl)-3-phenylpropyl]pentanedioic acid;
2-[2-(methylsulfanyl)-3-(4-pyridyl)propyl]-pentanedioic acid;
2-[2-(ethylsulfanyl)-3-(4-pyridyl)propyl]-pentanedioic acid;
2-[2-(propylsulfanyl)-3-(4-pyridyl)propyl]-pentanedioic acid;
2-[2-(butylsulfanyl)-3-(4-pyridyl)propyl]-pentanedioic acid;
2-[1-benzyl-2-(methylsulfonyl)ethyl]pentanedioic acid;
2-[1-phenyl-2-(methylsulfonyl)ethyl]pentanedioic acid;
2-[1-(4-pyridyl)-2-(methylsulfonyl)ethyl]-pentanedioic acid;
2-[1-benzyl-2-(ethylsulfonyl)ethyl]pentanedioic acid;
2-[1-phenyl-2-(ethylsulfonyl)ethyl]pentanedioic acid;
2-[1-(4-pyridyl)-2-(ethylsulfonyl)ethyl]pentanedioic acid;
2-(1-benzyl-2-sulfoethyl)pentanedioic acid;
2-(1-phenyl-2-sulfoethyl)pentanedioic acid;
2-(1-(4-pyridyl)-2-sulfoethyl)pentanedioic acid;
2-(1-methyl-2-sulfopropyl)pentanedioic acid;
2-(1-ethyl-2-sulfopropyl)pentanedioic acid;
2-(1-propyl-2-sulfopropyl)pentanedioic acid;
2-(1-butyl-2-sulfopropyl)pentanedioic acid;
2-(1-benzyl-2-sulfobutyl)pentanedioic acid;
2-(1-phenyl-2-sulfobutyl)pentanedioic acid;
2-(1-(4-pyridyl)-2-sulfobutyl)pentanedioic acid;
2-[2-(methylsulfonyl)-1-phenylethyl]pentanedioic acid;
2-[2-(ethylsulfonyl)-1-phenylethyl]pentanedioic acid;
2-[2-(propylsulfonyl)-1-phenylethyl]pentanedioic acid;
2-[2-(butylsulfonyl)-1-phenylethyl]pentanedioic acid;
2-[2-(methylsulfonyl)-1-(4-pyridyl)ethyl]-pentanedioic acid;
2-[2-(ethylsulfonyl)-1-(4-pyridyl)ethyl]pentanedioic acid;
2-[2-(propylsulfonyl)-1-(4-pyridyl)ethyl]-pentanedioic acid;
2-[2-(butylsulfonyl)-1-(4-pyridyl)ethyl]pentanedioic acid;
2-[1-(sulfomethyl)propyl]pentanedioic acid;
2-[1-(sulfomethyl)butyl]pentanedioic acid;
2-(1-phenyl-2-sulfopropyl)pentanedioic acid;
2-(1-(4-pyridyl)-2-sulfopropyl)pentanedioic acid;
2-(1-phenyl-2-sulfobutyl)pentanedioic acid;
2-(1-(4-pyridyl)-2-sulfobutyl)pentanedioic acid;
2-(1-sulfanylethyl)pentanedioic acid;
2-(2-phenyl-1-sulfanylethyl)pentanedioic acid;
2-(2-phenyl-1-sulfanylpropyl)pentanedioic acid;

2-(2-phenyl-1-sulfanylbutyl)pentanedioic acid;
2-(2-(4-pyridyl)-1-sulfanylethyl)pentanedioic acid;
2-(2-(4-pyridyl)-1-sulfanylpropyl)pentanedioic acid;
2-[2-(4-pyridyl)-1-sulfanylbutyl]pentanedioic acid;
2-(2-methyl-1-sulfanylpropyl)pentanedioic acid;
2-(2-methyl-1-sulfanylbutyl)pentanedioic acid;
2-(dithiocarboxymethyl)pentanedioic acid;
2-(1-dithiocarboxyethyl)pentanedioic acid;
2-{[methylthio(thiocarbonyl)]methyl}pentanedioic acid;
2-{[ethylthio(thiocarbonyl)]methyl}pentanedioic acid;
2-{[propylthio(thiocarbonyl)]methyl}pentanedioic acid;
2-{[butylthio(thiocarbonyl)]methyl}pentanedioic acid;
2-(2-dithiocarboxy-1-phenylethyl)pentanedioic acid;
2-(2-dithiocarboxy-1-(4-pyridyl)ethyl)pentanedioic acid;
2-[dithiocarboxy(phenyl)methyl]pentanedioic acid;
2-[dithiocarboxy(4-pyridyl)methyl]pentanedioic acid;
2-[(methylsulfanylthiocarbonyl)amino]pentanedioic acid;
2-[(ethylsulfanylthiocarbonyl)amino]pentanedioic acid;
2-[(propylsulfanylthiocarbonyl)amino]pentanedioic acid;
2-[(butylsulfanylthiocarbonyl)amino]pentanedioic acid;
2-[(dithiocarboxy)amino]pentanedioic acid;
2-[(N-methyldithiocarboxy)amino]pentanedioic acid;
2-(2-sulfanylethoxy)pentanedioic acid;
2-(2-sulfanylpropoxy)pentanedioic acid;
2-(2-sulfanylbutoxy)pentanedioic acid;
2-(2-sulfanyl-2-phenyl-1-ethoxy)pentanedioic acid;
2-(2-sulfanyl-2-phenyl-1-propoxy)pentanedioic acid;
2-(2-sulfanyl-2-phenyl-1-butoxy)pentanedioic acid;
2-(2-sulfanyl-2-(4-pyridyl)-1-ethoxy)pentanedioic acid;
2-(2-sulfanyl-2-(4-pyridyl)-1-propoxy)pentanedioic acid;
2-(2-sulfanyl-2-(4-pyridyl)-1-butoxy)pentanedioic acid;
2-(1-sulfanylethoxy)pentanedioic acid;
2-(1-sulfanylpropoxy)pentanedioic acid;
2-(1-sulfanylbutoxy)pentanedioic acid;
2-(1-sulfanyl-2-phenyl-1-ethoxy)pentanedioic acid;
2-(1-sulfanyl-2-phenyl-1-propoxy)pentanedioic acid;
2-(1-sulfanyl-2-phenyl-1-butoxy)pentanedioic acid;
2-(1-sulfanyl-2-(4-pyridyl)-1-ethoxy)pentanedioic acid;
2-(1-sulfanyl-2-(4-pyridyl)-1-propoxy)pentanedioic acid;
2-(1-sulfanyl-2-(4-pyridyl)-1-butoxy)pentanedioic acid; and
pharmaceutically acceptable salts, hydrates, metabolites, and prodrugs thereof.

43. The method of claim 40, wherein:
$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein $R_1$ is unsubstituted or substituted with one or more substituent(s).

44. The method of claim 43, wherein the compound is selected from the group consisting of:
2-benzyl-4-sulfanylbutanoic acid;
2-benzyl-4-sulfanylpentanoic acid;
2-phenyl-4-sulfanylbutanoic acid;
2-phenyl-4-sulfanylpentanoic acid;
2-(4-pyridyl)-4-sulfanylbutanoic acid;
2-(4-pyridyl)-4-sulfanylpentanoic acid;
2-(3-pyridylmethyl)-4-sulfanylpentanoic acid;
2-(3-pyridylmethyl)-4-sulfanylhexanoic acid;
2-benzyl-3-sulfanylpropanoic acid;
2-benzyl-3-sulfanylbutanoic acid;
2-benzyl-3-sulfanylpentanoic acid;
2-phenyl-3-sulfanylpropanoic acid;
2-phenyl-3-sulfanylbutanoic acid;
2-phenyl-3-sulfanylpentanoic acid;
2-(4-pyridyl)-3-sulfanylpropanoic acid;
2-(4-pyridyl)-3-sulfanylbutanoic acid;
2-(4-pyridyl)-3-sulfanylpentanoic acid;
2-(4-pyridylmethyl)-3-sulfanylpropanoic acid;
2-(4-pyridylmethyl)-3-sulfanylbutanoic acid;
2-(4-pyridylmethyl)-3-sulfanylpentanoic acid; and
pharmaceutically acceptable salts, hydrates, metabolites, and prodrugs thereof.

45. The method of claim 1, wherein the NAALADase inhibitor is a compound of Formula XIX:

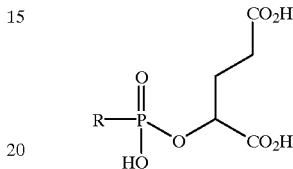

XIX or a pharmaceutically acceptable salt or hydrate thereof, wherein:
R is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, Ar and mixtures thereof, wherein said R is unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar or a mixture thereof;
Ar is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_6$ alkoxy or $C_1$–$C_6$ alkenyloxy, phenoxy, benzyloxy, and amino.

46. The method of claim 45, wherein the compound is selected from the group consisting of:
2-[[methylhydroxyphosphinyl]oxy]pentanedioic acid;
2-[[ethylhydroxyphosphinyl]oxy]pentanedioic acid;
2-[[propylhydroxyphosphinyl]oxy]pentanedioic acid;
2-[[butylhydroxyphosphinyl]oxy]pentanedioic acid;
2-[[phenylhydroxyphosphinyl]oxy]pentanedioic acid;
2-[[((4pyridyl)methyl)hydroxyphosphinyl]oxy]pentanedioic acid;
2-[[((2-pyridyl)methyl)hydroxyphosphinyl]oxy]-pentanedioic acid;
2-[[(phenylmethyl)hydroxyphosphinyl]oxy]pentanedioic acid;
2-[[((2-phenylethyl)methyl)hydroxyphosphinyl]oxy]-pentanedioic acid; and
pharmaceutically acceptable salts, hydrates, metabolites, and prodrugs thereof.

* * * * *